US006180675B1

(12) United States Patent
Widdowson et al.

(10) Patent No.: US 6,180,675 B1
(45) Date of Patent: Jan. 30, 2001

(54) IL-8 RECEPTOR ANTAGONISTS

(75) Inventors: Katherine Louisa Widdowson, King of Prussia; Daniel Frank Veber, Ambler; Anthony Joseph Jurewicz, Royersford; Robert Philip Hertzberg, Downingtown; Melvin Clarence Rutledge, Jr., Lansdale, all of PA (US)

(73) Assignee: SmithKline Beecham Corporation, Philadelphia, PA (US)

(*) Notice: Under 35 U.S.C. 154(b), the term of this patent shall be extended for 0 days.

(21) Appl. No.: 09/240,354

(22) Filed: Jan. 29, 1999

Related U.S. Application Data

(60) Division of application No. 08/641,990, filed on Mar. 20, 1996, now Pat. No. 5,886,044, which is a continuation-in-part of application No. PCT/US96/02260, filed on Feb. 16, 1996, which is a continuation-in-part of application No. 08/390,260, filed on Feb. 17, 1995, now abandoned.

(51) Int. Cl.$^7$ .................................................... A61K 31/17

(52) U.S. Cl. ........................................ 514/586; 514/597

(58) Field of Search ..................................... 514/586, 597

(56) References Cited

U.S. PATENT DOCUMENTS

| | | |
|---|---|---|
| 2,363,074 | 11/1944 | Martin et al. . |
| 3,332,981 | 7/1967 | Shultis, Jr. et al. . |
| 3,689,550 | 9/1972 | Schellenbaum et al. . |
| 3,855,285 | 12/1974 | Holland . |
| 3,856,951 | 12/1974 | Holland . |
| 3,869,553 | 3/1975 | Holland . |
| 3,882,230 | 5/1975 | Holland . |
| 3,996,253 | 12/1976 | Magnoli et al. . |
| 4,048,333 | 9/1977 | Galabov et al. . |
| 4,405,644 | 9/1983 | Kabbe et al. . |
| 4,591,604 | 5/1986 | Conrow et al. . |
| 4,608,205 | 8/1986 | Conrow et al. . |
| 5,275,932 | 1/1994 | Weigel et al. . |
| 5,312,831 | 5/1994 | Ayral-Kaloustian et al. . |
| 5,384,319 | 1/1995 | Ferrini . |
| 5,384,330 | 1/1995 | Dieter et al. . |
| 5,447,957 | 9/1995 | Adams et al. . |
| 5,470,882 | 11/1995 | Dixon et al. . |
| 5,585,518 | 12/1996 | Marschner et al. . |
| 5,621,010 | 4/1997 | Sueda et al. . |

FOREIGN PATENT DOCUMENTS

| | | |
|---|---|---|
| 93134950 | 3/1993 | (AU) . |
| 1157022 | 11/1983 | (CA) . |
| 1166252 | 4/1984 | (CA) . |
| 2241470 | 10/1973 | (DE) . |
| 253 997 A1 | 2/1988 | (DE) . |
| 467185 | 1/1992 | (EP) . |
| 0 541 112 | 5/1993 | (EP) . |
| 0 561 687 | 9/1993 | (EP) . |
| 1 210 596 | 10/1970 | (GB) . |
| 1 281 437 | 7/1972 | (GB) . |
| 1393854 | 2/1973 | (GB) . |
| 55-098152 | 7/1980 | (JP) . |
| 60-126256 | 7/1985 | (JP) . |
| 02009827 | 1/1990 | (JP) . |
| 03215848 | 9/1992 | (JP) . |
| 6-313992 | 11/1994 | (JP) . |
| 506240 | 6/1971 | (SE) . |
| WO 93 14146 | 7/1993 | (WO) . |
| WO93/16992 | 9/1993 | (WO) . |
| WO 94 07507 | 4/1994 | (WO) . |
| WO94/22807 | 10/1994 | (WO) . |
| WO 96/10213 | 4/1996 | (WO) . |

OTHER PUBLICATIONS

Lozanova et al., Dokl. Bulg. Akad. Nauk, 46(11), pp. 85–88 (1993).
Hauptmann et al., *Chemical Abstracts*, vol. 109, No. 25, 1988, p. 816. Abstract No. 230,571k.
Hauptmann et al., Derwent Abstracts, vol. 88, Abstract No. 183601, 1988.
Broome et al., Ind Chem Belge, Vol 32, 1967.
Rao et al., J. Ind. Chem. Soc., Vol L, 492–4 (1973).
Tanaka et al. J. Agric. Food Chem, Vol 27 (2), 311–15, (1979).
Patil et al., Indian J. Pharm. Sci., Vol 49 (6), 229–231, (1987).
Warren et al., Drug Metab. Dispos., Vol 6 (1), 38–44, (1978).
Craig et al., Drug Metab. Dispos, Vol 17 (3), 345–347 (1989).
Jeffcoat et al., Drug Metab. Dispos, Vol 5 (2), 157–66 (1980).
Hiles et al., Toxical. Appl. Pharm, Vol 46 (2), 323–37 (1978).
Carini et al., J. Med Chem, Vol 33 (5), 1330–6 (1990).
Gruenke et al., J. Anal Toxicol, Vol 11 (2), 75–80 (1987).
Sugihara, T., Nippon Kasei Gakkaishi, 43(3), 207–214 (1992).
Sugihara, T., Nippon Kasei Gakkaishi, 40(8), 691–6 (1989).
Roy, S. et al., Cell. Immunol., 105(1), 118–26 (1987).
Christove, A. et al., Dokl Bolg. Akad. Nauk. 39(3), 125–8 (1986).
Mashev, N. et al., Dokl Bolg. Akad. Nauk, 38(1), 107–9 (1985).
Schuster, G. et al., Z. Pflanzenkrankh, 90(5), 500–4 (1983).
Vasilev, G. et al., Dokl. Bolg. Akad. Nauk., 35(8), 1141–4 (1982).
Schuster, G., Wiss Z., Karl Marx Univ. Leipzig, Math, 31(4), 321–30 (1982).
Nakov, B. et al., Nauchni Tr., Vissh Selskostop. Inst. "Vasil Kolarov", 26(4), Plovdiv, 231–9 (1981).

(List continued on next page.)

*Primary Examiner*—William R. A. Jarvis
(74) *Attorney, Agent, or Firm*—Soma G. Simon; Dara L. Dinner; Charles M. Kinzig

(57) ABSTRACT

This invention relates to the novel use of phenyl ureas in the treatment of disease states mediated by the chemokine, Interleukin-8 (IL-8).

7 Claims, No Drawings

OTHER PUBLICATIONS

Iwamura, Hajime, et al., Phytochemistry, 19(7), 1309–19 (1980).
Galabov, A. et al., J. Med. Chem., 23(9), 1048–51 (1980).
Mashev, N. et a., Dokl. Bolg. Akad. Nauk, 32(11), 1555–8 (1979).
Galabov, A., Probl. Infect. Parasit. Dis., 7, 19–24 (1979).
Franke, R. et al., Dokl. Bolg. Akad. Nauk., 32(3), 369–71 (1979).
Krause G. et al., Biochem. Physiol. Pflanz., 174(2), 128–38 (1979).
Vasilev G. et al., Fiziol. Rast (Moscow), 25(5), 1070 (1978).
Vasilev G. et al., Plant Growth Regul., Proc. Int. Symp. 1975, mtg date, 511–14 (1977).
Galabov, A. et al., Chemoterapty (Basel), 23(2), 81–9 (1977).
Galabov A., Dokl. Bolg. Akad. Nauk, 29(8), 1219–22 (1976).
Radnev R. et al., Rastenievud. Nauki, 12 (8), 21–7 (1975).
Mashev N. et al., Fixiol. Rast. (Sofia), 1(2), 19–29 (1974).
Mashev N. et a., Dokl. Skh. Akad., Sofia, 7(1), 11–15 (1974).
Vasilev G.N. et al., Biochem Physiol. Pflanz., 165 (5/6), 467–78 (1974).
Galubov, A.S. et al., Antimicrob. Agents Chemother., 5(1), 108 (1974).
Galabov, A.S., Prof. Chemother., 2, 981–5 (1973).
Vasilev, G. et al., Izv. Inst. Fiziol. Rast., 18, 155–73 (1973).
Vasilev, G. et al., Arch. Phytopathol., 9(5), 309–20 (1973).
Vasilev, G. et al., Dokl. Bolg. Akad. Nauk, 26(4), 513–516 (1973).
Ivanova, Y.A. et al., Dokl. Bolg. Akad. Nauk, 25(8), 1101–4 (1972).
Ivanov, I.A. et al., Dokl. Bolg. Akad. Nauk, 25(6), 799–802 (1972).
Vasilev G.N. et al., Dokl. Bolg. Akad. Nauk, 25(7), 941–4 (1972).
Galabov, A. et al., Arach. Gesamte Virusforsch, 28(2–3), 159–66 (1972).
Galabov, A. et al., Chemotherapy 17(3), 161–74 (1972).
Karanov, E et al., Izv. Inst. Fiziol. Fast. Bulg. Acad. Nauk., 16, 167–89 (1970).
Vasilev G. et al., Dokl. Akad. Sel'skokhoz Hauk Bolg., 2(4), 349–57 (1969).
Winkelmann, E., Arzheim. Forsch., 19(4), 543–58 (1969).
Vasilev G. et al., Dokl. Bolg. Akad. Nauk 22(5), 567–70 (1969).
Vasilev G. et al., C.R. Acad. Bulg. Sci., 20(5), 477–80 (1967).
Gruenke, L.D., et al., J. Anal Toxicol., 11(2), 75–80 (1987).
Olesen et al., Chemical Abstracts, 122(7), (1995).

IL-8 RECEPTOR ANTAGONISTS

This application is a divisional of U.S. Ser. No. 08/641,990, filed Mar. 20, 1996, now U.S. Pat. No. 5,886,044, which is a CIP of PCT/US96/02260, filed Feb. 16, 1996, which is a CIP of U.S. Ser. No. 08/390,260, filed Feb. 17, 1995, now abandoned.

FIELD OF THE INVENTION

This invention relates to a novel group of phenyl urea compounds, processes for the preparation thereof, the use thereof in treating IL-8, GROα, GROβ, GROγ and NAP-2 mediated diseases and pharmaceutical compositions for use in such therapy.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al. *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

GROα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al, J. Cell Physiology 129, 375 (1986) and Chang et al, *J. Immunol* 148, 451 (1992). All of the chemokines of the α-family which possess the ELR motif directly preceding the CXC motif bind to the IL-8 B receptor.

IL-8, GROα, GROβ, GROγ and NAP-2 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al, Science 258, 1798 (1992).

In vitro, IL-8, Groα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al.,*J. Biol. Chem.* 267, 16283 (1992); LaRosa et al., *J. Biol. Chem.* 267, 25402 (1992); and Gayle et al.,*J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTON

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective ammount of a compound of Formula (I).

Compounds of Formula (I) useful in the present invention are represented by the structure:

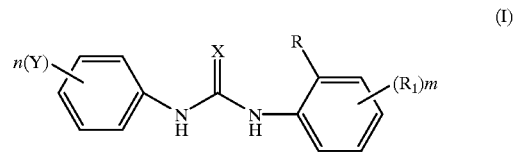

wherein

X is oxygen or sulfur;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$;

C(O)OR$_{12}$; OC(O)R$_{11}$; NR$_4$C(O)R$_{11}$; or two R$_1$ moieties together may form O—(CH$_2$)$_s$O— or a 5 to 6 membered unsaturated ring;

t is 0, or an integer having a value of 1 or 2;

s is an integer having a value of 1 to 3;

R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, heterocyclic C$_{1-4}$ alkyl, or R$_4$ and R$_5$ together with the nitrogen to which they are attached form a 5 to 7 member ring which may optionally comprise an additional heteroatom selected from O/N/S;

Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; S(O)$_t$R$_4$; hydroxy; hydroxyC$_{1-4}$alkyl; aryl; aryl C$_{1-4}$ alkyl; aryloxy; arylC$_{1-4}$ alkyloxy; heteroaryl; heteroarylalkyl; heteroaryl C$_{1-4}$ alkyloxy; heterocyclic, heterocyclic C$_{1-4}$alkyl; aryl C$_{2-10}$ alkenyl; heteroaryl C$_{2-10}$ alkenyl; heterocyclic C$_{2-10}$ alkenyl; NR$_4$R$_5$; C$_{2-10}$ alkenyl C(O)NR$_4$R$_5$; C(O)NR$_4$R$_5$; C(O)NR$_4$R$_{10}$; S(O)$_3$H; S(O)$_3$R$_8$; C$_{1-10}$ alkyl C(O)R$_{11}$; C$_{2-10}$ alkenyl C(O)R$_{11}$; C$_{2-10}$ alkenyl C(O)OR$_{11}$; C(O)R$_{11}$; C(O)OR$_{12}$; OC(O)R$_{11}$; NR$_4$C(O)R$_{11}$; or two Y moieties together may form O—(CH$_2$)$_s$O— or a 5 to 6 membered unsaturated ring;

n is an integer having a value of 1 to 3;

m is an integer having a value of 1 to 3;

R$_8$ is hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl;

R$_{12}$ is hydrogen, C$_{1-10}$ alkyl, optionally substituted aryl or optionally substituted arylalkyl;

or a pharmaceutically acceptably salt thereof.

Another aspect of the present invention is to a method of treating a chemokine mediated disease, wherein the chemokine is one which binds to an IL-8 α or β receptor and which method comprises administering an effective amount of a compound of Formula (II) or a pharmaceutically acceptable salt thereof, as defined herein.

This invention also relates to a method of inhibiting the binding of IL-8 to its receptors in a mammal in need thereof which comprises administering to said mammal an effective amount of a compound of Formula (II), as defined herein.

This invention also relates to the novel compounds of Formula (II), or a pharmaceutically acceptable salt thereof, as defined herein.

Another aspect of the present invention is to a method of treating a chemokine mediated disease, wherein the chemokine is one which binds to an IL-8 α or β receptor and which method comprises administering an effective amount of a compound of Formula (III) or a pharmaceutically acceptable salt thereof, as defined herein.

This invention also relates to a method of inhibiting the binding of IL-8 to its receptors in a mammal in need thereof which comprises administering to said mammal an effective amount of a compound of Formula (III), as defined herein.

This invention also relates to the novel compounds of Formula (III), or a pharmaceutically acceptable salt thereof, as defined herein.

DETAILED DESCRIPTION OF THE INVENTION

The compounds of Formula (I) may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

In compounds of Formula (I), R is suitably any functional moiety which provides an ionizable hydrogen having a pKa of 10 or less, preferably from about 3 to 9, more preferably from about 3 to 7. Such functional groups include, but are not limited to, hydroxy, carboxylic acid, thiol, —SR$_2$—OR$_2$, —NH—C(O)R$_a$, —C(O)NR$_6$R$_7$, a substituted sulfonamides of the formula —NHS(O)$_2$R$_b$, —S(O)$_2$NHR$_c$, NHC(X$_2$) NHR$_b$, or a tetrazolyl; wherein X$_2$ is oxygen or sulfur, preferably oxygen. Preferably, the functional group is other than a sulfonic acid, either directly or as a substituent group on the aryl, heteroaryl, or heterocyclic moiety ring, such as in SR$_2$ or OR$_2$. More preferably R is OH, SH, or NHS(O)$_2$R$_b$. Suitably, R$_2$ is a substituted aryl, heteroaryl, or heterocyclic moiety which ring has the functional moiety providing the ionizable hydrogen having a pKa of 10 or less.

Suitably, R$_6$ and R$_7$ are independently hydrogen or a C$_{1-4}$ alkyl group, or R$_6$ and R$_7$ together with the nitrogen to which they are attached form a 5 to 7 member ring which ring may optionally contain an additional heteroatom which heteroatom is selected from oxygen, nitrogen or sulfur. This heteroring may be optionally substituted as defined herein.

Suitably R$_a$ is an alkyl, aryl, arylC$_{1-4}$alkyl, heteroaryl, heteroarylC$_{1-4}$alkyl, heterocyclic, or a heterocyclic C$_{1-4}$alkyl moiety, all of which may be optionally substituted, as defined herein below.

Suitably, R$_b$ is a NR$_6$R$_7$, alkyl, aryl, arylC$_{1-4}$alkyl, arylC$_{2-4}$alkenyl, heteroaryl, heteroarylC$_{1-4}$alkyl, heteroarylC$_{2-4}$ alkenyl, heterocyclic, or heterocyclic C$_{1-4}$akyl, or a heterocyclic C$_{2-4}$alkenyl moiety, camphor, all of which may be optionally substituted one to three times independently by halogen; nitro; halosubstituted C$_{1-4}$ alkyl. such as CF$_3$; C$_{1-4}$ alkyl, such as methyl; C$_{1-4}$ alkoxy, such as methoxy; NR$_9$C(O)R$_a$; C(O)NR$_6$R$_7$, S(O)$_3$H, or C(O)OC$_{1-4}$ alkyl. R$_b$ is preferably an optionally substituted phenyl, benzyl, or styryl. When R$_b$ is a heteroaryl preferably it is an optionally substituted thiazole, optionally substituted thienyl, or optionally substituted quinolinyl ring. Wherein R$_9$ is hydrogen or a C$_{1-4}$ alkyl, preferably hydrogen, and suitably when the substituent group is NR$_9$C(O)R$_a$, then R$_a$ is preferably an alkyl group, such as methyl.

Suitably R$_c$ is hydrogen, alkyl, aryl, arylC$_{1-4}$alkyl, arylC$_{1-4}$alkenyl, heteroaryl, heteroarylC$_{1-4}$alkyl, heteroarylC$_{1-4}$alkenyl, heterocyclic, or heterocyclic C$_{1-4}$alkyl, or a heterocyclic C$_{1-4}$alkenyl moiety, all of which may be optionally substituted one to three times independently by halogen, nitro, halosubstituted C$_{1-4}$ alkyl, C$_{1-4}$ alkyl, C$_{1-4}$ alkoxy, NR$_9$C(O)R$_a$, C(O)NR$_6$R$_7$, S(O)$_3$H, or C(O)OC$_{1-4}$ alkyl, wherein R$_9$ is hydrogen or a C$_{1-4}$ alkyl. Preferably, R$_c$ is an optionally substituted phenyl.

When R is an OR$_2$ or SR$_2$ moiety it is recognized by one of skill in the art that the aryl ring must, therefore, contain the required ionizable hydrogen. The aryl ring may also be additionally substituted, independently, by one to three groups, which groups may also contain an additional ionizable group, and which include but are not limited to, halogen, nitro, halosubstituted C$_{1-4}$ alkyl, C$_{1-4}$ alkyl, C$_{1-4}$ alkoxy, hydroxy, SH, —C(O)NR$_6$R$_7$, —NH—C(O)R$_a$, —NHS(O)$_2$R$_b$, S(O)$_2$NR$_6$R$_7$, C(O)OR$_8$, or a tetrazolyl ring.

In compounds of Formula (I), suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $S(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; $NR_4R_5$; $C_{2-10}$ alkenyl-$C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$, $C_{2-10}$ alkenyl $C(O)OR_{11}$; $C(O)R_{11}$; $C(O)OR_{12}$, such as carboxy, methylcarboxylate or phenylbenzoate; $OC(O)R_{11}$; $NR_4C(O)R_{11}$; azido; or two $R_1$ moieties together may form O—$(CH_2)_s$O— or a 5 to 6 membered unsaturated ring; and s is an integer having a value of 1 to 3. The aryl, arylalkyl, arylalkenyl, heteroaryl, heteroarylalkyl, heteroarylalkenyl, heterocyclic, heterocyclicalkyl, and heterocyclicalkenyl moieties may all be optionally substituted as defined herein below. Preferably $R_1$ is other than azido or $S(O)_3R_8$.

When $R_1$ forms a dioxybridge, s is preferably 1. When $R_1$ forms an additional unsaturated ring, it is preferably 6 membered resulting in a naphthylene ring system. This naphthylene ring may be substituted independently, 1 to 3 times by the other $R_1$ moieties as defined above.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

$R_{10}$ is suitably $C_{1-10}$ alkyl $C(O)_2R_8$, such as $CH_2C(O)_2H$ or $CH_2C(O)_2CH_3$.

$R_{11}$ is suitably hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

$R_{12}$ is suitably hydrogen, $C_{1-10}$ alkyl, optionally substituted aryl or optionally substituted arylalkyl.

Preferably $R_1$ is halogen, cyano, nitro, $CF_3$, $C(O)NR_4R_5$, alkenyl $C(O)NR_4R_5$, $C(O)$ $R_4R_{10}$, alkenyl $C(O)OR_{12}$, heteroaryl, heteroarylalkyl, heteroaryl alkenyl, or $S(O)NR_4R_5$, and preferably $R_4$ and $R_5$ are both hydrogen or one is phenyl. A preferred ring substitution for $R_1$ is in the 4-position of the phenyl ring.

When R is OH, SH or $NSO_2R_b$ than $R_1$ is preferably substituted in the 3-position, the 4-position or di substituted in the 3,4-position. The substituent group is suitably an electron withdrawing moiety. Preferably when R is OH, SH or $NSO_2R_b$, than $R_1$ is nitro, halogen, cyano, trifluoromethyl group, $C(O)NR_4R_5$.

When R is carboxylic acid, than $R_1$ is preferably hydrogen, or $R_1$ is preferably substituted in the 4-position, more preferably substituted by trifluoromethyl or chloro.

In compounds of Formula (I), suitably Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy $C_{1-4}$alkyl; aryl; aryl $C_{1-4}$ alkyl; aryloxy; aryl$C_{1-4}$ alkyloxy; aryl $C_{2-10}$ alkenyl; heteroaryl; heteroarylalkyl; heteroaryl $C_{1-4}$ alkyloxy; heteroaryl $C_{2-10}$ alkenyl; heterocyclic, heterocyclic $C_{1-4}$alkyl; heterocyclic$C_{2-10}$ alk-enyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; azido; or two Y moieties together may form O—$(CH_2)_s$O— or a 5 to 6 membered unsaturated ring. When Y forms a dioxybridge, s is preferably 1. When Y forms an additional unsaturated ring, it is preferably 6 membered resulting in a naphthylene ring system. This naphthylene ring may be substituted 1 to 3 times by other Y moieties as defined above. The aryl, heteroaryl and heterocyclic moieties noted above may all be optionally substituted as defined herein. Preferably $R_1$ is other than azido or $S(O)_3R_8$.

Y is preferably a halogen, $C_{1-4}$ alkoxy, optionally substituted aryl, optionally substituted aryloxy or arylalkoxy, methylene dioxy, $NR_4R_5$, thio $C_{1-4}$alkyl, thioaryl, halosubstituted alkoxy, optionally substituted $C_{1-4}$ alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'-position or 2'-, 3'-position.

While Y may be substituted in any of the 5 ring positions, preferably when R is OH, SH, or $NSO_2R_b$, Y is preferably mono-substituted in the 2'-position or 3'-position, with the 4'- preferably being unsubstituted. If the ring is disubstituted, when R is OH, SH, or $NSO_2R_b$, substituents are preferably in the 2' or 3' position of a monocyclic ring. While both $R_1$ and Y can both be hydrogen, it is prefered that at least one of the rings be substituted, preferably both rings are substituted.

In compounds of Formula (I), X is suitably oxygen or sulfur, preferably oxygen.

While not explicitly covered by Formula (I), (Ia–c), (II), or (III), another aspect of this invention are the symmetrical bis compounds which are included for each structure.

Compounds exemplified by this bis like structure include:
N-(Bis (2-hydroxy-4-nitrophenyl) N'-(dianisdine)diurea
4-Methylene bis(N-(2-chlorophenyl) N'-(2-hydroxy 4-nitrophenyl)urea)
Exemplified compounds of Formula (I) include:
N-[2-Hydroxy-4-(methoxycarbonyl)phenyl]-N'-phenylurea;
N-[5-Nitro-2-hydroxyphenyl]-N'-phenylurea
3-Hydroxy{[(phenylamino)carbonyl]amino}benzamide
N-(2-Hydroxy-4-fluorophenyl)-N'-phenylurea
2-{[(Phenylamino)carbonyl]amino}thiphenol
N-(2-Carboxy-4-hydroxyphenyl)-N'-phenylurea
N-[2-Hydroxy-4-(trifluoromethyl)phenyl]-N'-phenylurea
N-(2-Hydroxy-4-nitrophenyl)-N'-(2-hydroxy-4-nitrophenyl)urea
N-(2-Hydroxy-4-nitrophenyl)-N'-phenyl-thiourea
N-(4-Nitro-2-(phenylsulfonylamino)phenyl)-N'-phenylurea
N-(2-Hydroxy-5-nitrophenyl)-N'-(3-methoxy-2-thienyl) urea
N-(2-Hydroxy-4-nitrophenyl)-N'-(3-methoxy-2-thienyl) urea
N-(2-Hydroxy-4-nitrophenyl)-N'-(3-methoxyphenyl)urea
N-(2-Hydroxy-4-nitrophenyl)-N'-(2-methoxyphenyl)urea
N-(2-Hydroxy-4-nitrophenyl)-N'-(3-trifluoromethylphenyl) urea
N-(2-Hydroxy-4-nitrophenyl)-N'-(2-trifluoromethylphenyl) urea
N-(2-Hydroxy-4-nitrophenyl)-N'-(4-trifluoromethylphenyl) urea
N-(2-Hydroxy-4-nitrophenyl)-N'-(2-bromophenyl)urea
N-(2-Hydroxy-4-nitrophenyl)-N'-(3-bromophenyl)urea N-(2-Hydroxy-4-nitrophenyl)-N'-(4-bromophenyl)urea
N-(2-Hydroxy-4-nitrophenyl)-N'-(2-phenylphenyl)urea
N-(2-Hydroxy-4-nitrophenyl)-N'-(1-naphthyl)urea;
N-(2-Hydroxy-4-nitrophenyl)-N'-(2-nitrophenyl)urea
N-(2-Hydroxy-4-nitrophenyl)-N'-(2-fluorophenyl)urea
N-(2-Hydroxy-4-nitrophenyl)-N'-(2,6-difluorophenyl)urea
N-(2-Hydroxy-4-nitrophenyl)-N'-(2-ethoxyphenyl)urea
N-(2-Hydroxy-4-nitrophenyl)-N'-(2-ethylphenyl)urea
N-(2-Hydroxy-4-nitrophenyl)-N'-(2-trifluoromethoxyphenyl)urea
N-(2-Hydroxy-4-nitrophenyl) N'-(2-methylthiophenyl)urea
N-(2-Hydroxy-4-nitrophenyl) N'-(2-chloro 6-methylphenyl)urea
N-(2-Hydroxy-4-nitrophenyl) N'-(2-sulfoxymethylphenyl)urea
N-(4-Trifluoromethyl-2-hydroxyphenyl) N'-(2-bromophenyl)urea
N-(4-Carbomethoxy 2-hydroxyphenyl) N'-(2-bromophenyl)urea
N-(4-Trifluoromethyl-2-hydroxyphenyl) N'-(2-phenylphenyl)urea
N-(4-Carbomethoxy 2-hydroxyphenyl) N'-(2-phenylphenyl)urea
N-(2-Hydroxy-4-nitrophenyl) N'-(2,3-dichlorophenyl)urea
N-(2-Hydroxy-4-nitrophenyl) N'-(2,4-dichlorophenyl)urea
N-(2-Hydroxy-4-nitrophenyl) N'-(2-chlorophenyl)urea
N-(2-Hydroxy-4-nitrophenyl) N'-(2,4-dibromophenyl)urea
N-(2-Hydroxy-1-napthyl)-N'-(2-bromophenyl)urea
N-(2-Hydroxy-4-nitrophenyl)-N'-(2,3-methylenedioxyphenyl)urea
N-(2-Hydroxy-4-nitrophenyl) N'-(3-chloro 2-methoxyphenyl)urea
N-(2-Hydroxy-4-nitrophenyl) N'-(2-methylphenyl)urea
N-[4-(Benzylamino)carbonyl-2-hydroxyphenyl]-N'-(2-bromophenyl)urea
N-(2-Hydroxy-4-nitrophenyl)-N'-(2-phenoxyphenyl)urea
N-(2-Hydroxy-4-fluorophenyl)-N'-(2-bromophenyl)urea
N-(2-Hydroxy 3-napthyl) N'-(2-bromophenyl)urea;
N-(3,4-Difluoro 2-hydroxyphenyl) N'-(2-bromophenyl)urea
N-(2-Hydroxy 4-phenylphenyl) N'-(2-bromophenyl)urea
N-(2-Hydroxy 4methylphenyl) N'-(2-bromophenyl)urea
N-(2-Hydroxy-4-nitrophenyl) N'-(2-phenylaminophenyl)urea
N-(2-Hydroxy 3-carboxyphenyl) N'-(2-bromophenyl)urea
N-(2-Sulfhydryl 4-bromophenyl) N'-(2-bromophenyl)urea
N-(2-Hydroxy 4-nitrophenyl) N'-(2-iodophenyl)urea
N-(2-Hydroxy 4-nitrophenyl) N'-(2-bromophenyl)thiourea
N-[(2-Phenylsulfamido) 4-cyanophenyl]-N'-(2-bromophenyl)urea
N-(2-(Aminosulfonamidophenyl)phenyl) N'-(2-bromophenyl)urea
N-(2-(Aminosulfonylstyryl)phenyl) N'-(2-bromophenyl)urea
2-[(3,4 Di-methoxyphenylsulfonyl)amino]phenyl) N'-(2-bromophenyl)urea
N-(2-[(4-Acetamidophenylsulfonyl)amino]phenyl) N'-(2-bromophenyl)urea
N-(2-(Aminosulfonyl(2-thiophene)phenyl) N'-(2-bromophenyl)urea
N-(2-(Aminosulfonyl(3-tolyl) phenyl) N'-(2-bromophenyl)urea
N-(2-(Aminosulfonyl(8-quinolinyl))phenyl) N'-(2-bromophenyl)urea
N-(2-(Aminosulfonylbenzyl)phenyl) N'-(2-bromophenyl)urea
N-(2-Hydroxy-4-azidophenyl)-N'-(2-methoxyphenyl)urea
N-[2-Hydroxy-5-cyanophenyl]-N'-[2-bromophenyl]urea
N-[2-Hydroxy-3-fluorophenyl]-N'-[2-bromophenyl]urea
N-[2-Hydroxy-3-fluoro-5-bromophenyl]-N'-[2-bromophenyl]urea
N-[2-Hydroxy-3-chlorophenyl]-N'-[2-bromophenyl]urea
N-[2-Hydroxy-3-trifluoromethylphenyl]-N'-[2-bromophenyl]urea
N-[2-Hydroxy-3,4-diphenyl-phenyl]-N'-[2-bromophenyl]urea
N-[2-Hydroxy-3-glycinemethylestercarbonylphenyl]-N'-[2-bromophenyl]urea
N-[2-Hydroxy-3-glycincarbonylphenyl]-N'-[2-bromophenyl]urea
N-[2-Hydroxy-3,5-dichlorophenyl]-N'-[2-bromophenyl]urea
N-[2-Hydroxy-3-nitrophenyl]-N'-[2-bromophenyl]urea
N-[2-Hydroxy-3,4-dichlorophenyl]-N'-[2-bromophenyl]urea
N-[2-Hydroxy-3-cyanophenyl]-N'-[2-bromophenyl]urea
N-[2-Hydroxy-4-cyanophenyl]-N'-[2-bromophenyl]urea
N-[2-Hydroxy-4-cyanophenyl]-N'-[4-methoxyphenyl]urea
N-[2-Hydroxy-4-cyanophenyl]-N'-[2-phenylphenyl]urea
N-[2-Hydroxy-4-cyanophenyl]-N'-[2-methylphenyl]urea
N-[2-Hydroxy-4-cyanophenyl]-N'-[2-trifluoromethylpheny]urea
N-[2-Hydroxy-4-cyanophenyl]-N'-[3-trifluoromethylphenyl]urea
N-[2-Hydroxy-4-cyanophenyl]-N'-[4-trifluoromethylphenyl]urea
N-[2-Hydroxy-3-n-propylphenyl]-N'-[2-bromophenyl]urea
N-[2-Hydroxy-4-ethylphenyl]-N'-[2-bromophenyl]urea
N-[2-Hydroxy-3-pheylaminocarbonylphenyl]-N'-[2-bromophenyl]urea
N-[2-Hydroxy-3-cyano-4-methylphenyl]-N'-[2-bromophenyl]urea
N-[2-Hydroxy-4-carbophenylphenyl]-N'-[2-bromophenyl]urea
N-[2-Hydroxy-3-carbophenylphenyl]-N'-[2-bromophenyl]urea
N-[3-Benzyloxy-2-hydroxyphenyl]-N'-[2-bromophenyl]urea
(E)-N-[4-[2-(Methoxycarbonyl)ethenyl]-2-hydroxyphenyl]-N'-[2-bromophenyl]urea
(E)-N-[3-[2-(Methoxycarbonyl)ethenyl]-2-hydroxypheny]-N'-[2-bromophenyl]urea-N'-[2-bromophenyl]urea
(E)-N-[3-[2-(Aminocarbonyl)ethenyl]-2-hydroxyphenyl]-N'-[2-bromophenyl]urea-N'-[2-bromophenyl]urea
(E)-N-[4-[2-(Aminocarbonyl)ethenyl]-2-hydroxyphenyl]-N'-[2-bromophenyl]urea-N'-[2-bromophenyl]urea
N-[2-Hydroxy-4-benzamidephenyl]-N'-[2-bromophenyl]urea
N-[4-Aminocarbonyl-2-hydroxyphenyl]-N'-[2-bromophenyl]urea
N-(2-Hydroxy-3,5,6-trifluorophenyl)-N'-(2-bromophenyl)urea
N-(2-Hydroxy-3-fluoro-4-trifuoromethylphenyl)-N'-(2-bromophenyl)urea
N-(2-Hydroxy-3-iodophenyl)-N'-(2-bromophenyl)urea
N-[2-[[[2-(Trifluoromethyl)phenyl]sulfonyl]amino]phenyl]-N'-(2-brouiophenyl)urea
N-(2-Bromophenyl)-N'-[2-dimethylaminosulfonylamino]phenyl]urea
N-[2-(Phenethylsulfonylamino)phenyl]-N'-(2-bromophenyl)urea
N-[2-[(2-Acetamido-4-methylthiazol-5-yl)sulfonylamino]phenyl]-N'-(2-bromophenyl)urea
N-[2-Hydroxy-4-cyanophenyl]-N'-[4-phenylphenyl]urea
N-[2-Hydroxy-4-cyanophenyl]-N'-[2,3-dichlorophenyl]urea N-[2-Hydroxy-4-cyanophenyl]-N'-[2-methoxyphenyl]urea
N-[2-Hydroxy-4-cyanophenyl]-N'-[3-methoxyphenyl]urea
N-[2-Hydroxy-5-fluorophenyl]-N'-[2-bromophenyl]urea
N-[2-Hydroxy-5-trifluoromethylphenyl]-N'-[2-bromophenyl]urea
N-[2-Hydroxyphenyl]-N'-[2-bromophenyl]urea
N-[Trans-3-styrl-2-hydroxyphenyl]-N'-[2-bromophenyl]urea
N-[2-Hydroxy-3,4-dichlorophenyl]-N'-[2-methoxyphenyl]urea
N-[2-Hydroxy-3,4-dichlorophenyl]-N'-[4-methoxyphenyl]urea
N-[2-Hydroxy-3,4-dichlorophenyl]-N'-[3-trifluoromethylphenyl]urea
N-[2-Hydroxy-3,4-dichlorophenyl]-N'-[2-phenylphenyl]urea
N-[2-Hydroxy-3,4-dichlorophenyl]-N'-[4-phenylphenyl]urea
N-[2-Hydroxy-3,4-dichlorophenyl]-N'-[2,3-dichlorophenyl]urea
N-[2-Hydroxy-4-isopropylphenyl]-N'-[3-trifluoromethylphenyl]urea
N-[2-Hydroxy-3-naphthyl]-N'-[2,3-dichlorophenyl]urea
N-[2-[(2,3-Dichlorothien-5-yl)]sulfonylamino]phenyl]-N'-(2-bromophenyl)urea
N-[2-[(3,5-Bistrifluoromethylphenyl)sulfonylamino]phenyl]-N'-(2-bromophenyl)urea
N-[2-[(2-Benzyl)sulfonylamino]-(5-trifluoromethyl)phenyl]-N'-(2-bromophenyl)urea
N-[2-[2-(3-Nitrophenyl)sulfonylamino]phenyl]-N'-(2-bromophenyl)urea
N-[2-[2-(4-Phenoxyphenyl)sulfonylamino]phenyl]-N'-(2-bromophenyl)urea
N-[[2-(1S)-10-Camphorsulfonylamino]phenyl]-N'-(2-bromophenyl)urea
N-[[2-(1R)-10-Camphorsulfonylamino]phenyl]-N'-(2-bromophenyl)urea
N-[2-[2-(2-Nitro-(4-trifluoromethyl)phenyl)sulfonylamino]phenyl-N'-(2-bromophenyl)urea
N-(2-Hydroxy-4-azidophenyl)-N'-(2-iodophenyl)urea
N-(2-Hydroxy-3-azidophenyl)-N'-(2-bromophenyl)urea
N-[2-Hydroxy-3-cyanophenyl]-N'-[2-methoxyphenyl]urea
N-[2-Hydroxy-3-cyanophenyl]-N'-[3-trifluoromethylphenyl]urea
N-[2-Hydroxy-3-cyanophenyl]-N'-[2-phenylphenyl]urea
N-[2-Hydroxy-3-cyanophenyl]-N'-[2,3-dichlorophenyl]urea
N-[2-Hydroxy-4-isopropylphenyl]-N'-[2,3-dichlorophenyl]urea
N-[2-Hydroxy-4-isopropylphenyl]-N'-[2chloro-5-trifluoromethylphenyl]urea
N-[2-Hydroxy-3-phenylphenyl]-N'-[2,3-dichlorophenyl]urea
N-[2-Hydroxy-5-nitrophenyl]-N'-[2-methoxyphenyl]urea
N-[2-Hydroxy-5-nitrophenyl]-N'-[3-trifluoromethylphenyl]urea
N-[2-Hydroxy-5-nitrophenyl]-N'-[2-phenylphenyl]urea
N-[2-Hydroxy-5-nitrophenyl]-N'-[2,3-dichlorophenyl]urea
N-[2-Hydroxy-5-ethylsulfonylphenyl]-N'-[2,3-dichlorophenyl]urea
N-[2-(2-Amino-(4-trifluoromethyl)phenyl)sulfonylamino]phenyl]-N'-(2-bromophenyl)urea
N-[2-(Aminosulfonylphenyl) 3-aminophenyl] N'-(2-bromophenyl)urea
N-[2-Hydroxy-3,4-dichlorophenyl]-N'-[2,4 dimethoxyphenyl]urea
N-[2-Hydroxy-3,4-dichlorophenyl]-N'-[2-chloro-5-trifluoromethylphenyl]urea
N-[2-Hydroxy-3-naphthyl]-N'-[3-trifluoromethylphenyl]urea
N-[2-Hydroxy-5-naphthalenesulfonic acid]-N'-[2-bromophenyl]urea;
N-[2-Hydroxy-naphthalenesulfonic acid]-N'-[2-bromophenyl]urea;
1,1'-(4-Methyl-2-phenylene)bis[2-thio-3-3-tolylurea]
N-(2-Carboxyphenyl)-N'-phenylurea
N-(2-Hydroxy-4-nitrophenyl)-N'-phenylurea;
1-(2-Carboxyphenyl)-3-(4-chlorophenyl)urea;
2-(3,4-Dichlorophenylcarbonyldiimino)-5-trifluoromethylbenzoic acid;
2-(4-Chlorophenylcarbonyldiimino)-5-trifluoromethylbenzoic acid;
1-(p-Anisyl)-3-(2-carboxyphenyl)urea;
1-(2-Carboxyphenyl)-3-(3-fluorophenyl)urea;
1-(2-Carboxyphenyl)-3-(3-chlorophenyl)urea;
1-(m-Anisyl)-3-(2-arboxyphneyl)urea;
1-(o-Anisyl)-3-(2-carboxyphenyl)urea;
1-(2-Carboxyphenyl)-3-(3,4-dichlorophenyl)urea;
1-(2-Carboxyphenyl)-3-(2,4-dichlorophenyl)urea;
N-(5-Chloro-2-hydroxy-4-nitrophenyl)-N'-phenylurea;
N-(2-Hydroxy-4-nitrophenyl)-N'-(4-nitrophenyl)urea;
Prefered compounds of Formula (I) include:
N-(2-Hydroxy-4-nitrophenyl)-N'-(2-methoxyphenyl)urea
N-(2-Hydroxy-4-nitrophenyl)-N'-(2-bromophenyl)urea
N-(2-Hydroxy-4-nitrophenyl)-N'-(2-phenylphenyl)urea
N-(2-Hydroxy-4-nitrophenyl)-N'-(2-methylthiophenyl)urea
N-(2-Hydroxy-4-nitrophenyl)-N'-(2,3-dichlorophenyl)urea
N-(2-hydroxy 4-nitrophenyl) N'-(2-chlorophenyl)urea
N-(2-Hydroxy-4-nitrophenyl)-N'-(2,3-methylenedioxyphenyl)urea
N-(2-Hydroxy-4-nitrophenyl)-N'-(2-methoxy-3-chlorophenyl)urea
N-(2-hydroxy 4-nitrophenyl) N'-(2-phenyloxyphenyl)urea
N-(3-Chloro-2-hydroxyphenyl)-N'-(bromophenyl)urea
N-(2-Hydroxy-3-glycinemethylestercarbonylphenyl)-N'-(2-bromophenyl)urea
N-(3-Nitro-2-hydroxyphenyl)-N'-(2-bromophenyl)urea
N-(2-Hydroxy-4-cyanophenyl)-N'-(2-bromophenyl)urea
N-(2-Hydroxy-3,4-dichlorophenyl)-N'-(2-bromophenyl)urea
N-(3-Cyano-2-hydroxyphenyl)-N'-(2-bromophenyl)urea
N-(2-Hydroxy-4-cyanophenyl)-N'-(2-methoxyphenyl)urea
N-(2-Hydroxy-4-cyanophenyl)-N'-(2-phenylphenyl)urea
N-(2-Hydorxy-4-cyanophenyl-N'-(2,3-dichlorophenyl)urea
N-(2-Hydroxy-4-cyanophenyl)-N'-(2-methylphenyl)urea
N-(2-Hydroxy-3-cyano-4-methylphenyl)-N'-(2-bromophenyl)urea
N-(4-Cyano-2-hydroxyphenyl)-N'-(2-trifluoromethylphenyl)urea
N-(3-Trifluoromethyl-2-hydroxyphenyl)-N'-(2-bromophenyl)urea
N-(3-Phenylaminocarbonyl-2-hydroxyphenyl)-N'-(2-bromophenyl)urea
N-(2-hydroxy 4-nitrophenyl) N'-(2-iodophenyl)urea
N-(2-hydroxy 4-nitrophenyl) N'(2-bromophenyl)thiourea
N-(2-phenylsulfonamido)-cyanophenyl-N'(2-bromophenyl)urea
(E)-N-[3-[(2-Aminocarbonyl)ethenyl]-2-hydroxyphenyl]-N'-(2-bromophenyl)urea
N-(2-Hydroxy,3,4-dichlorophenyl)-N'-(2-methoxyphenyl)urea
N-(2-Hydroxy,3,4-dichlorophenyl)-N'-(2-phenylphenyl)urea
N-(2-Hydroxy-3,4-dichlorophenyl)-N'-(2,3-dichlorophenyl)urea N-(2-Hydroxy-5-nitrophenyl)-N'-(2,3-dichlorophenyl)urea
N-(2-Hydroxy-3-cyanophenyl)-N'-(2,3 dichlorophenyl)urea As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_4R_5$ group; $NHC(O)R_4$; $C(O)NR_4R_5$; $C(O)OH$; $S(O)_2NR_4R_5$; $NHS(O)_2$ $R_{13}$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocylicalkyl, optionally substituted heteroaryl, optionally substituted heteroaryl alkyl, wherein these aryl, hetroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted amino, such as in the $NR_4R_5$ group; $C_{1-10}$ alkyl, or halosubstituted $C_{1-10}$ alkyl, such as $CF_3$.

$R_{13}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl.

Another aspect of the present invention are the novel compounds of Formula (II), or a pharmaceutically acceptable salt thereof, as described below, which are also useful in inhibiting the binding of IL-8 to its receptors in a mammal in need thereof. This invention also relates to the pharmaceutical compositions comprising a compound of Formula (II) and a pharmaceutically acceptable diluent or carrier. Compounds of Formula (II) are also useful for treating a chemokine mediated disease, wherein the chemokine is one which binds to an IL-8 α or β receptor and which method comprises administering an effective amount of a compound of Formula (II) or a pharmaceutically acceptable salt thereof. Compounds of Formula (II) are represented by the structure:

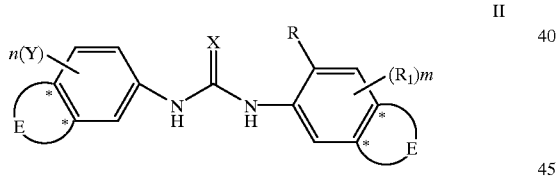

II wherein
X is oxygen or sulfur;
R is any functional moiety having an ionizable hydrogen and a pKa of 10 or less;
$R_1$ is independently selected from hydrogen; halogen; nitro; cyano; halosubstituted $C_{1-10}$ alkyl; $C_{1-10}$ allyl; $C_{2-10}$ alkenyl; $C_{1-10}$ alkoxy; halosubstituted $C_{1-10}$ alkoxy; azide; $S(O)_tR_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heterocyclic, heterocyclic$C_{1-4}$ alkyl; heteroaryl$C_{1-4}$ alkyloxy; aryl $C_{2-10}$ alkenyl; heteroaryl $C_{2-10}$ alkenyl; heterocyclic$C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)_{12}$; $OC(O)R_{11}$; $NR_4C(O)R_{11}$; or two $R_1$ moieties together may form $O-(CH_2)_sO-$ or a 5 to 6 membered unsaturated ring;
t is 0, or an integer having a value of 1 or 2;
s is an integer having a value of 1 to 3;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heteroaryl$C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two Y moieties together may form $O-(CH_2)_sO-$ or a 5 to 6 membered unsaturated ring;

n is an integer having a value of 1 to 3;
m is an integer having a value of 1 to 3;
$R_8$ is hydrogen or $C_{1-4}$ alkyl;
$R_{10}$ is $C_{1-10}$ alkyl $C(O)_2R_8$;
$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$ alkyl, optionally substituted heterocyclic, or optionally substituted heterocyclic$C_{1-4}$alkyl;
$R_{12}$ is hydrogen, $C_{1-10}$ alkyl, optionally substituted aryl or optionally substituted arylalkyl;
E is optionally selected from

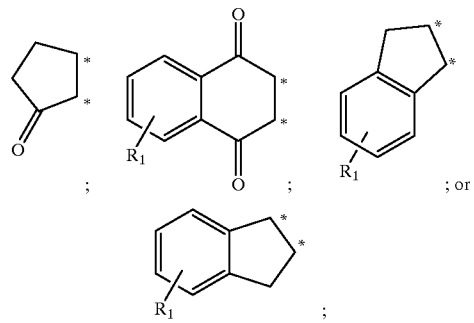

the asterix * denoting point of attachment of the ring, with at least one E being present;
or a pharmaceutically acceptable salt thereof.

Suitably, the variables for Formula (II), such as X, R, $R_1$, $R_4$, $R_5$, $R_6$, $R_7$, $R_8$, $R_9$, Y, $R_a$, $R_b$, $R_c$, n, m, and s terms, etc. are as defined in Formula (I) above. The E ring denoted by its point of attachment through the asterix (*) may optionally be present. If it is not present the ring is a phenyl moiety which is substituted by the R and $R_1$ terms as shown. At least one E ring is necessary. The E ring may be substituted by the $R_1$ moiety in any ring, saturated or unsaturated, and is shown for purposes herein substituted only in the unsaturated ring(s).

Exemplified compounds of Formula (III) are
N-[2-hydroxy-5-indanone]-N'-[2-bromophenyl]urea;
N-[1-hydroxyfluorene]-N'-[2-bromophenyl]urea;

N-[3-hydroxy-9,10-anthraquinon-2-yl]-N'-[2-bromophenyl]urea

Another aspect of the present invention are the novel compounds of Formula (III), or a pharmaceutically acceptable salt thereof, as described below, which are also useful in inhibiting the binding of IL-8 to its receptors in a mammal in need thereof. This invention also relates to the pharmaceutical compositions comprising a compound of Formula (II) and a pharmaceutically acceptable diluent or carrier. Compounds of Formula (III) are also useful for treating a chemokine mediated disease, wherein the chemokine is one which binds to an IL-8 α or β receptor and which method comprises administering an effective amount of a compound of Formula (III) or a pharmaceutically acceptable salt thereof. Compounds of Formula (III) are represented by the formula:

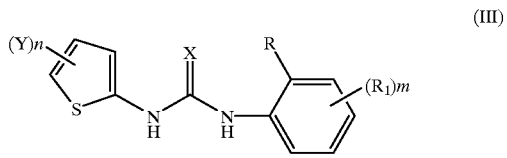

(III)

wherein

X is oxygen or sulfur;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_t R_4$; hydroxy; hydroxy$C_{1-4}$ alkyl; aryl; aryl $C_{1-4}$ alkyl; aryloxy; aryl$C_{1-4}$ alkyloxy; heteroaryl; heteroarylalkyl; heterocyclic, heterocyclic$C_{1-4}$ alkyl; heteroaryl$C_{1-4}$ alkyloxy; aryl $C_{2-10}$ alkenyl; heteroaryl $C_{2-10}$ alkenyl; heterocyclic$C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two $R_1$ moieties together may form O—$(CH_2)_s$O— or a 5 to 6 membered unsaturated ring;

t is 0, or an integer having a value of 1 or 2;

s is an integer having a value of 1 to 3;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_t R_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl$C_{1-4}$ alkyloxy; heterocyclic, heterocyclic$C_{1-4}$alkyl; aryl $C_{2-10}$ alkenyl; heteroaryl $C_{2-10}$ alkenyl; heterocyclic$C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two Y moieties together may form O—$(CH_2)_s$O— or a 5 to 6 membered unsaturated ring;

n is an integer having a value of 1 to 3;

m is an integer having a value of 1 to 3;

$R_8$ is hydrogen or $C_{1-4}$ alkyl;

$R_{10}$ is $C_{1-10}$ alklyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$ alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

or a pharmaceutically acceptable salt thereof.

Suitably, the variables, etc. for Formula (II) are the same as those defined for Formula (I) above, such as for example the R variable.

Exemplified compounds of Formula (III) are N-(2-Hydroxy-4-nitrophenyl)-N'-(3-methoxy-2-thienyl)urea; and N-(2-hydroxy-5-nitrophenyl)-N'-(3-methoxy-2-thienyl)urea.

Another aspect of the present invention is the novel compounds of Formula (Ia), a subset of compounds of Formula (I) useful for treating a chemokine mediated disease as defined herein. This invention also relates to the pharmaceutical compositions comprising a compound of Formula (Ia) and a pharmaceutically acceptable diluent or carrier. The compounds of Formula (Ia) are represented by the structure:

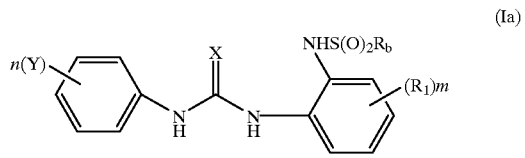

(Ia)

wherein

X is oxygen or sulfur;

$R_a$ is an alkyl, aryl, aryl$C_{1-4}$alkyl, heteroaryl, heteroaryl $C_{1-4}$alkyl, heterocyclic, or a heterocyclic $C_{1-4}$alkyl moiety, all of which may be optionally substituted;

$R_b$ is a $NR_6R_7$, alkyl, aryl, aryl$C_{1-4}$alkyl, aryl $C_{2-4}$alkenyl, heteroaryl, heteroaryl$C_{1-4}$alkyl, heteroaryl$C_{2-4}$ alkenyl, heterocyclic, or heterocyclic $C_{1-4}$alkyl, or a heterocyclic $C_{2-4}$alkenyl moiety, camphor, all of which may be optionally substituted one to three times independently by halogen; nitro; halosubstituted $C_{1-4}$ alkyl; $C_{1-4}$ alkyl; $C_{1-4}$ alkoxy; $NR_9C(O)R_a$; $C(O)NR_6R_7$, $S(O)_3H$, or $C(O)OC_{1-4}$ alkyl;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur, which ring may be optionally substitued;

$R_9$ is hydrogen or a $C_{1-4}$ alkyl, preferably hydrogen;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_t R_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl;

heteroaryl $C_{2-10}$ alkenyl; heterocyclic$C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two $R_1$ moieties together may form $O—(CH_2)_sO—$ or a 5 to 6 membered unsaturated ring;

t is 0, or an integer having a value of 1 or 2;

s is an integer having a value of 1 to 3.

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl$C_{1-4}$ alkyloxy; heterocyclic, heterocyclic$C_{1-4}$alkyl; aryl $C_{2-10}$ alkenyl; heteroaryl $C_{2-10}$ alkenyl; heterocyclic$C_{2-10}$ alkenyl; $NR_4R_5$; $C_{2-10}$ alkenyl $C(O)NR_4R_5$; $C(O)NR_4R_5$; $C(O)NR_4R_{10}$; $S(O)_3H$; $S(O)_3R_8$; $C_{1-10}$ alkyl $C(O)R_{11}$; $C_{2-10}$ alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two Y moieties together may form $O—(CH_2)_sO—$ or a 5 to 6 membered unsaturated ring;

is an integer having a value of 1 to 3, m is an integer having a value of 1 to 3;

$R_8$ is hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$ alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

or a pharmaceutically acceptable salt thereof.

A preferred ring substitution for $R_1$ variable is monosubstituted in the 3-position, or the 4-position, or di-substituted in the 3,4-position. The substituent group is suitably an electron withdrawing moiety. Preferably $R_1$ is nitro, halogen, cyano, trifluoromethyl group, or $C(O)NR_4R_5$.

While Y may be substituted in any of the 5 ring positions, preferably the ring with the Y moiety is mono-substituted in the 2-position or 3-position, with the 4- preferably being unsubstituted. If the ring is di-substituted, substituents are preferably in the 2'-, 3'-positions of a monocyclic ring. While both $R_1$ and Y can both be hydrogen, it is prefered that at least one of the rings be substituted, preferably both rings are at least mono-substituted, i.e. n amd m are each equal to 1 or more.

Y is more preferably a mono-substituted halogen, disubstituted halogen, mono-substituted alkoxy, disubstituted alkoxy, methylenedioxy, aryl, or alkyl, preferably these groups are substituted in the 2'-position or 2'-,3'-position.

Exemplified compounds of Formula (Ia) are
N-(4-Nitro 2-(phenylsulfonylamino)phenyl)-N'-phenylurea
N-[(2-Phenylsulfamido) 4-cyanophenyl]-N'-(2-bromophenyl)urea
N-(2-(Aminosulfonamidophenyl)phenyl) N'-(2-bromophenyl)urea
N-(2-(Aminosulfonylstyryl)phenyl) N'-(2-bromophenyl)urea
2-[(3,4 Di-methoxyphenylsulfonyl)amino]phenyl) N'-(2-bromophenyl)urea
N-(2-[(4-Acetamidophenylsulfonyl)amino]phenyl) N'-(2-bromophenyl)urea
N-(2-(Aminosulfonyl(2-thiophene)phenyl) N'-(2-bromophenyl)urea
N-(2-(Aminosulfonyl(3-tolyl)phenyl) N'-(2-bromophenyl)urea
N-(2-(Aminosulfonyl(8-quinolinyl))phenyl) N'-(2-bromophenyl)urea
N-(2-(Aminosulfonylbenzyl)phenyl) N'-(2-bromophenyl)urea
N-[2-[[[2-(Trifluoromethyl)phenyl]sulfonyl]amino]phenyl]-N'-(2-bromophenyl)urea
N-(2-Bromophenyl)-N'-[2-dimethylaminosulfonylamino]phenyl]urea
N-[2-(Phenethylsulfonylamino)phenyl]-N'-(2-bromophenyl)urea
N-[2-[(2-Acetamido-4-methylthiazol-5-yl)sulfonylaminolphenyl]-N'-(2-bromophenyl)urea
N-[2-[(2,3-Dichlorothien-5-yl)]sulfonylamino]phenyl]-N'-(2-bromophenyl)urea
N-[2-[(3,5-Bistrifluoromethiylphenyl)sulfonylamino]phenyl]-N'-(2-bromophenyl)urea
N-[2-[(2-Benzyl)sulfonylamino]-(5-trifluoromethyl)phenyl]-N'-(2-bromophenyl)urea
N-[2-[2-(3-Nitrophenyl)sulfonylamino]phenyl]-N'-(2-bromophenyl)urea
N-[2-[2-(4-Phenoxyphenyl)sulfonylamino]phenyl]-N'-(2-bromophenyl)urea
N-[[2-(1S)-10-Camphorsulfonylamino]phenyl]-N'-(2-bromophenyl)urea
N-[[2-(1R)-10-Camphorsulfonylamino]phenyl]-N'-(2-bromophenyl)urea
N-[2-[2-(2-Nitro-(4-fluoromethyl)phenyl)sulfonylamino]phenyl-N'-(2-bromophenyl)urea
N-[2-(2-Amino-(4-trifluoromethyl)phenyl)sulfonylamino]phenyl]-N'-(2-bromophenyl)urea
N-[2-(aminosulfonylphenyl)3-aminophenyl]N'-(2-bromophenyl)urea Another aspect of the present invention is the novel compounds of Formula (Ib), a subset of compounds of Formula (I) useful for treating a chemokine mediated disease. This invention also relates to the pharmaceutical compositions comprising a compound of Formula (Ib) and a pharmaceutically acceptable diluent or carrier. The compounds of Formula (Ib) are represented by the strucuture:

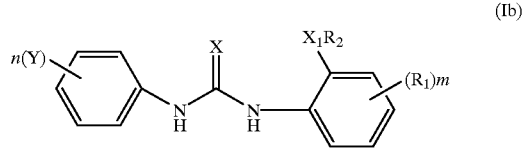

(Ib)

wherein
X is oxygen or sulfur;
$X_1$ is oxygen or sulfur;
$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy$C_{1-4}$alky;

aryl; aryl C$_{1-4}$ alkyl; aryloxy; arylC$_{1-4}$ alkyloxy; heteroaryl; heteroarylalkyl; heterocyclic, heterocyclic C$_{1-4}$alkyl; heteroaryl C$_{1-4}$ alkyloxy; aryl C$_{2-10}$ alkenyl; heteroaryl C$_{2-10}$ alkenyl; heterocyclicC$_{2-10}$ alkenyl; NR$_4$R$_5$; C$_{2-10}$ alkenyl C(O)NR$_4$R$_5$; C(O)NR$_4$R$_5$; C(O)NR$_4$R$_{10}$; S(O)$_3$H; S(O)$_3$R$_8$; C$_{1-10}$ alkyl C(O)R$_{11}$; C$_{2-10}$ alkenyl C(O)R$_{11}$; C$_{2-10}$ alkenyl C(O)OR$_{11}$; C(O)R$_{11}$; C(O)OR$_{12}$; OC(O)R$_{11}$; NR$_4$C(O)R$_{11}$; or two R$_1$ moieties together may form O—(CH$_2$)$_s$O— or a 5 to 6 membered unsaturated ring;

t is 0, or an integer having a value of 1 or 2;

s is an integer having a value of 1 to 3;

R$_2$ is a substituted aryl, heteroaryl, or heterocyclic ring which ring has a functional moiety providing the ionizable hydrogen having a pKa of 10 or less;

R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$alkyl, heterocyclic, heterocyclicC$_{1-4}$ alkyl, or R$_4$ and R$_5$ together with the nitrogen to which they are attached form a 5 to 7 member ring which may optionally comprise an additional heteroatom selected from O/N/S;

Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; S(O)$_t$R$_4$; hydroxy; hydroxyC$_{1-4}$alkyl; aryl; aryl C$_{1-4}$ alkyl; aryloxy; arylC$_{1-4}$ alkyloxy; heteroaryl; heteroarylalkyl; heteroarylC$_{1-4}$ alkyloxy; heterocyclic, heterocyclicC$_{1-4}$alkyl; aryl C$_{2-10}$ alkenyl; heteroaryl C$_{2-10}$ alkenyl; heterocyclicC$_{2-10}$ alkenyl; NR$_4$R$_5$; C$_{2-10}$ alkenyl C(O)NR$_4$R$_5$; C(O)NR$_4$R$_5$; C(O)NR$_4$R$_{10}$; S(O)$_3$H; S(O)$_3$R$_8$; C$_{1-10}$ alkyl C(O)R$_{11}$; C$_{2-10}$ alkenyl C(O)R$_{11}$; C$_{2-10}$ alkenyl C(O)OR$_{11}$; C(O)R$_{11}$; C(O)OR$_{12}$; OC(O)R$_{11}$; NR$_4$C(O)R$_{11}$; or two Y moieties together may form O—(CH$_2$)$_s$O— or a 5 to 6 membered unsaturated ring;

n is an integer having a value of 1 to 3;

m is an integer having a value of 1 to 3;

R$_8$ is hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, optionally substituted aryl, optionally substituted aryl C$_{1-4}$alkyl, optionally substituted heteroaryl, optionally substituted heteroarylC$_{1-4}$ alkyl, optionally substituted heterocyclic, or optionally substituted heterocyclicC$_{1-4}$alkyl;

R$_{12}$ is hydrogen, C$_{1-10}$ alkyl, optionally substituted aryl or optionally substituted arylalkyl;

or a pharmaceutically acceptable salt thereof.

Suitably, the variable, etc. for Formula (Ib) are the same as those defined for Formula (I) above, such as for example the functional moieties on the R$_2$ group having an ionizable hydrogen with a pKa of 10 or less. Suitably such functional groups include, but are not limited to, hydroxy, carboxylic acid, thiol, —NH—C(O)R$_a$, —C(O)NR$_6$R$_7$, substituted sulfonamides of the formula —NHS(O)$_2$R$_b$, —S(O)$_2$NHR$_c$, NHC(X$_2$)NHR$_b$, or tetrazoyl (as defined for Formula (I).

Suitably for compounds of Formula (Ib), a preferred ring substitution for R$_1$ is in the 3-position, the 4-position or is preferably di substituted in the 3,4-position. The substituent group is suitably an electron withdrawing moiety. Preferably R$_1$ is nitro, halogen, cyano, trifluoromethyl group, or C(O)NR$_4$R$_5$.

While Y may be substituted in any of the 5 ring positions, preferably the ring with the Y moiety is mono-substituted in the 2-position or 3-position, with the 4- preferably being unsubstituted. If the ring is disubstituted, substituents are preferably in the 2' or 3' position of a monocyclic ring. While both R$_1$ and Y can both be hydrogen, it is prefered that at least one of the rings be substituted, preferably both rings are at least mono-substituted, i.e. n amd m are each equal to 1 or more.

Suitably for compounds of Formula (Ib), Y is more preferably disubstituted halogen, mono-substituted halogen, disubstituted alkoxy, mono-substituted alkoxy, methylenedioxy, aryl, or alkyl, preferably in the 2'position or 2',3'-position.

Another aspect of the present invention is the novel compounds of Formula (Ic), a subset of compounds of Formula (I) useful for treating a chemokine mediated disease. This invention also relates to the pharmaceutical compositions comprising a compound of Formula (Ic) and a pharmaceutically acceptable diluent or carrier. The compounds of Formula (Ic) are represented by the strucuture:

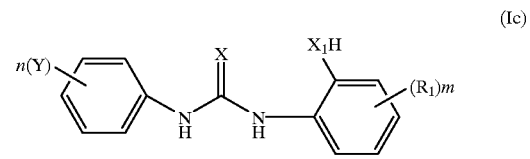

(Ic)

wherein

X is oxygen or sulfur;

X$_1$ is oxygen or sulfur;

R$_1$ is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; S(O)$_t$R$_4$; hydroxy; hydroxyC$_{1-4}$alkyl; aryl; aryl C$_{1-4}$ alkyl; aryloxy; aryl C$_{1-4}$ alkyloxy; heteroaryl; heteroarylalkyl; heterocyclic, heterocyclicC$_{1-4}$ alkyl; heteroarylC$_{1-4}$ alkyloxy; aryl C$_{2-10}$ alkenyl; heteroaryl C$_{2-10}$ alkenyl; heterocyclic C$_{2-10}$ alkenyl; NR$_4$R$_5$; C$_{2-10}$ alkenyl C(O)NR$_4$R$_5$; C(O)NR$_4$R$_5$; C(O)NR$_4$R$_{10}$; S(O)$_3$H; S(O)$_3$R$_8$; C$_{1-10}$ alkyl C(O)R$_{11}$; C$_{2-10}$ alkenyl C(O)R$_{11}$; C$_{2-10}$ alkenyl C(O)OR$_{11}$; C(O)R$_{11}$; C(O)OR$_{12}$; OC(O)R$_{11}$; NR$_4$C(O)R$_{11}$; or two R$_1$ moieties together may form O—(CH$_2$)$_s$O— or a 5 to 6 membered unsaturated ring;

t is 0, or an integer having a value of 1 or 2;

s is an integer having a value of 1 to 3;

R$_4$ and R$_5$ are independently hydrogen, optionally substituted C$_{1-4}$ alkyl, optionally substituted aryl, optionally substituted aryl C$_{1-4}$alkyl, optionally substituted heteroaryl, optionally substituted heteroaryl C$_{1-4}$ alkyl, heterocyclic, heterocyclic C$_{1-4}$ alkyl, or R$_4$ and R$_5$ together with the nitrogen to which they are attached form a 5 to 7 member ring which may optionally comprise an additional heteroatom selected from O/N/S;

Y is independently selected from halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; S(O)$_t$R$_4$; hydroxy; hydroxy C$_{1-4}$alkyl; aryl; aryl C$_{1-4}$ alkyl; aryloxy; arylC$_{1-10}$ alkyloxy; heteroaryl; heteroarylalkyl; heteroarylC$_{1-4}$ alkyloxy; heterocyclic, heterocyclic C$_{1-4}$alkyl; aryl C$_{2-10}$ alkenyl; heteroaryl C$_{2-10}$ alkenyl; heterocyclic C$_{2-10}$ alkenyl; NR$_4$R$_5$; C$_{2-10}$ alkenyl C(O)NR$_4$R$_5$; C(O)NR$_4$R$_5$; C(O)NR$_4$R$_{10}$; S(O)$_3$H; S(O)$_3$R$_8$; C$_{1-10}$ alkyl C(O)R$_{11}$; C$_{2-10}$ alkenyl C(O)R$_{11}$;

$C_{2-10}$ alkenyl $C(O)OR_{11}$; $C(O)R_{11}$; $C(O)OR_{12}$; $OC(O)R_{11}$; $NR_4C(O)R_{11}$; or two Y moieties together may form O—$(CH_2)_sO$— or a 5 to 6 membered unsaturated ring;

n is an integer having a value of 1 to 3;

m is an integer having a value of 1 to 3;

$R_8$ is hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

provided that
when n=1 than Y is substituted in the 2- or 3-position;
when n=2 than Y is di-substituted in the 2'-3'-position, the 2'-5'-position, the 2'-6' position, the 3'-5' or the 3'-6' position;
when b=3 than Y is trisubstituted in the 2'-3'-5' or the 2'-3'-6'-positions;

further provided that
when $X_1$ is O, m=2, $R_1$ is 2-t-butyl, 4-methyl, and n=3 than Y is not 2'-OH,3'-t-butyl, 5'-methyl;
when $X_1$ is O, m=1, $R_1$ is 4-methyl, and n=2 than Y is not 2'-OH, 5-methyl;
when $X_1$ is O, m=1, $R_1$ is hydrogen, and n=2 than Y is not 2'-6'-diethyl;
when $X_1$ is O, m=1, $R_1$ is 6-OH, and n=2 than Y is not 2'-5'-methyl;
when $X_1$ is S, m=1, $R_1$ is 4-ethyl, and n=1 than Y is not 2-methoxy;

or a pharmaceutically acceptably salt thereof.

Suitably, the variables, etc. for Formula (Ic) are the same as those defined for Formula (I) above unless indicated.

Suitably for compounds of Formula (Ic), a preferred ring substitution for $R_1$ is in the 3-position, the 4-position or di substituted in the 3,4-position. Preferably $R_1$ is other than hydrogen. The substituent group is suitably an electron withdrawing moiety. Preferably $R_1$ is nitro, halogen, cyano, trifluoromethyl group, or $C(O)NR_4R_5$.

While Y may be substituted in any of the 5 ring positions, preferably the ring with the Y moiety is mono-substituted in the 2-position or 3-position, with the 4- preferably being unsubstituted. If the ring is disubstituted, substituents are preferably in the 2' or 3' position of a monocyclic ring. While both $R_1$ and Y can both be hydrogen, it is prefered that at least one of the rings be substituted, preferably both rings are at least mono-substituted, i.e. n amd m are each equal to 1 or more.

Suitably for compounds of Formula (Ic), Y is more preferably a mono-substituted halogen, disubstituted halogen, mono-substituted alkoxy, disubstituted alkoxy, methylenedioxy, aryl, or alkyl, preferably with these groups in the 2'position or 2,3-position.

Exemplified compounds of Formula (Ic) are:
N-[2-Hydroxy-4-(methoxycarbonyl)phenyl]-N'-phenylurea;
N-[2-Hydroxy-5-nitro-phenyl]-N'-phenylurea
N-(2-Hydroxy-4-fluorophenyl)-N'-phenylurea
N-[2-Hydroxy-4-(trifluoromethyl)phenyl]-N'-phenylurea
N-(2-Hydroxy-4-nitrophenyl)-N'-(2-hydroxy-4-nitrophenyl)urea
N-(2-Hydroxy-4-nitrophenyl)-N'-phenyl-thiourea
N-(2-Hydroxy-5-nitrophenyl)-N'-(3-methoxy-2-thienyl)urea
N-(2-Hydroxy-5-nitrophenyl)-N'-(3-methoxy-2-thienyl)urea
N-(2-Hydroxy-4-nitrophenyl)-N'-(3-methoxyphenyl)urea
N-(2-Hydroxy-4-nitrophenyl)-N'-(2-methoxyphenyl)urea
N-(2-Hydroxy-4-ntrophenyl)-N'-(3-trifluoromethylphenyl)urea
N-(2-Hydroxy-4-nitrophenyl)-N'-(2-trifluoromethylphenyl)urea
N-(2-Hydroxy-4-nitrophenyl)-N'-(4-trifluoromethylphenyl)urea
N-(2-Hydroxy-4-nitrophenyl)-N'-(2-bromopheny))urea
N-(2-Hydroxy-4-nitrophenyl)-N'-(3-bromophenyl)urea
N-(2-Hydroxy-4-nitrophenyl)-N'-(4-bromophenyl)urea
N-(2-Hydroxy-4-nitrophenyl)-N'-(2-phenylphenyl)urea
N-(2-Hydroxy-4-nitrophenyl)-N'-(2-nitrophenyl)urea
N-(2-Hydroxy-4-nitrophenyl)-N'-(2-fluorophenyl)urea
N-(2-Hydroxy-4-nitrophenyl)-N'-(2,6-difluorophenyl)urea
N-(2-Hydroxy-4-nitrophenyl)-N'-(2-ethoxyphenyl)urea
N-(2-Hydroxy-4-nitrophenyl)-N'-(2-ethylphenyl)urea
N-(2-Hydroxy-4-nitrophenyl)-N'-(2-trifluoromethoxyphenyl)urea
N-(2-Hydroxy-4-nitrophenyl) N'-(2-methylthiophenyl)urea
N-(2-Hydroxy-4-nitro-phenyl) N'-(2-chloro 6-methylphenyl)urea
N-(2-Hydroxy-4-nitro-phenyl) N'-(2-sulfoxymethylphenyl)urea
N-(2-Hydroxy-4-trifluoromethylphenyl)-N'-(2-bromophenyl)urea
N-(2-Hydroxy-4-trifluoromethylphenyl)-N'-(2-phenylphenyl)urea
N-(2-Hydroxy-4-carbomethoxyphenyl)-N'-(2-phenylphenyl)urea
N-(2-Hydroxy-4-nitrophenyl)-N'-(2,3-dichlorophenyl)urea
N-(2-Hydroxy-4-nitrophenyl)-N'-(2,4-dichlorophenyl)urea
N-(2-Hydroxy-4-nitrophenyl)-N'-(2-chlorophenyl)urea
N-(2-Hydroxy-4-nitrophenyl)-N'-(2,4-dibromophenyl)urea
N-(2-Hydroxy-1-napthyl)-N'-(2-bromophenyl)urea
N-(2-Hydroxy-4-nitrophenyl)-N'-(2,3-methylenedioxyphenyl)urea
N-(2-Hydroxy-4-nitrophenyl) N'-(3-chloro 2-methoxyphenyl)urea
N-[2-Hydroxy-4-(Benzylamino)carbonylphenyl]-N'-(2-bromophenyl)urea
N-(2-Hydroxy-4-nitrophenyl)-N'-(2-phenoxyphenyl)urea
N-(2-Hydroxy-4-fluorophenyl)-N'-(2-bromophenyl)urea
N-(2-Hydroxy-3,4-difluorophenyl)-N'-(2-bromophenyl)urea
N-(2-Hydroxy 4-phenylphenyl) N'-(2-bromophenyl)urea
N-(2-Hydroxy 4-methylphenyl)-N'-(2-bromophenyl)urea
N-(2-Hydroxy-4-nitrophenyl)-N'-(2-phenylaminophenyl)urea
N-(2-Hydroxy 3-carboxyphenyl)-N'-(2-bromophenyl)urea
N-(2-Sulfhydryl-4-bromophenyl)-N'-(2-bromophenyl)urea
N-(2-Hydroxy 4-nitrophenyl)-N'-(2-iodophenyl)urea
N-(2-Hydroxy 4-nitrophenyl)-N'-(2-bromophenyl)thiourea
N-(2-Hydroxy-4-azidophenyl)-N'-(2-methoxyphenyl)urea
N-[2-Hydroxy-5-cyanophenyl]-N'-[2-bromophenyl]urea
N-[2-Hydroxy-3-fluorophenyl]-N'-[2-bromophenyl]urea
N-[2-Hydroxy-3-fluoro-5-bromophenyl]-N'-[2-bromophenyl]urea
N-[2-Hydroxy-3-chlorophenyl]-N'-[2-bromophenyl]urea
N-[2-Hydroxy-3-trifluoromethylphenyl]-N'-[2-bromophenyl]urea
N-[2-hydroxy-3,4-diphenylphenyl]-N'-[2-bromophenyl]urea
N-[2-Hydroxy-3-glycinemethylestercarbonylphenyl]-N'-[2-bromophenyl]urea N-[2-Hydroxy-3-glycincarbonylphenyl]-N'-[2-bromophenyl]urea
N-[2-Hydroxy-3,5-dichlorophenyl]-N'-[2-bromophenyl]urea
N-[2-Hydroxy-3-nitrophenyl]-N'-[2-bromophenyl]urea
N-[2-Hydroxy-3,4-dichlorophenyl]-N'-[2-bromophenyl]urea
N-[2-Hydroxy-3-cyanophenyl]-N'-[2-bromophenyl]urea
N-[2-Hydroxy-4-cyanophenyl]-N'-[2-bromophenyl]urea
N-[2-Hydroxy-4-cyanophenyl]-N'-[4-methoxyphenyl]urea
N-[2-Hydroxy-4-cyanophenyl]-N'-[2-phenylphenyl]urea
N-[2-Hydroxy-4-cyanophenyl]-N'-[2-methylphenyl]urea
N-[2-Hydroxy-4-cyanophenyl]-N'-[2-trifluoromethylphenyl]urea
N-[2-Hydroxy-4-cyanophenyl]-N'-[3-trifluoromethylphenyl]urea
N-[2-Hydroxy-4-cyanophenyl]-N'-[4-tifluoromethylphenyl]urea
N-[2-Hydroxy-3-n-propylphenyl]-N'-[2-bromophenyl]urea
N-[2-Hydroxy-4-ethylphenyl]-N'-[2-bromophenyl]urea
N-[2-Hydroxy-3-phenylaminocarbonylphenyl]-N'-[2-bromophenyl]urea
N-[2-Hydroxy-3-cyano-4-methylphenyl]-N'-[2-bromophenyl]urea
N-[2-Hydroxy-4-carbophenylphenyl]-N'-[2-bromophenyl]urea
N-[2-Hydroxy-3-carbophenylphenyl]-N'-[2-bromophenyl]urea
N-[2-Hydroxy-3-benzyloxyphenyl]-N'-[2-bromophenyl]urea
(E)-N-[4-[2-(Methoxycarbonyl)ethenyl]-2-hydroxyphenyl]-N'-[2-bromophenyl]urea
(E)-N-[3-[2-(Methoxycarbonyl)ethenyl]-2-hydroxyphenyl]-N'-[2-bromophenyl]urea-N'-[2-bromophenyl]urea
(E)-N-[3-[2-(Aminocarbonyl)ethenyl]-2-hydroxyphenyl]-N'-[2-bromophenyl]urea-N'-[2-bromophenyl]urea
(E)-N-[4-[2-(Aminocarbonyl)ethenyl]-2-hydroxyphenyl]-N'-[2-bromophenyl]urea-N'-[2-bromophenyl]urea
N-[2-Hydroxy-4-benzamidephenyl]-N'-[2-bromophenyl]urea
N-[2-Hydroxy-4-aminocarbonylphenyl]-N'-[2-bromophenyl]urea
N-(2-Hydroxy-3,5,6-trifluorophenyl)-N'-(2-bromophenyl)urea
N-(2-Hydroxy-3-fluoro-4-trifluoromethylphenyl)-N'-(2-bromophenyl)urea
N-(2-Hydroxy-3-iodophenyl)-N'-(2-bromophenyl)urea
N-[2-Hydroxy-4-cyanophenyl]-N'-[4-phenylphenyl]urea
N-[2-Hydroxy-4-cyanophenyl]-N'-[2,3-dichlorophenyl]urea
N-[2-Hydroxy-4-cyanophenyl]-N'-[2-methoxyphenyl]urea
N-[2-Hydroxy-4-cyanophenyl]-N'-[3-methoxyphenyl]urea
N-[2-Hydroxy-5-fluorophenyl]-N'-[2-bromophenyl]urea
N-[2-Hydroxy-5-trifluoromethylphenyl]-N'-[2-bromophenyl]urea
N-[2-Hydroxyphenyl]-N'-[2-bromophenyl]urea
N-[Trans-3-styrl-2-hydroxyphenyl]-N'-[2-bromophenyl]urea
N-[2-Hydroxy-3,4-dichlorophenyl]-N'-[2-methoxyphenyl]urea
N-[2-Hydroxy-3,4-dichlorophenyl]-N'-[4-methoxyphenyl]urea
N-[2-Hydroxy-3,4-dichlorophenyl]-N'-[3-trifluoromethylphenyl]urea
N-[2-Hydroxy-3,4-dichlorophenyl]-N'-[2-phenylphenyl]urea
N-[2-Hydroxy-3,4-dichlorophenyl]-N'-[4-phenylphenyl]urea
N-[2-Hydroxy-3,4-dichlorophenyl]-N'-[2,3-dichlorophenyl]urea
N-[2-Hydroxy-4-isopropylphenyl]-N'-[3-trifluoromethylphenyl]urea
N-[2-Hydroxy-3-naphthyl]-N'-[2,3-dichlorophenyl]urea
N-(2-Hydroxy-4-azidophenyl)-N'-(2-iodophenyl)urea
N-(2-Hydroxy-3-azidophenyl)-N'-(2-bromophenyl)urea
N-[2-Hydroxy-3-cyanophenyl]-N'-[2-methoxyphenyl]urea
N-[2-Hydroxy-3-cyanophenyl]-N'-[3-trifluoromethylphenyl]urea
N-[2-Hydroxy-3-cyanophenyl]-N'-[2-phenylphenyl]urea
N-[2-Hydroxy-3-cyanophenyl]-N'-[2,3-dichlorophenyl]urea
N-[2-Hydroxy-4-isopropylphenyl]-N'-[2,3-dichlorophenyl]urea
N-[2-Hydroxy-4-isopropylphenyl]-N'-[2-chloro-5-trifluoromethylphenyl]urea
N-[2-Hydroxy-3-phenylphenyl]-N'-[2,3-dichlorophenyl]urea
N-[2-Hydroxy-5-nitrophenyl]-N'-[2-methoxyphenyl]urea
N-[2-Hydroxy-5-nitrophenyl]-N'-[3-trifluoromethylphenyl]urea
N-[2-Hydroxy-5-nitrophenyl]-N'-[2-phenylphenyl]urea
N-[2-Hydroxy-5-nitrophenyl]-N'-[2,3-dichlorophenyl]urea
N-[2-Hydroxy-5-ethylsulfonylphenyl]-N'-[2,3-dichlorophenyl]urea
N-[2-Hydroxy-3,4dichlorophenyl]-N'-[2,4 dimethoxyphenyl]urea
N-[2-Hydroxy-3,4-dichlorophenyl]-N'-[2-chloro-5-trifluoromethylphenyl]urea
N-[2-Hydroxy-3,4-dichlorophenyl]-N'-[benzyl]urea
N-[2-Hydroxy-4-isopropylphenyl]-N'-[3-trifluoromethylphenyl]urea
N-[2-Hydroxy-3-naphthyl]-N'-[3-trifluoromethylphenyl]urea
N-[2-Hydroxy-3-naphthyl]-N'-[2,3-dichlorophenyl]urea
N-[2-Hydroxy-3-naphthyl]-N'-[benzyl]urea
N-[2-hydroxy-3-(phenylaminocarbonyl)phenyl]-N'-[benzoyl]urea
N-[2-Hydroxy-3-trifluoromethylphenyl]-N'-[benzoyl]urea
N-[2-Hydroxy-4-cyanophenyl]-N'-[benzoyl]urea
N-[2-Hydroxy-5-naphthalenesulfonic acid]-N'-[2-bromophenyl]urea;
N-[2-Hydroxy-4-naphthalenesulfonic acid]-N'-[2-bromophenyl]urea;
N-(2-Hydroxy 3-napthyl) N'-(2-bromophenyl)urea;
N-(2-Hydroxy-1-napthyl)-N'-(2-bromophenyl)urea;
N-(2-Hydroxy-4-nitrophenyl)-N'-(1-naphthyl)urea;

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:
"halo"—all halogens, that is chloro, fluoro, bromo and iodo.
"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl" refers to the fully oxidized $S(O)_2$ moiety.

The term "wherein two $R_1$ moieties (or two Y moieties) may together form a 5 or 6 membered unsaturated ring" is used herein to mean the formation of a napthylene ring system or a phenyl moiety having attached a 6 membered partially unsaturated ring such as a $C_6$ cycloalkenyl, i.e hexene, or a $C_5$ cyloalkenyl moiety, cyclopentene.

The compounds of Formula (I), (Ia), (Ib), (Ic), (II) and (III) may be obtained by applying synthetic procedures, some of which are illustrated in the Schemes below. The synthesis provided for in these Schemes is applicable for the producing compounds of Formula (I), (Ia), (II) and (III) having a variety of different R, $R_1$, and Ar groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art. While the schemes are shown with compounds only of Formula (I) this is merely for illustration purposes only.

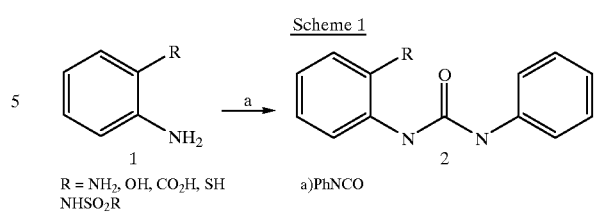

$R = NH_2, OH, CO_2H, SH$
$NHSO_2R$ a)PhNCO

Ortho substituted phenylureas shown in 2-scheme 1 may be prepared by standard conditions involving the condensation of commercially available ortho substituted aniline (Aldrich Chemical Co., Milwaukee, Wis.) with the commercially available optionally substituted aryl isocyanate (Aldrich Chemical Co., Milwaukee, Wis.) in an aprotic solvent (DMF, toluene). When the 1-($RSO_2NH$)2-($NH_2$)Ph is not commercially available it can be made by treating the commercially available $RSO_2Cl$ with the cooresponding 2-phenylene diamine in the presence of an base like triethyl amine or NaH in an aprotic solvent (like methylene chloride or DMF).

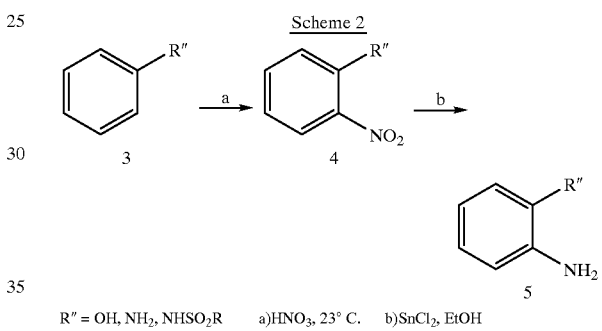

R″ = OH, $NH_2$, $NHSO_2R$   a)$HNO_3$, 23° C.   b)$SnCl_2$, EtOH

If the desired 2-substituted aniline 5-scheme 2, is not commercially available the corresponding nitro compound can be prepared from 3-scheme 2, under standard nitration conditions (using $HNO_3$ or $BF_4NO_3$) at 23° C. The nitro compound is then reduced to the corresponding aniline using $SnCl_2$ in EtOH (or alternately $H_2$/Pd or $LiAlH_4$).

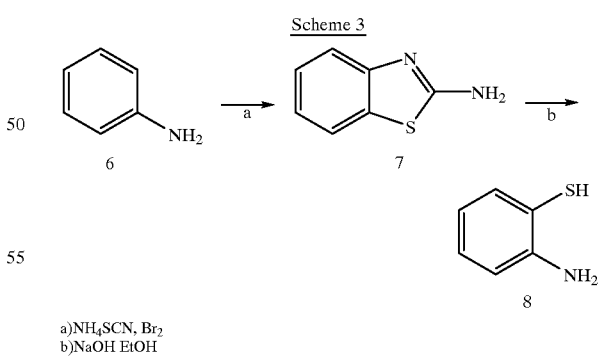

a)$NH_4SCN$, $Br_2$
b)NaOH EtOH

If the desired 2-amino benzenethiol 8-scheme 3 is not commercially available it can be synthesized by reaction of the phenyl aniline with the thiocyanate anion in the presence of an oxidant (like bromine) to produce the 2-aminobenzthiazole 7-scheme 3. This thiazole can then be hydrolyzed to the desired 2-aminobenzenethiol 8-scheme 3 with a strong base like NaOH in a protic solvent (i.e., EtOH).

Scheme 4

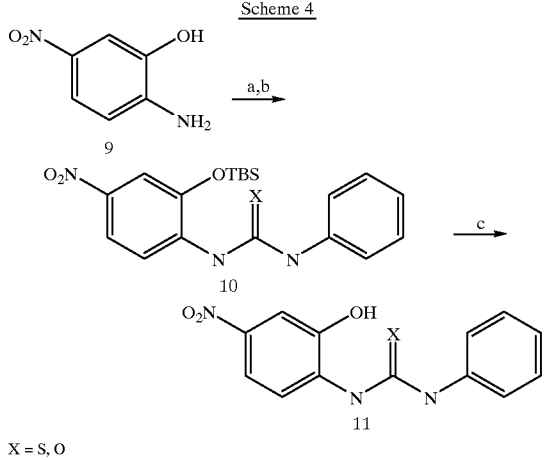

X = S, O

In the case where the thioisocyanate or phenylisocyanate is not commercially available, the thiourea or urea 11-scheme 4 may be prepared from the commercially available ortho substituted aniline. This compound is first protected with a protecting group (tert-butyl dimethyl silyl or benzyl) by conditions well known in the art(see Greene, T *Protecting Groups in Organic Synthesis*, Wiley&Sons, New York, 1981). This protected aniline is then reacted, in the presence of a base(like triethyl amine or sodium bicarbonate), with either thiophosgene or a solution of phosgene in an aprotic solvent (ie. DMF, toluene), followed by aniline to produce the protected thiourea or urea respectively. The corresponding urea or thiourea is then deprotected, using conditions standard in the art, to form the desired thiourea or urea 11-scheme 4.

Scheme 5

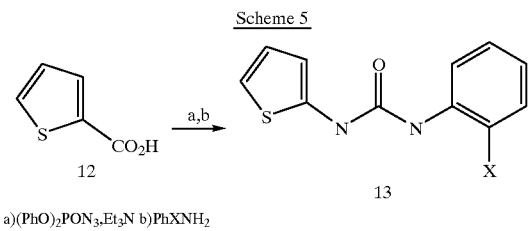

a)(PhO)$_2$PON$_3$,Et$_3$N b)PhXNH$_2$
X = OH, NHSO$_2$R, SH

Alternately the urea can be formed using a Curtius rearrangement from the corresponding aromatic or thiophene carboxylic acid 12-scheme 5. The carboxylic acid is submitted to standard Curtius conditions ((PhO)$_2$PON$_3$, Et$_3$N or ClCOCOCl followed by NaN$_3$) and the intermediate isocyanate is trapped by an appropriately substituted aniline.

Pharmaceutically acceptable salts of compounds of Formula (I) may be obtained in known manner, for example by treatment thereof with an appropriate amount of acid or base in the presence of a suitable solvent.

Another aspect of the present invention is the novel synthesis of cyano nitrophenol intermediates. Numerous conversions of aryl halides to aryl cyano derivatives with copper (I) cyanide have been published. However, no examples of an aryl ring with a hydroxy group present were mentioned. Several attempts to obtain a cyano phenol moiety with published results failed. Using known conditions of elevated temperatures, greater than 170° C., such as from 180 to 210° did not yield displacement of the halogen to a cyano moiety. Standard bases, such as DMF and pyridine further provided no desired product. Intermediates such as 2-amino-5-fluorophenol, 2-nitro-5-fluorophenol, 2-nitro-5-methyl-6-bromophenol were tried with a change of halogens, from fluorine to chlorine to bromine, and with use of copper (I) cyanide. The use of a bromine derivative, such as 2-nitro-5-methyl-6-bromophenol, with dimethylformamide and using triethylamine with a catalytic amount of dimethylamino pyridine and copper (I) cyanide at reduced temperatures,. i.e. <100° C., preferably 60 to about 80° C. for reduced times from strandarized procedures, i.e., <18 hours, preferably about 4 to 6 hours yielded the desired products.

Therefore one aspect of the invention is to a process for producing a cyano phenol derivative of the formula:

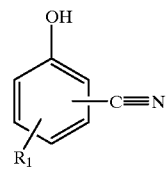

wherein R$_1$ is as defined for Formula (I) above, which method comprises reacting a compound of the formula:

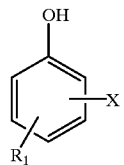

wherein X is halogen with copper (I) cyanide, dimethylformamide, triethylamine and a catalytic amount of dimethylamino pyridine. Preferably, the process is run at reduced temperatures of about 60 to about 80° C. Preferably X is bromine.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz or 400 MHz using a Bruker AM 250 or Am 400 spectrometer, respectively. Multiplicities indicated are: s=singlet, d=doublet, t=triplet, q=quartet, m=multiplet and br indicates a broad signal. Sat. indicates a saturated solution, equiv. indicates the proportion of a molar equivalent of reagent relative to the principal reactant.

Flash chromatography is run over Merck Silica gel 60 (230–400 mesh).

SYNTHETIC EXAMPLES

The invention will now be described by reference to the following examples which are merely illustrative and are not to be construed as a limitation of the scope of the present invention. All temperatures are given in degrees centigrade, all solvents used herein are of the highest available purity and all reactions are run under anhydrous conditions in an argon atmosphere unless otherwise indicated.

General Method A
Synthesis of N,N'-phenylurea

To a solution of substituted phenyl isocyanate (1.0 equiv.) in toluene (5 miliLiters (hereinafter "mL")) the corresponding aniline (1.0 equiv.) was added. The reaction mixture was stirred at about 80° C. until complete (24–48 hours (hereinafter "hrs" or "h")), then cooled to room temperature. The purifications, yields and spectral characteristics for each individual compound are listed below.

General Method B
Synthesis of N,N'-phenylurea

To a solution of phenyl isocyanate (1.0 equiv.) in dimethyl formamide (1 mL) the corresponding aniline (1.0 equiv.) was added. The reaction mixture was stirred at about 80° C. until complete (24–48 hours), then the solvent was removed under vacuum. The purifications, yields and spectral characteristics for each individual compound are listed below.

General Method C
Synthesis of Sulfonainde

The ortho substituted aniline (1 equiv.), triethyl amine (1 equiv.) and the desired sulfonyl chloride (1 equiv.) were combined in methylene chloride and allowed to stir at about 23° C. until complete (12–36 h). The reaction mixture was partitioned between water and methylene chloride. The organic layer was separated and dried over magnesium sulfate, filtered and concentrated in vacuo. The purifications of each compound are listed below.

EXAMPLE 1

Preparation of N-[2-Hydroxy-4-(methoxycarbonyl) phenyl]-N'-phenylurea

N-[2-Hydroxy-(methoxycarbonyl)phenyl]-N'-phenylurea was prepared from methyl-4-amino-3-hydroxybenzoate (200 mg, 1.19 mmol) and phenyl isocyanate (1.19 mmol) according to the procedure noted above in General Method A. The product was purified by precipitation from toluene, and filtering, to afford the titled compound (309 mg, 90%). mp: 188.4–188.8° C.; $^1$H NMR (CD$_3$OD/CDCl$_3$): δ 8.15 (d, 1H, J=8.25 Hz), 7.70 (s, 1H), 7.51 (d, 1H, J=8.25 Hz), 7.43 (d, 2H, J=8.25 Hz), 7.30 (t, 2H, J=8.25 Hz), 7.01 (t, 1H, J=8.25 Hz), 3.87 (s, 3H); EI-MS m/z 286 (M+H)$^+$; Anal. (C$_{15}$H$_{14}$N$_2$O$_4$) C, H, N.

EXAMPLE 2

Preparation of N-[5-nitro-2-hydroxyphenyl]-N'-phenylurea

The N-[5-nitro-2-hydroxyphenyl]-N'-phenylurea was prepared from the 5-nitro 2-hydroxy aniline and phenyl isocyanate according to the procedure in General Method A. The product was purified by precipitation from toluene and filtering to afford the titled compound (100 mg, 30%). 1H NMR (CD$_3$OD): δ 9.48 (s, 1H, NH), 9.07 (d, J=1.56 Hz, NH), 8.55 (s, 1H), 7.80 (dd, 1H, J=6.25 Hz and J=1.56 Hz), 7.50 (d, 2H, J=6.25 Hz), 7.30 (t, 2H, J=6.25 Hz), 7.01 (m, 2H). EI-MS m/z 273 (M+H)$^+$.

EXAMPLE 3

Preparation of 3-hydroxy-4-{[(phenylamino) carbonyl]amino}benzamide a) Preparation of 0.67 Molar (hereinafter "M") Stock Solutions of Aluminum Amide Reagents To a suspension of the appropriate hydrochloride (0.02 mole (hereinafter "mol")) in dry toluene (20 mL) at about 0° C., was slowly added a solution of (2M, 10 mL) of trimethyl aluminum in toluene. After the addition was complete, the reaction mixture was allowed to warm to room temperature and was stirred for about 1–2 hours until gas evolution has ceased.

b) Preparation of 3-hydroxy-4-{[(phenylamino)carbonyl] amino}benzamide

To a solution of the N-[2-hydroxy-4-(methoxycarbonyl) phenyl]-N'-phenylurea (60 miligram (hereinafter "mg"), 0.2 mmol) in toluene (2 mL) was added aluminum amide reagent (0.9 mL, 0.67M). The reaction mixture was stirred at reflux for about 12 hours. The reaction mixture was cooled to room temperature and was carefully quenched with 5% HCl. The organic layer was separated and the aqueous layer was extracted three times with ethyl acetate. The organic extracts were combined, dried over MgSO$_4$, filtered and concentrated under reduced pressure. Chromatography of the resulting solid on silica gel (ethyl acetate) gave the desired amide (28 mg, 49%). mp: 106.8–107.1° C.; $^1$H NMR (CD$_3$OD/CDCl$_3$): δ 7.98 (d, 1H, J=8.25 Hz), 7.35 (d, 2H, J=8.25 Hz), 7.30 (d, 2H, J=8.25 Hz), 7.17 (t, 2H, J=8.25 Hz), 6.91 (t, 1H, J=8.25 Hz); EI-MS m/z 271 (M+H)$^+$; Anal. (C$_{14}$H$_{13}$N$_3$O$_3$) C, H, N.

EXAMPLE 4

Preparation of N-(2-hydroxy-4-fluorophenyl)-N'-phenylurea a) Preparation of 2-amino-5-fluorophenol A mixture of 5-fluoro-2-nitrophenol (500 mg, 3.18 mmol) and tin (II) chloride (1.76 g, 9.2 mmol) in ethanol (10 mL) was heated at 80° C. under argon. After 30 min, the starting material had disappeared and the solution was allowed to cool down and then poured into ice. The pH was made slightly basic (pH 7–8), by addition of 5% aqueous sodium bicarbonate, before being extracted with ethyl acetate. The organic phase was washed with brine, dried over MgSO$_4$ and filtered. Evaporation of the solvent gave the title compound(335 mg, 83%). $^1$H NMR (CD$_3$OD/CDCl$_3$): δ 6.6 (m, 1H), 6.38 (dd, 1H, J=8.3 Hz and J=2.8 Hz), and J=2.8Hz), 6.29 (m, 1H).

b) Preparation of N-(2-hydroxy-4-fluorophenyl)-N'-phenylurea

N-(2-Hydroxy-4-fluorophenyl)-N'-phenylurea was prepared from 2-amino-5-fluoro phenol (200 mg, 1.57 mmol) and phenyl isocyanate according to the procedure in General Method A. The product was purified by precipitation from toluene and filtering to afford the titled compound (352 mg, 91%). mp: 195.5–195.7° C.; $^1$H NMR (CD$_3$OD/CDCl$_3$): δ 7.70 (m, 1H), 7.3 (d, 2H, J=8.25 Hz), 7.15 (t, 2H, J=8.25 Hz), 6.89 (t, 1H, J=8.25 Hz), 6.50–6.38 (m, 2H); EI-MS m/z 246 (M+H)$^+$; Anal. (C$_{13}$H$_{11}$N$_2$O$_2$F) C, H, N.

EXAMPLE 5

Preparation of 2-{[(phenylamino)carbonyl] amino}thiophenol

2-{[(Phenylamino)carbonyl]amino}thiophenol was prepared from 2-aminothiophenol (200 mg, 1.6 mmol) and phenyl isocyanate according to the procedure in General Method A. The product was purified by precipitation from toluene and filtering to afford the titled compound (330 mg, 85%). mp: 194.5° C.; $^1$H NMR (CD$_3$OD/CDCl$_3$): δ 7.48–7.26 (m, 4H), 7.25–7.10 (m, 3H), 7.04–6.79 (m, 2H); EI-MS m/z 244 (M+H)$^+$; Anal. (C$_{13}$H$_{12}$N$_2$OS) C, H, N.

EXAMPLE 6

Preparation of N-(2-Carboxy-4-hydroxyphenyl)-N'-phenylurea

N-(2-Carboxy-4-hydroxyphenyl)-N'-phenylurea was prepared from 2-amino-5-hydroxy benzoic acid (1 g, 6.53 mmol) according to the procedure in General Method B. The reaction mixture was partitioned between ethyl acetate and water. The organic phase was washed with brine, dried over $MgSO_4$ and filtered. Removal of solvent under reduced pressure and chromatography of the resulting solid on silica gel (hexane:ethyl acetate, 1:1 to 100% ethyl acetate) gave the titled compound (1.5 g, 84%). $^1$H NMR ($CD_3OD/CDCl_3$): δ 8.36 (d, 1H, J=8.25 Hz), 7.63 (m, 4H), 7.48 (t, 2H, J=8.25 Hz), 7.20 (m, 1H); EI-MS m/z 272 (M+H)$^+$; Anal. ($C_{14}H_{12}N_2O_4$) C, H, N.

EXAMPLE 7

Preparation of N -[2-hydroxy-4-(trifluoromethyl) phenyl]-N'-phenylurea a) Preparation of 2-nitro-5-trifluoromethylphenol 2-Nitro-5-trifluoromethylphenol was prepared by adding concentrated $HNO_3$ (6 mL) drop-wise to α,α,α-trifluoro-m-cresol (5 g, 30.8 mmol) at room temperature. After the addition was complete. the reaction was quenched with saturated ammonium acetate and extracted with EtOAc. The organic was separated, dried over sodium sulfate and filtered. Concentration of the solution in vacuo afforded an oil which was purified by column chromatography (gradient 100% hexane to 50% EtOAc/hexanes) to afford the titled compound as an oil(1.7 g, 27%). 1H NMR ($CDCl_3$): 10.6 (s, 1H, OH), 8.26(d, 1H, J=7.8 Hz), 7.45(s, 1H, arom), 7.26(d, 1H, J=7.8 Hz).

b) Preparation of 2-amino-5-trifluoromethylphenol

2-Amino-5-trifluoromethylphenol was prepared by treating 2-nitro-5-trifluoromethylphenol (500 mg, 2.41 mmol) with a solution of $SnCl_2$(3.5 g, mmol) in EtOH at 23° C. for 12 h. The mixture was concentrated to 50 mL and adjusted to pH 7 using saturated sodium bicarbonate. The reaction mixture was partitioned between $H_2O$ and EtOAc. The aqueous layer was separated and extracted with EtOAc. The combined organic extracts were dried over sodium sulfate, filtered and concentrated in vacuo. The resulting colorless oil(370 mg, 87%) was used without further purification. $^1$H NMR ($CDCl_3$): 7.6 (s, 1H), 7.39(d, 1H, J=8.5 Hz), 7.08(d, 1H, J=8.5 Hz).

c) Preparation of N-[2-hydroxy-4-(trifluoromethyl)phenyl]-N'-phenylurea

N-[2-Hydroxy-4-(trifluoromethyl)phenyl]-N'-phenylurea was prepared from 2-amino-5-trifluoromethylphenol (150 mg, 1.09 mmol) and phenyl isocyanate(1.09 mmol) according to the procedure in General method A. The product was purified by precipitation from methylene chloride and filtering to afford the titled compound (230 mg, 87% ). mp: ° C.; 1H NMR (DMSO-$d_6$): δ 9.45 (s, 1H, NH), 8.50 (s, 1H, NH), 8.31 (d, 1H, J=10.0 Hz), 7.45 (d, 2H, J=10.0 Hz), 7.29 (t, 2H, J=6.67 Hz), 7.10 (m, 2H), 6.99 (t, 1H, J=6.67 Hz). EI-MS m/z 296 (M$^+$). Anal. ($C_{14}H_{11}N_2O_2F_3$)C, H, N.

EXAMPLE 8

Preparation of N-(2-hydroxy-4-nitrophenyl)-N'-(2-hydroxy-4-nitrophenyl)urea a) Preparation of 2-(tert-butyldimethylsilyloxy)-4-nitroaniline To a solution of 2-amino-5-nitrophenol (1 g, 6.49 mmol) and imidazole (0.88 g, 12.3 mmol) in DMF (15 mL), tert-butyldimethylsilyl chloride (11.2 mL, 64.9 mmol) was added. The resulting mixture was allowed to stir at 23° C. for 48 hours. The reaction mixture was partitioned between 0.1% HCl and ethyl acetate. The combined organic phase was washed with brine, dried over $MgSO_4$ and filtered. Removal of solvent at reduced pressure and chromatography of the resulting oil on silica gel (hexane:ethyl acetate; 5:1) gave the tided compound (1.7 g, 98%). $^1$H NMR ($CDCl_3$): δ 7.78 (dd, 1H, J=6.7 Hz and J=2.7 Hz), 7.61 (d, 1H, J=2.7 Hz), 6.7 (d, 1H, J=8.8 Hz), 1.0 (s, 9H), 0.28 (s, 6H).

b) Preparation of N-[(2-tert-butyldimethylsilyloxy)-4-nitrophenyl]-N'-[(2-tert-butyldimethylsiloxy)-4-nitrophenyl]urea To a solution of 2-(tert-butyldimethylsilyloxy)-4-nitroaniline(200 mg, 0.75 mmol) in toluene (10 mL) triethylamine (0.13 mL, 1.64 mmol) and triphosgene (88.4 mg, 0.3 mmol) were added. The reaction mixture was stirred at 70° C. for 2 hours, then cooled to room temperature. Then more 2-(tert-butyldimethylsilyloxy)-4-nitroaniline (200 mg, 0.75 mmol) was added. The resulting mixture was allowed to stir at 70° C. for 48 hours then cooled to room temperature. The reaction mixture was partitioned between water and ethyl acetate. The combined organic phase was washed with brine, dried over $MgSO_4$ and filtered. Removal of solvent at reduced pressure and chromatography of the resulting oil on silica gel (hexane:ethyl acetate, 10:1) gave the titled compound(130 mg, 31%). $^1$H NMR ($CDCl_3$): δ 8.36 (d, 2H, J=8.3 Hz), 7.90 (dd, 2H, J=8.3 Hz and J=2.8 Hz), 7.71 (d, 2H, J=2.8 Hz), 7.22 (s, 2H), 1.02 (s, 18H), 0.35 (s, 12H).

c) Preparation of N-(2-Hydroxy-4-nitrophenyl)-N'-(2-hydroxy-4-nitrophenyl)urea

To a solution of N-[(2-tert-butyldimethylsilyloxy)-4-nitrophenyl]-N'-[(2-tert-butyldimethylsilyloxy)-4-nitrophenyl]urea(50 mg, 0.089 mmol) in THF (2 mL), tetrabutylammonium fluoride (1 M, 0.09 mL, 0.089 mmol) was added at 0° C. The reaction mixture was stirred at 23° C. After 1 hour, the starting material had disappeared. The reaction mixture was partitioned between water and ethyl acetate. The combined organic phase was dried over $MgSO_4$ and filtered. Removal of solvent at reduced pressure and chromatography of the resulting oil on silica gel (hexane:ethyl acetate; 1:1 to 100% ethyl acetate) gave the titled compound(24 mg, 81%). $^1$H NMR ($CD_3OD/CDCl_3$): δ 8.32 (d, 2H, J=8.25 Hz), 7.80 (dd, 2H, J=8.25 Hz and J=2.06 Hz), 7.7 (d, 2H, J=2.06 Hz). EI-MS m/z 334 (M+H)$^+$. Anal. ($C_{13}H_{10}N_4O_7$) C, H, N.

EXAMPLE 9

Preparation of N-(2-hydroxy-4-nitrophenyl)-N'-phenyl-thiourea a) Preparation of N-(2-tert-butyldimethysilyloxy-4-nitrophenyl)-N'-phenyl-thiourea N-(2-tert-Butyldimethysilyloxy-4-nitrophenyl)-N'-phenyl-thiourea was prepared by treating a biphasic solution of 2-tert-butyldimethysilyloxy-4-nitroaniline(80 mg, 0.308 mmol) and $NaHCO_3$ in $CHCl_3$:$H_2O$(2.5:1, 7 mL) with thiophosgene at 0° C. The solution was allowed to warm to 23° C. and the reaction was continued overnight The $CHCl_3$ layer was separated and dried over sodium sulfate. The solution was concentrated in vacuo and the residue was dissolved in toluene and treated with aniline (100 uL) at 23° C. for 12 h. The reaction mixture was concentrated and the residue was purified by flash chromatography (10% EtOAc/hexanes) to afford the titled compound as a yellow solid (120.8 mg, 98%) mp: 144–145° C.; $^1$H NMR ($CD_3OD/CDCl_3$): δ 8.65 (d, 1H, J=10.0 Hz), 7.58 (d, 1H, J=10.0 Hz), 7.47 (d, 1H, J=1.25 Hz), 7.26 (m, 4H), 7.10 (m, 1H).

b) Preparation of N-(2-hydroxy-4-nitrophenyl)-N'-phenyl-thiourea

N-(2-Hydroxy-4-nitrophenyl)-N'-phenyl-2-thiourea was prepared by treating a solution of N-(2-tert-butyldimethysilyloxy-4-nitrophenyl)-N'-phenyl-thiourea (100 mg, 0.248 mmol) in $CH_3CN$ (1 mL) with $Et_3N.HF$ (100 uL, 0.62 mmol) in acetonitrile for 10 minutes at 23° C. The solution was concentrated and flushed through a silica plug with EtOAc to afford the desired compound as an orange solid (55 mg, 77%). mp: 144–145° C;$^1$H NMR (CD$_3$OD/CDCl$_3$): δ 8.65 (d, 1H, J=10.0 Hz), 7.58 (d, 1H, J=10.0 Hz), 7.47 (d, 1H, J=1.25 Hz), 7.26 (m, 4H), 7.10 (m, 1H).

EXAMPLE 10

Preparation of N-(4-nitro 2-(phenylsulfonylamino) phenyl)-N'-phenylurea a) Preparation of 4-nitro 2-(phenylsulfonylamino)aniline A solution of 4-nitro 1,2-phenylene diamine(1.53 g, 10.0 mmol) in DMF was treated with phenyl sulfonyl chloride (1.76 g, 10.0 mmol) and triethyl amine(1.01 g) in DMF for 12 h at 23° C. The reaction mixture was partitioned between saturated NH$_4$Cl and methylene chloride. The organic layer was dried over sodium sulfate, filtered and concentrated in vacuo. The resulting solid was recrystallized (EtOH) to afford desired (0.275 g, 9%). $^1$H NMR(DMSO) 9.5(s, 1H, br), 7.83 (dd, 1H, J=10 Hz, 2 Hz), 7.74(d, 2H, J=8 Hz), 7.76(t, 1H, J=8 Hz), 7.56(t, 2H, J=8 Hz), 7.55(d,1H, J=2 Hz), 6.79 (d, 1H, J=8 Hz), 6.5 (s, 2H, br).

b) Preparation of N-(4-nitro 2-(phenylsulfonylamino) phenyl)-N'-phenylurea

N-(4-Nitro 2-(phenylsulfonylamino)phenyl)-N'-phenylurea was prepared from 4-nitro 2-(phenylsulfonylamino)aniline(82 mg) and phenyl isocyanate(33 mg) by method A. The reaction was cooled and then partitioned between saturated ammonium chloride and 9:1 methylene chloride and methanol. The organic phase was dried over magnesium sulfate, filtered and concentrated in vacua. The residue was purified by column chromatography (ethyl acetate/hexanes) to afford desired(30.8 mg, 26%). EI-MS m/z 413(M+H)$^+$.

EXAMPLE 11

Preparation of N-(2-hydroxy-5-nitrophenyl)-N'-(3-methoxy-2-thienyl)urea a) Preparation of 3-methoxy-2-thienylcarboxlic acid To a solution of 3-methoxythiophene (4.81 g, 42.1 mmol) in ether (20 mL) at −78° C., butyllithium (17 mL, 47.6 mmol) was added. The reaction mixture was stirred at −78° C. for 1 hour, then it was warmed to 0° C. for 3 hours. After to recooling −78° C. the reaction mixture was poured into a beaker filled with crushed dry ice (14.5 g) and allowed to stand until the excess dry ice had completely sublimed. Then the reaction mixture was poured into a mixture of ice (10 g) to which conc. HCl (24 mL) had been added. The product was purified by precipitation from ether and filtering (6.42 g, 96%). EI-MS m/z 159 (M+H)$^+$.

b) Preparation of N-(2-hydroxy-5-nitrophenyl)-N'-(3-methoxy-2-thienyl)urea

To a solution of 3-methoxy-2-thiophene carboxylic acid (200 mg, 1.27 mmol) in benzene, (PhO)$_2$PON$_3$ (0.33 mL), 2-amino-4-nitrophenol (195.7 mg, 1.27 mmol) and triethylamine (1.1 equiv., 0.25 mL) were added. The reaction mixture was stirred at reflux overnight. The reaction mixture was partitioned between 5% citric acid and ethyl acetate. The organic layer was separated and the aqueous layer was extracted three times with ethyl acetate. The organic extracts were combined, dried over MgSO$_4$, filtered and concentrated under reduced pressure. Chromatography of the resulting solid on silica gel (hexane:ethyl acetate; 1:1) gave a solid product (160 mg, 41%). mp: 172.6–173.0° C.; $^1$H NMR (CD$_3$OD/CDCl$_3$): δ 8.96 (d, 1H, J=2.5 Hz), 7.74 (dd, 1H, J=5.0 Hz and J=1.25 Hz), 6.82 (d, 1H, J=7.5 Hz), 6.76 (s, 2H), 3.80 (s, 3H); EI-MS m/z 309 (M+H)$^+$; Anal. (C$_{12}$H$_{11}$N$_3$O$_5$S) C, H, N.

EXAMPLE 12

Preparation of N-(2-hydroxy-4-nitrophenyl)-N'-(3-methoxy-2-thienyl)urea

To a solution of 3-methoxy-2-thiophene carboxylic acid (example 11a, 200 mg, 1.27 mmol) in toluene, (PhO)$_2$PON$_3$ (0.33 mL) and triethylamine (1.1 equiv., 0.25 mL) were added. The reaction mixture was stirred at 70° C. for 2 hours and cooled down to room temperature then 2-amino-5-nitrophenol was added. The reaction mixture was stirred at 70° C. overnight. The reaction mixture was partitioned between 5% citric acid and ethyl acetate. The organic layer was separated and the aqueous layer was extracted three times with ethyl acetate. The organic extracts were combined, dried over MgSO$_4$, filtered and concentrated under reduced pressure. Chromatography of the resulting solid on silica gel (hexane:ethyl acetate;1:1) gave the product (190 mg, 48%). $^1$H NMR (CD$_3$OD/CDCl$_3$): δ 8.38 (d, 1H, J=5.0 Hz), 7.85 (dd, 1H, J=5.0 Hz and J=1.25 Hz), 7.76 (d, 1H, J=2.5 Hz), 6.9 (s, 2H), 3.95 (s, 3H); EI-MS m/z 309 (M+H)$^+$; Anal. (C$_{12}$H$_{11}$N$_3$O$_5$S) C, H, N.

EXAMPLE 13

Preparation of N-(2-hydroxy-4-nitrophenyl)-N'-(3-methoxyphenyl)urea

N-(2-Hydroxy-4-nitrophenyl)-N'-(3-methoxyphenyl)urea was prepared from 2-hydroxy 4-nitro aniline (154 mg, 1.0 mmol) and 3-methoxyphenylisocyanate(1.0 mmol) according to the procedure in General Method B. The product was purified by dilution with methylene chloride and precipitation with hexanes. Filtering afforded the title compound (140 mg, 46%). EI-MS m/z 302(M−H)$^-$.

EXAMPLE 14

Preparation of N-(2-hydroxy-4-nitrophenyl)-N'-(2-methoxyphenyl)urea

N-(2-Hydroxy-4-nitrophenyl)-N'-(2-methoxyphenyl)urea was prepared from 2-hydroxy 4-nitro aniline (154 mg, 1.0 mmol) and 2-methoxyphenylisocyanate(1 mmol.) according to the procedure in General Method B. The product was purified by dilution with methylene chloride and precipitation with hexanes. Filtering afforded the title compound (82 mg, 27%). EI-MS m/z 302(M−H)$^-$

EXAMPLE 15

Preparation of N-(2-hydroxy-4-nitrophenyl)-N'-(3-trifluoromethylphenyl)urea

N-(2-Hydroxy-4-nitrophenyl)-N'-(3-methoxyphenyl)urea was prepared from 2-hydroxy 4-nitro aniline (154 mg, 1.0 mmol) and 3-trifluoromethylphenylisocyanate (1 mmol) according to the procedure in General Method B. The product was purified by dilution with methylene chloride and precipitation with hexanes. Filtering afforded the title compound (180 mg, 52%). EI-MS m/z 342(M+H)$^+$.

EXAMPLE 16

Preparation of N-(2-hydroxy-4-nitrophenyl)-N'-(2-trifluoromethylphenyl)urea

N-(2-Hydroxy-4-nitrophenyl)-N'-(2-trifluoromethylphenyl)urea was prepared from 2-hydroxy 4-nitro aniline (154 mg, 1.0 mmol) and 2-trifluoromethylphenylisocyanate (1.0 mmol) according to the procedure in General Method B. The product was purified by dilution with methylene chloride and precipitation with hexanes. Filtering afforded the title compound (180 mg, 52%). EI-MS m/z 342(M+H)$^+$.

EXAMPLE 17

Preparation of N-(2-hydroxy-4-nitrophenyl)-N'-(4-trifluoromethylphenyl)urea

N-(2-Hydroxy-4-nitrophenyl)-N'-(4-trifluoromethylphenyl)urea was prepared from 2-hydroxy 4-nitro aniline (154 mg, 1.0 mmol) and 4-trifluoromethylphenylisocyanate (1.0 mmol) according to the procedure in General Method B. The product was purified by dilution with methylene chloride and precipitation with hexanes. Filtering afforded the title compound (111 mg, 32%). EI-MS m/z 340(M–H)$^-$.

EXAMPLE 18

Preparation of N-(2-hydroxy-4-nitrophenyl)-N'-(2-bromophenyl)urea

N-(2-Hydroxy-4-nitrophenyl)-N'-(2-bromophenyl)urea was prepared from 2-hydroxy 4-nitro aniline (500 mg, 3.24 mmol) and 2-bromophenylisocyanate (3.24 mmol) according to the procedure in General Method B. The product was purified by dilution with methylene chloride and precipitation with hexanes. Filtering afforded the title compound(530 mg, 47%). EI-MS m/z 350(M–H)$^-$.

EXAMPLE 19

Preparation of N-(2-hydroxy-4-nitrophenyl)-N'-(3-bromophenyl)urea

N-(2-Hydroxy-4-nitrophenyl)-N'-(3-bromophenyl)urea was prepared from 2-hydroxy 4-nitro aniline (500 mg, 3.24 mmol) and 3-bromophenylisocyanate (3.24 mmol)according to the procedure in General Method B. The product was purified by dilution with methylene chloride and precipitation with hexanes. Filtering afforded the title compound (0.96g, 87%). EI-MS m/z 350(M–H)$^-$.

EXAMPLE 20

Preparation of N-(2-hydroxy-4-nitrophenyl)-N'-(4-bromophenyl)urea

N-(2-Hydroxy-4-nitrophenyl)-N'-(4-bromophenyl)urea was prepared from 2-hydroxy 4-nitro aniline (500 mg, 3.24 mmol) and 4-bromophenylisocyanate (3.24 mmol) according to the procedure in General Method B. The product was purified by dilution with methylene chloride and precipitation with hexanes. Filtering afforded the title compound (0.41 g, 37%). EI-MS m/z 352(M+H)$^+$.

EXAMPLE 21

Preparation of N-(2-hydroxy-4-nitrophenyl)-N'-(2-phenylphenyl)urea

N-(2-Hydroxy-4-nitrophenyl)-N'-(2-phenylphenyl)urea was prepared from 2-hydroxy 4-nitro aniline (500 mg, 3.24 mmol) and 2-phenylphenylisocyanate (3.24 mmol) according to the procedure in General Method B. The product was purified by dilution with methylene chloride and precipitation with hexanes. Filtering afforded the title compound (0.22 g, 19%). EI-MS m/z 350(M+H)$^+$.

EXAMPLE 22

Preparation of N-(2-hydroxy-4-nitrophenyl)-N'-(1-naphthyl)urea

N-(2-Hydroxy-4-nitrophenyl)-N'-(1-naphthyl)urea was prepared from 2-hydroxy 4-nitro aniline (500 mg, 3.24 mmol) and 1-naphthylisocyanate (3.24 mmol) according to the procedure in General Method B. The product precipitated from methylene chloride and filtered. The resulting solid was titruated with 1:3 triethyl amine:methylene chloride. The filterate was concentrated in vacuo. The resulting residue was dissolved in methylene chloride and treated with 1N HCl in water. The desired product precipitated from solution and was collected by filtration(0.11 g, 10%). EI-MS m/z 324(M+H)$^+$.

EXAMPLE 23

Preparation of N-(2-hydroxy-4-nitrophenyl)-N'-(2-nitrophenyl)urea

N-(2-Hydroxy-4-nitrophenyl)-N'-(2-nitrophenyl)urea was prepared from 2-hydroxy 4-nitro aniline (500 mg, 3.24 mmol) and 2-nitrophenylisocyanate (3.24 mmol) according to the procedure in General Method B. The product was purified by dilution with methylene chloride and precipitation with hexanes. Filtering afforded the title compound (0.44 g, 44%). EI-MS m/z 319(M+H)$^+$.

EXAMPLE 24

Preparation of N-(2-hydroxy-4-nitrophenyl)-N'-(2-fluorophenyl)urea

N-(2-Hydroxy-4-nitrophenyl)-N'-(2-fluorophenyl)urea was prepared from 2-hydroxy 4-nitro aniline (500 mg, 3.24 mmol) and 2-fluorophenylisocyanate (3.24 mmol) according to the procedure in General Method B. The product was purified by dilution with methylene chloride and precipitation with hexanes. Filtering afforded the title compound (0.59 g, 31%). EI-MS m/z 292(M+H)$^+$.

EXAMPLE 25

Preparation of N-(2-hydroxy-4-nitrophenyl)-N'-(2,6-difluorophenyl)urea

N-(2-Hydroxy-4-nitrophenyl)-N'-(2,6-difluorophenyl)urea was prepared from 2-hydroxy 4-nitro aniline (500 mg, 3.24 mmol) and 2,6-difluorophenylisocyanate(3.24 mmol) according to the procedure in General Method B. The product was purified by dilution with methylene chloride and precipitation with hexanes. Filtering afforded the title compound(0.91 g, 91%). EI-MS m/z 308(M–H)$^-$.

EXAMPLE 26

Preparation of N-(2-hydroxy-4-nitrophenyl)-N'-(2-ethoxyphenyl)urea

N-(2-Hydroxy-4-nitrophenyl)-N'-(2-ethoxyphenyl)urea was prepared from 2-hydroxy 4-nitro aniline (500 mg, 3.24 mmol) and 2-ethoxyphenylisocyanate (3.24 mmol) according to the procedure in General Method B. The product was purified by dilution with methylene chloride and precipitation with hexanes. Filtering afforded the title compound (0.84 g, 81%) EI-MS m/z 318(M+H)$^+$.

EXAMPLE 27

Preparation of N-(2-hydroxy-4-nitrophenyl)-N'-(2-ethylphenyl)urea

N-(2-Hydroxy-4-nitrophenyl)-N'-(2-ethylphenyl)urea was prepared from 2-hydroxy 4-nitro aniline (500 mg, 3.24 mmol) and 2-ethylphenylisocyanate (3.24 mmol) according to the procedure in General Method B. The product was purified by dilution with methylene chloride and precipitation with hexanes. Filtering afforded the title compound (0.44 g, 43%). EI-MS m/z 302(M+H)+.

EXAMPLE 28

Preparation of N-(2-hydroxy-4-nitrophenyl)-N'-(2-trifluoromethoxyphenyl)urea

N-(2-Hydroxy-4-nitrophenyl)-N'-(2-trifluoromethyloxyphenyl)urea was prepared from 2-hydroxy 4-nitro aniline (500 mg, 3.24 mmol) and 2-trifluoromethoxyphenylisocyanate (3.24 mmol) according to the procedure in General Method B. The product was purified by dilution with methylene chloride and precipitation with hexanes. Filtering afforded the title compound (0.69 g, 60%). EI-MS m/z 358(M+H)+.

EXAMPLE 29

Synthesis of N-(2-hydroxy-4-nitrophenyl) N'-(2-methylthiophenyl)urea

The urea was prepared from 2-hydroxy 4-nitro aniline (500 mg, 3.24 mmol) and 2-methylthio phenylisocyanate (3.24 mmol) by general Method B. The product was purified by dilution with methylene chloride and precipitation with hexanes. Filtering afforded the title compound(0.63 g, 61%). EI-MS m/z 320(M+H)+.

EXAMPLE 30

Synthesis of N-(2-hydroxy-4-nitrophenyl) N'-(2-chloro 6-methylphenyl)urea

The urea was prepared from 2-hydroxy 4-nitro aniline (500 mg, 3.24 mmol) and 2-chloro 6-methyl phenylisocyanate by general Method B. It was purified by dilution with methylene chloride and precipitation with hexane. Filtering afforded the desired compound(0.31 g, 29%). EI-MS m/z 322(M+H)+.

EXAMPLE 31

Synthesis of N-(2-hydroxy-4-nitrophenyl) N'-(2-methylsulfoxyphenyl)urea

The urea was synthesized by treatment of N-(2-hydroxy 4-nitrophenyl) N'-(2-methyl thiophenyl)urea(example 28, 100 mg) with sodium periodate(100 mg) in t-butanol/water for 12 hours at 23° C. The product precipitated from the reaction mixture(30 mg, 29%). EI-MS m/z 336(M+H)+.

EXAMPLE 32

Synthesis of N-(2-hydroxy 4-trifluoromethylphenyl) N'-(2-bromophenyl)urea

The urea was prepared from 2-hydroxy 4-trifluoromethyl aniline(example 7a, 0.171 g, 1 mmol) and 2-bromophenylisocyanate(1 mmol) by general Method B. It was purified by dilution with methylene chloride and pre-cipitation with hexane. Filtering afforded the desired compound(0.25 g, 54%). EI-MS m/z 375(M+H)+.

EXAMPLE 33

Synthesis of N-(2-hydroxy 4-carbomethoxyphenyl) N'-(2-bromophenyl)urea

The urea was prepared from 2-hydroxy 4-carbomethoxy aniline(0.167 g, 1 mmol) and 2-bromophenylisocyanate(1 mmol) by general Method B. It was purified by dilution with methylene chloride and precipitation with hexane. Filtering afforded the desired compound(0.12 g, 33%). EI-MS m/z 363(M–H)–.

EXAMPLE 34

Synthesis of N-(2-hydroxy-4-trifluoromethylphenyl) N'-(2-phenylphenyl)urea

The urea was prepared from 2-hydroxy 4-trifluoromethyl aniline(example 7a, 0.171 g, 1 mmol)) and 2-phenylphenylisocyanate by general Method B. It was purified by dilution with methylene chloride and precipitation with hexane. Filtering afforded the desired compound (0.24 g, 64%). EI-MS m/z 373(M+H)+.

EXAMPLE 35

Synthesis of N-(2-hydroxy 4-carbomethoxyphenyl) N'-(2-phenylphenyl)urea

The urea was prepared from 2-hydroxy 4-carbomethoxy aniline(0.167 g, 1 mmol) and 2-phenylphenylisocyanate(1 mmol) by general Method B. It was purified by dilution with methylene chloride and precipitation with hexane. Filtering afforded the desired compound(0.185 g, 50%). EI-MS m/z 363(M–H)–.

EXAMPLE 36

Synthesis of N-(2-hydroxy 4-nitrophenyl) N'-(2,3-dichlorophenyl)urea

The urea was prepared from 2-hydroxy 4-nitro aniline (308 mg, 2 mmol) and 2,3-dichlorophenyl isocyanate(2 mmol) by general Method B. It was purified by dilution with methylene chloride and precipitation with hexane. Filtering afforded the title compound(0.5 g, 73%). EI-MS m/z 342 (M+H)+.

EXAMPLE 37

Synthesis of N-(2-hydroxy 4-nitrophenyl) N'-(2,4-dichlorophenyl)urea

The urea was prepared from 2-hydroxy 4-nitro aniline (308 mg, 2 mmol) and 2,4-dichlorophenylisocyanate(2 mmol) by general Method B. It was purified by dilution with methylene chloride and precipitation with hexane. Filtering afforded the title compound(0.26 g, 38%). EI-MS m/z 342 (M+H)+.

EXAMPLE 38

Synthesis of N-(2-hydroxy-4-nitrophenyl) N'-(2-chlorophenyl)urea

The urea was prepared from 4-nitro 2-hydroxy aniline (308 mg, 2 mmol) and 2-chlorophenylisocyanate(2 mmol) by general Method B. It was purified by dilution with methylene chloride and precipitation with hexane. Filtering afforded the title compound(0.29 g, 47%). EI-MS m/z 308 (M+H)$^+$.

EXAMPLE 39

Synthesis of N-(2-hydroxy-4-nitrophenyl) N'-(2,4-dibromophenyl)urea

The urea was prepared from 4-nitro 2-hydroxy aniline (308 mg, 2 mmol) and 2,4-dibromophenylisocyanate(2 mmol) by general Method B. It was purified by dilution with methylene chloride and precipitation with hexane. Filtering afforded the title compound(0.34 g, 39%). EI-MS m/z 430 (M+H)$^+$.

EXAMPLE 40

Synthesis of N-(2-hydroxynapthyl) N'-(2-bromophenyl)urea

The urea was prepared from 1-amino 2-hydroxynapthalene(195 mg, 1 mmol) and 2-bromophenylisocyanate(1 mmol) by general Method B. It was purified by dilution with methylene chloride and precipitation with hexane. Filtering afforded the title compound (0.030 g, 8%). EI-MS m/z 357(M+H)$^+$.

EXAMPLE 41

Synthesis of N-(2-hydroxy-4-nitrophenyl)-N'-(2,3-methylenedioxyphenyl)urea a) Preparation of 2,3-methylenedioxyphenylcarboxylic acid A solution of 1,3-benzodioxole (3.09 g, 32 mmol) in dry ether (50 mL) was treated dropwise at −10° C. with 2.5 M n-butyllithium (15 mL, 35 mmol) in hexane. When the addition was complete, the mixture was stirred under reflux for one hour. After cooling to room temperature, it was added to crushed solid carbon dioxide, and after 24 hours, the residue was treated with 10% aq. NaHCO$_3$ and ether. The alkali layer was separated, washed with ether, then acidified with cold concentrated HCl, and extracted with chloroform. The combined organic layers were dried over MgSO$_4$, filtered and concentrated under reduced pressure (1.1 g, 20%). EI-MS m/z 167 (M+H)$^+$.

b) Preparation of N-(2-hydroxy-4-nitrophenyl)-N'-(2,3-methylenedioxyphenyl)urea

To a solution of the 2,3-methylenedioxyphenylcarboxylic acid in toluene, triethylamine (0.27 mL, 1.95 mmol) and diphenylphosphoryl azide (DPPA) (0.32 mL, 1.5 mmol) were added. The reaction mixture was stirred at 60° C. for 2 hours, then 2-amino-5-nitrophenol (250 mg, 1.5 mmol) was added. The reaction mixture was stirred at 100° C. for 18 hours. After the reaction mixture was cooled to room temperature, it was partitioned between 5% citric acid and ethyl acetate. The organic layer was separated and the aqueous layer was extracted three times with ethyl acetate. The organic extracts were combined, dried over MgSO$_4$, filtered and concentrated under reduced pressure. Chromatography of the resulting solid on silica gel (hexane:ethyl acetate; 5:1) gave product (200 mg, 42%). EI-MS m/z 318 (M+H)$^+$.

EXAMPLE 42

Synthesis of N-(2-hydroxy 4-nitrophenyl) N'-(2-methoxy 3-chlorophenyl)urea

The urea was prepared from 2-hydroxy 4-nitro aniline (308 mg, 2 mmol) and 2-chioro 3-methoxyphenylisocyanate(2 mmol) by general Method B. It was purified by dilution with methylene chloride and precipitation with hexane. Filtering afforded the title compound(0.48 g, 63%). EI-MS m/z 338(M+H)$^+$.

EXAMPLE 43

Synthesis of N-(2-hydroxy 4-nitrophenyl) N'-(2-methylphenyl)urea

The urea was prepared from 2-hydroxy 4-nitro aniline (308 mg, 2 mmol) and 2-methyl phenylisocyanate(2 mmol) by general Method B. It was purified by dilution with methylene chloride and precipitation with hexane. Filtering afforded the title compound(0.38 g, 53%). EI-MS m/z 288 (M+H)$^+$.

EXAMPLE 44

Synthesis of N(bis(2-hydroxy 4-nitrophenyl) N'-(dianisidine)diurea

The urea was prepared from 2-hydroxy 4-nitro aniline (616 mg, 4 mmol) and dianidisdine diisocyanate(2 mmol) by general Method B(except 2 equiv. of 4-nitro 2-hydroxy aniline was used instead of 1 equiv.). The product was purified by dilution with methylene chloride and precipitation with hexane. Filtering afforded the title compound(0.08 g, 6%). EI-MS m/z 605(M+H)$^+$.

EXAMPLE 45

Synthesis of 4-methylene bis(N-(2-chlorophenyl) N'-(2-hydroxy 4-nitrophenyl)urea)

The urea was prepared from 2-hydroxy 4-nitro aniline (616 mg, 4 mmol) and 4-methylene bis(N-(2-chlorophenyl) diisocyanate(2 mmol) by general Method B(except 2 equiv. of 4-nitro 2-hydroxy aniline was used instead of 1 equiv.). The product was purified by dilution with methylene chloride and precipitation with hexane. Filtering afforded the title compound(0.10 g, 8%). EI-MS m/z 627(M+H)$^+$.

EXAMPLE 46

Synthesis of N-[2-hydroxy 4-(benzylamino) carbonylphenyl]-N'-(2-bromophenyl)urea a) Synthesis of N-(2-hydroxy 4-carboxylatephenyl) N'-(2-bromophenyl)urea The urea was prepared from 3-hydroxy 4-amino benzoic acid (3.69 g, 24 mmol) and 2-bromophenylisocyanate(24 mmol) by general Method B. It was purified by dilution of the DMF solution with methylene chloride and precipitation with hexane(4.0 g, 48%). EI-MS m/z 351(M+H)$^+$.

b) Preparation of N-[4(benzylamino)carbonyl-2-hydroxyphenyl]-N'-(2-bromophenyl)urea To a solution of the N-(2-hydroxy 4-carboxylate phenyl) N'-(2-bromophenyl)urea (200 mg, 0.58 mmol) in DMF (15 mL), EDC (121.9 mg, 0.58 mmol), HOBT (156.6 mg, 11.6 mmol) were added. The reaction mixture was sdrred at room temperature for 16 hours. Then the benzyl amine (123 mg, 11.6 mmol) was added. The reaction mixture was stirred at same temperature for 24 hours. Then the reaction mixture was partitioned between water and ethyl acetate. The organic layer was separated and the aqueous layer was extracted three times with ethyl acetate. The organic extracts were combined, dried over MgSO$_4$, filtered and concentrated under reduced pressure. Chromatography of the resulting solid on silica gel (hexane:ethyl acetate; 1:1) gave benzylamino product (500 mg, 65%). EI-MS m/z 441 (M+H)$^+$.

EXAMPLE 47

Synthesis of N-(2-hydroxy 4-nitrophenyl) N'-(2-phenoxyphenyl)urea

The urea was synthesized by the treatment of 2-phenoxyphenylcarboxylic acid(2 mmol,) with diphenyl phosphoryl azide(0.475 mL) and triethyl amine(0.14 mL) in DMF at 80° C. after 24 hours the 2-amino 5-nitrophenol (1 equiv.) was added. The reaction was heated for 24 hours at 80° C. The reaction product was oiled out with hexane. The residue was dissolved in methanol and the solid was precipitated out with water.(180 mg, 24%) EI-MS m/z 364(M−H)$^-$.

EXAMPLE 48

Synthesis of N-(2-hydroxy-4-fluorophenyl) N'-(2-bromophenyl)urea a) Synthesis of 2-hydroxy 4-fluoro aniline 3-fluoro 6-nitrophenol (2 g, 11 mmol) was treated with 10% Pd/C(1 g) at 23° C. The reaction mixture was flushed with hydrogen gas and the reaction was allowed to stir 12 h before it was filtered through celite. The filtrate was concentrated in vacuo to afford the title compound (1.4 g, 77%). EI-MS m/z 169(M+H)$^+$.

b) Synthesis of N-(2-hydroxy-4-fluorophenyl) N'-(2-bromophenyl)urea

The urea was prepared from 2-hydroxy 4-fluoro aniline (254 mg, 2 mmol) and 2-bromophenylisocyanate by general Method B. It was purified by dilution with methylene chloride and precipitation with hexane(173 mg, 26%). EI-MS m/z 325 (M+H)$^+$.

EXAMPLE 49

Synthesis of N-(2-hydroxy 3,4-difluorophenyl) N'-(2-bromophenyl)urea a) Synthesis of 2-hydroxy 3,4-difluoro aniline 2,3 difluoro 6-nitrophenol (2 g, 11 mmol) was treated with 10% Pd/C(1 g) at 23° C. The reaction mixture was flushed with hydrogen gas and the reaction was allowed to stir 12 h before it was filtered through celite. The filtrate was concentrated in vacuo to afforded the title compound (1.6 g, 97%). EI-MS m/z 146(M+H)$^+$.

b) Synthesis of N-(2-hydroxy 3,4-difluorophenyl) N'-(2-bromophenyl)urea

The urea was prepared from 2-hydroxy 3,4-difluoro aniline(0.290 g, 2 mmol) and 2-bromophenylisocyanate(0.4 g) by general Method B. It was purified by dilution with methylene chloride and precipitation with hexane(0.254 g, 37%). EI-MS m/z 343(M+H)$^+$.

EXAMPLE 50

Synthesis of N-(2-hydroxy 3-napthyl) N'-(2-bromophenyl)urea

The urea was prepared from 3-amino 2-hydroxy napthalene(0.320 g, 2 mmol) and 2-bromophenylisocyanate (0.40 g) by general Method B. It was purified by dilution of the with methylene chloride and precipitation with hexane (0.339, 47%). EI-MS m/z 357(M+H)$^+$.

EXAMPLE 51

Synthesis of N-(2-hydroxy 4-phenylphenyl) N'-(2-bromophenyl)urea a) Synthesis of 2-nitro 5-phenylphenol A solution of 3-phenyl phenol(2 g, 11 mmol) in acetic acid was treated with concentrated nitric acid drop-wise until all starting material was consumed. The solution was partitioned between water and methylene chloride. The organic phase was separated and the aqueous phase was extracted once more with methylene chloride. The combined organic phases were dried over sodium sulfate, filtered and concentrated in vacuo. The residue was purified by silica gel chromatography(ethyl acetate/hexanes) to afford desired (1.2 g, 50%). $^1$H NMR (CDCl$_3$): δ 10.65(s, 1H), 8.18 (d, 1H, J=10.0 Hz), 7.65 (d, 2H, J=6.0 Hz), 7.49 (m, 3H), 7.34 (s, 1H), 7.10 (d, 1H, J=10.0 Hz).

b) Synthesis of 2-amino 5-phenylphenol

A solution of 2-nitro 5-phenylphenol(1.2 g, 5.5 mmol) in methanol was treated with 10% Pd/C(1.2 g). The reaction mixture was flushed with hydrogen and allowed to stir overnight. The reaction mixture was filtered through celite and the filtrate was concentrated in vacuo to afford desired (1.01 g, 98%). EI-MS m/z 186(M+H)$^+$.

c) Synthesis of N-(2-hydroxy 4-phenylphenyl) N'-(2-bromophenyl)urea

The urea was prepared from 2-hydroxy 4-phenyl aniline (0.185 g, 1 mmol) and 2-bromophenylisocyanate(0.198 g) by general Method B. It was purified by dilution of the DMF solution with methylene chloride and precipitation with hexane(215 mg, 56%). EI-MS m/z 383(M+H)$^+$.

EXAMPLE 52

Synthesis of N-(2-hydroxy 4-methylphenyl) N'-(2-bromophenyl)urea

The urea was prepared from 2-hydroxy 4-methyl aniline (0.274 g, 2 mmol) and 2-bromo phenylisocyanate(0.40 g, 2 mmol) by general Method B. It was purified by dilution of the DMF solution with methylene chloride and precipitation with hexane(249 mg, 39%). EI-MS m/z 319(M−H)$^-$.

EXAMPLE 53

Synthesis of N(2-hydroxy 4-nitrophenyl) N'-(2-phenylaminophenyl)urea

The urea was synthesized by the treatment of 2-tertbutyldimethylsilyloxy 4-nitrophenyl isocyanate (example 9a, 0.419 g, 1.5 equiv.) with 2-anilino aniline (0.184 g, 1 equiv.) in THF overnight at 40° C. The desired product precipitated out of the reaction mixture(30 mg, 8%). EI-MS m/z 365(M+H)$^+$.

EXAMPLE 54

Synthesis of N-(2-hydroxy 3-carboxylate phenyl) N'-(2-bromophenyl)urea

The urea was prepared from 2-hydroxy 3-aminobenzoic acid(300 mg, 2 mmol) and 2-bromophenylisocyanate by general Method B. It was purified by dilution of the DMF solution with methylene chloride and precipitation with hexane(0.287 g, 41%). EI-MS m/z 351 (M+H)$^+$.

EXAMPLE 55

Synthesis of N(2-sulfhydryl 4-bromophenyl) N'-(2-bromophenyl)urea a)Synthesis of 2-amino 6-bromothiazole 4-Bromo aniline(4.3 g, 25 mmol, 1 equiv.) and ammonium thiocyanate(5.7 g, 3 equiv.) was dissolved in acetic acid and treated with bromine(4 g, 1 equiv.) at room temperature. After complete disappearance of starting material the reaction mixture was poured into water and the solid was collected. The solid was used in the next step without any purification(3.6 g, 46%). EI-MS m/z 229(M+H)$^+$.

b) Synthesis of bis (3-bromo 6-aminophenyl)disulfide

The 2-amino 6-bromothiazole hydrobromide (500 mg, 1.6 mmol) in water(5 mL) was treated with KOH (2.5 g) was heated at reflux for 8 h at reflux. The reaction mixture was then acidified to ph 4 with acetic acid and extracted with methylene chloride. The methylene chloride mixture was concentrated in vacuo. The residue was dissolved in DMSO and treated with $I_2$. After stirring overnight at room temperature the reaction mixture was partitioned between methylene chloride and saturated sodium bicarbonate. The methylene chloride layer was dried with magnesium sulfate and concentrated in vacuo. The resulting solid was purified by flash chromatography(ethyl acetate/hexane) to afford the title compound (230 mg, 34%). EI-MS m/z 405(M+H)$^+$.

c) Synthesis of N(2-sulfhydryl 4-bromophenyl) N'-(2-bromophenyl)urea

A solution of (3-bromo 6-aminophenyl) disulfide(201 mg, 0.5 mmol) in DMF was treated with 2-bromophenylisocyanate(1 mmol) at 80° C. overnight. The reaction mixture was diluted with methylene chloride and a solid was precipitated out with hexanes. The solution was dissolved in MeOH and treated with NaBH$_4$. After gas evolution ceased the reaction mixture was carefully acidified with 1N HCl and the resulting solid was filtered(52 mg, 13%). EI-MS m/z 399 (M–H)$^-$.

EXAMPLE 56

Synthesis of N-(2-hydroxy 4-nitrophenyl) N'-(2-iodophenyl)urea

The urea was synthesized by the treatment of 2-iodobenzoic acid(5 g, 20 mmol) with diphenyl phosphoryl azide(1 equiv.) and triethyl amine (1 equiv.) in DMF at 80° C. after gas evolution ceased the 5-nitro 2-aminophenol (3 g, 1 equiv.) was added. The reaction was heated overnight at 80° C. The reaction mixture was purified by filtering through a plug of silica with methylene chloride. The desired product was then precipitated out with hexane. Filtering afforded the desired compound(1.08 g, 13%). EI-MS m/z 398(M–H)$^-$.

EXAMPLE 57

Synthesis of N-(2-hydroxy 4-nitrophenyl) N'-(2-bromophenyl)thiourea

The thiourea was synthesized by treatment of the 2-tert-butyldimethylsilyloxy 4-nitro phenyl thioisocyanate(see example 9a, 3.73 mmol) with 2-bromo aniline in toluene at 88° C. over 36 h. The solution was concentrated and the residue was purified by flash chromatography(EtOAc/Hexanes). The fraction slightly lower rf than starting material contained the desired compound. This fraction was concentrated and then treated with triethyl amine hydrofluoride in acetonitrile for 15 minutes at 23° C. The reaction mixture was then concentrated in vacuo and the residue was purified by flash chromatography(ethyl actate/hexanes) to give N-(2-hydroxy 4-nitrophenyl) N'-(2-bromophenyl)thiourea(52 mg, 4%). EI-MS m/z 369(M+H)$^+$.

EXAMPLE 58

Synthesis of N-(2-phenylsulfamido) 4-cyanophenyl N'-(2-bromophenyl)urea a) Synthesis of 3-(phenylsulfamido)benzonitrile The of 3-(phenylsulfamido)benzonitrile was synthesized from the 3-cyano aniline (23.9 g, 0.2 mol) by Method C. It was purified by recrystalization from EtOH(15.8 g, 31%). $^1$H NMR (CDCl$_3$): δ 7.95(s, 1H), 7.84 (d, 2H, J=8.0 Hz), 7.59 (t, 1H, J=8.0 Hz), 7.45 (m, 2H), 7.35 (m, 4H).

b) Synthesis of 3-(phenylsulfamido) 4-nitrobenzonitrile

The 3-(phenylsulfamido)benzonitrile(10 g, 39 mmol) was dissolved in acetic anhydride and treated with concentrated nitric acid dropwise at room temperature until all the starting material had been consumed. The reaction mixture was then quenched by carefully pouring it into sodium bicarbonate and left to sit until all gas evolution had subsided. It was then partitioned between methylene chloride and water. The organic layer was dried over sodium sulfate and filtered. The reaction mixture was concentrated in vacuo, absorbed onto silica gel and purified by column chromatography (methylene chloride/hexane) to afford the title compound (1.7g, 15%). EI-MS m/z 302(M+H)$^+$.

c) Synthesis of 3-(phenylsulfamido) 4-aminobenzonitrile

The 3-(phenylsulfamido) 4-nitrobenzonitrile(1.5 g, 4.9 mmol) was treated with tin chloride dihydrate in EtOH at 80° C. for 12 h. It was then concentrated and flushed through a plug of silica gel with 5% methanol/methylene chloride. The filterate was absorbed onto silica gel and purified by flash chromatography(ethyl acetate/hexane) to afford the title compound (0.9 g, 60%). EI-MS m/z 274 (M+H)$^+$.

d) Synthesis of N-(2-phenylsulfamido) 4-cyanophenyl N'-(2-bromophenyl)urea

The urea was synthesized from 2-(phenylsulfamido) 4-aminobenzonitrile(77 mg, 0.28 mmol) and 2-bromophenylisocyanate by general Method C. It was purified by column chromatography(ethyl acetate/hexane) to afford the title compound (30 mg, 22%). EI-MS m/z 469 (M–H)$^-$.

EXAMPLE 59

Synthesis of N-(2-(phenylsulfamido)phenyl) N'-(2-bromophenyl)urea a) Synthesis of 2-(phenylsulfamido)aniline The sulfonamide was synthesized from phenylsulfonyl chloride(0.01 mmol) and o-phenylene diamine(1.08 g, 0.01 mmol) by general Method C. It was purified by recrystallization from EtOH(1.0 g, 40%). EI-MS m/z 249(M+H)$^+$.

b) Synthesis of N-(2-(phenylsulfamido)phenyl) N'-(2-bromophenyl)urea

The urea was synthesized 2-(phenylsulfamido)aniline(1 mmol) and 2-bromophenylisocyanate by general Method B. It was purified by dilution with methylene chloride and precipitation with hexane. Filtering afforded the desired compound(0.234 g, 52%). EI-MS m/z 446(M+H)$^+$.

EXAMPLE 60

Synthesis of N-(2-(styrylsulfamido)phenyl) N'-(2-bromophenyl)urea a) Synthesis of 2-(styrylsulfamido)aniline The sulfonamide was synthesized from styrylsulfonyl chloride(0.01 mol) and o-phenylene diamine(0.01 mol) by general Method C. It was purified by recrystallization from EtOH(1.2 g, 60%)EI-MS m/z 199(M+H)$^+$.

b) Synthesis of N-(2-(styrylsulfamido)phenyl) N'-(2-bromophenyl)urea

The urea was synthesized from 2-(styrylsulfamido) aniline(1 mmol) and 2-bromo phenylisocyanate(1 mmol) by general Method B. It was purified by dilution with methylene chloride and precipitation with hexane. Filtering afforded the desired compound(0.309 g, 65%). EI-MS m/z 472(M+H)$^+$.

EXAMPLE 61

Synthesis of 2-[(3,4 dimethoxyphenyl) sulfonylamino]phenyl) N'-(2-bromophenyl)urea a) Synthesis of 2-[(3,4-dimethoxyphenyl)sulfonylamino] phenyl aniline The sulfonamide was synthesized from 3,4-dimethoxy phenyl sulfonyl chloride(0.01 mol) and o-phenylene diamine by general Method C. It was purified by recrystallization from EtOH(0.65 g, 21%). EI-MS m/z 309(M+H)$^+$.

b) Synthesis of 2-[(3,4-dimethoxyphenyl)sulfonylamino] phenyl) N'-(2-bromophenyl)urea The urea was synthesized from 2-[(3,4-dimethoxyphenyl) sulfonylamino]phenyl aniline(1 mmol) and 2-bromophenylisocyanate by general Method B. It was purified by dilution with methylene chloride and precipitation with hexane. Filtering afforded the desired compound (0.062 g, 12%). EI-MS m/z 504(M−H)$^−$.

EXAMPLE 62

Synthesis of N-(2-[(4-acetamidophenyl) sulfonylamino]phenyl) N'-(2-bromophenyl)urea a) Synthesis of 2-[(4-acetamidophenyl)sulfonylamino] phenyl aniline The sulfonamide was synthesized from 4-acetamidophenyl sulfonyl chloride(0.01 mol) and o-phenylene diamine(0.01 mol) by general Method C. It was purified by recrystallization from EtOH(1.27 g,40%)EI-MS m/z 304(M−H)$^−$.

b) Synthesis of N-(2-[(4-acetamidophenylsulfonyl)amino] phenyl) N'-(2-bromophenyl)urea The urea was synthesized from 2-[(4-acetamidophenyl) sulfonylamino]phenyl aniline(1 mmol) and 2-bromophenylisocyanate(1 mmol) by general Method B. It was purified by dilution with methylene chloride and precipitation with hexane. Filtering afforded the desired compound(0.12 g, 24%). EI-MS mn/z 501(M−H)$^−$.

EXAMPLE 63

Synthesis of N-(2-(2-thiophenesulfamidophenyl) N'-(2-bromophenyl)urea a) Synthesis of 2-(2-thiophenesulfamido)aniline The sulfonamide was synthesized from 2-thiophenesulfonyl chloride(0.01 mol) and o-phenylene diamine(0.01 mol) by general Method C. It was purified by recrystallization from EtOH(0.77 g, 30%). EI-MS m/z 255 (M+H)$^+$.

b) Synthesis of N-(2-(2-thiophenesulfonylaminophenyl) N'-(2-bromophenyl)urea

The urea was synthesized from 2-(2-thiophenesulfonylamino) aniline(1 mmol) and 2-bromophenylisocyanate(1 mmol) by general Method B. It was purified by dilution with methylene chloride and precipitation with hexane. Filtering afforded the desired compound(0.29 g, 64%). EI-MS m/z 450(M−H)$^−$.

EXAMPLE 64

Synthesis of N-(2-(3-tolylsulfonylaminophenyl) N'-(2-bromophenyl)urea a) Synthesis of 2-(3-tolylsulfonylamino)aniline The sulfonamide was synthesized from 3-tolylsulfonyl chloride(0.01 mol) and o-phenylene diamine(0.01 mol) by general Method C. It was purified by recrystallization from EtOH(0.73g, 28%). EI-MS m/z 263 (M+H)$^+$.

b) Synthesis of N-(2-((3-tolylsulfonylamino)phenyl) N'-(2-bromophenyl)urea

The urea was synthesized from 2-(3-tolylsulfonylamino) aniline(1 mmol) and 2-bromophenylisocyanate(1 mmol) by general Method B. It was purified by dilution with methylene chloride and precipitation with hexanes. It was recrysallized two times with EtOH(25 mg, 5%). EI-MS m/z 458 (M−H)$^−$.

EXAMPLE 65

Synthesis of N-(2-(8-quinolinylsulfonylamino) phenyl) N'-(2-bromophenyl)urea a) Synthesis of 2-(8-quinolinylsulfonylamino)aniline The sulfonamide was synthesized from 8-quinolinyl sulfonyl chloride(0.01 mol) and o-phenylene diamine(0.01 mol) by general Method C. It was purified by recrystallization from EtOH(0.82 g, 27%). EI-MS m/z 300 (M+H)$^+$.

b) Synthesis of N-(2-((8-quinolinyl)sulfonylamino)phenyl) N'-(2-bromophenyl)urea The urea was synthesized from 2-((8-quinolinyl) sulfonylamino)aniline(1 mmol) and 2-bromophenylisocyanate(1 mmol) by general Method B. It was purified by dilution with methylene chloride and precipitation with hexane. Filtering afforded the desired compound(0.23 g, 46%). EI-MS m/z 495(M−H)$^−$.

EXAMPLE 66

Synthesis of N-(2-(benzylsulfonylamino)phenyl) N'-(2-bromophenyl)urea a) Synthesis of 2-(benzylsulfonylamino)aniline The sulfonamide was synthesized from benzylsulfonyl chloride(0.01 mol) and o-phenylene diamine(0.01 mol) by general Method C. It was purified by recrystallization from EtOH(0.87g, 33%). EI-MS m/z 263(M+H)+.

b) Synthesis of N-(2-(benzylsulfonylamino)phenyl) N'-(2-bromophenyl)urea

The urea was synthesized from 2-(benzylsulfonylamino) aniline(1 mmol) and 2-bromophenylisocyanate(1 mmol) by general Method B. It was purified by dilution with methylene chloride and precipitation with hexane. Filtering afforded the desired compound(0.11 g, 23%). EI-MS m/z 460 (M+H)+.

EXAMPLE 67

Synthesis of N-(2-hydroxy-4-azidophenyl)-N'-(2-methoxyphenyl)urea a) Synthesis of N-(2-hydroxy-4-aminophenyl)-N'-(2-methoxyphenyl)urea To a solution of N-(2-hydroxy-4-nitrophenyl)-N'-(2-methoxyphenyl)urea(1.0 g, example 15) in methanol, palladium (on activated carbon, 10%) (100 mg) was added. Then the reaction mixture was hydrogenated under a hydrogen balloon for 18 hours. The solid was filtered off by celite and washed three times by methanol. The filtrate was concentrated under reduced pressure to give amine compound (0.8 g, 89%). EI-MS m/z 274 (M+H)$^+$.

b) Synthesis of N-(2-hydroxy-4-azidophenyl)-N'-(2-methoxyphenyl)urea

The N-(2-hydroxy-4-aminophenyl)-N'-(2-methoxyphenyl)urea (300 mg, 1.17 mmol) was added to HCl/H$_2$O (1.17 mL/2.34 mL), cooled to 0° C. Sodium nitrite (80.7 mg, 1.17 mmol) was added to the reaction mixture. The reaction mixture was stirred at 0° C. for 30 minutes. The sodium azide (76 mg, 1.17 mmol) was added to reaction mixture and it was warmed to room temperature. The reaction mixture was stirred at room temperature for 18 hours. Then it was extracted with three times by ethyl acetate. The organic extracts were combined, dried over MgSO$_4$, filtered and concentrated under reduced pressure and chromatography of the resulting solid on silica gel (hexane:ethyl acetate; 5:1) gave product (125 mg, 38%). EI-MS m/z 300 (M+H)$^+$.

EXAMPLE 68

Preparation of N-[2-hydroxy-5-cyanophenyl]-N'-[2-bromophenyl]urea a) Preparation of 2-amino-4-cyanophenol To a solution of 2-nitro-4-cyanophenol(10 g, 61 mmol) in methanol(250 mL) was added 10% Pd/C (1 g). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(8.0 g, 97%). $^1$H NMR (CD$_3$OD): δ 6.96 (d, 1H), 6.90 (dd, 1H), 6.77 (d, 1H).

b) Preparation of N-[2-hydroxy-5-cyanophenyl]-N'-[2-bromophenyl]urea

N-[2-hydroxy-5-cyanophenyl]-N'-[2-bromophenyl]urea was prepared from 2-amino-4-cyanophenol(268 mg, 2.00 mmol) according to the procedure in General Method B. The product was purified by precipitation from methylene chloride/hexane(1/20) and filtering. (540 mg,81%). $^1$H NMR (CD$_3$OD): δ 8.10 (d, 1H), 7.87 (d, 1H), 7.43 (d, 1H), 7.20 (t, 1H), 7.09 (d, 1H), 6.86 (t, 1H), 6.77 (d, 1H).

EXAMPLE 69

Preparation of N-[2-hydroxy-3-fluorophenyl]-N'-[2-bromophenyl]urea a) Preparation of 2-amino-3-fluorophenol To a solution of 2-nitro-3-fluorophenol(1 g, 6.4 mmol) in methanol(250 mL) was added 10% Pd/C (1 g). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(650 mg, 80.2%). $^1$H NMR (CD$_3$OD): δ 6.41–6.17 (m, 3H).

b) Preparation of N-[2-hydroxy-3-fluorophenyl]-N'-[2-bromophenyl]urea

N-[2-Hydroxy-3-fluorophenyl]-N'-[2-bromophenyl]urea was prepared from 2-amino-3-fluorophenol (254 mg, 2.00 mmol) according to the procedure in General Method B. The product was purified by precipitation from methylene chloride/hexane(1/20) and filtering. (500 mg, 77%). $^1$H NMR (CD$_3$OD): δ 8.05 (d, 1H), 7.50 (d, 1H), 7.26 (t, 1H), 7.18 (d, 1H), 6.92 (t, 1H), 6.86–6.68 (m, 2H).

EXAMPLE 70

Preparation of N-2-[1-hydroxyfluorene]-N'-[2-bromophenyl]urea a) Preparation of 2-amino-1-hydroxyfluorene To a solution of 1-hydroxy-2-nitrofluorene(250 mg, 1.23 mmol) in methanol(250 mL) was added 10% Pd/C (1 g). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(171 mg, 81.2%). $^1$H NMR (CD$_3$OD): δ 7.60 (d, 1H), 7.47 (d, 1H), 7.28 (t, 1H), 7.18 (m, 2H), 6.82 (d, 1H), 3.76 (s, 2H).

b) Preparation of N-2-[1-hydroxyfluorene]-N'-[2-bromophenyl]urea

N-2-[1-hydroxyfluorene]-N'-[2-bromophenyl]urea was prepared from 2-amino-1-hydroxyfluorene (170 mg, 0.86 mmol) according to the procedure in General Method B. The product was purified by chromatography of the resulting solid on silica gel (30% EtOAc/Hexane) to give the desired product (300 mg, 84.5%). $^1$H NMR (CD$_3$Cl): δ 8.04 (d, 1H), 7.66 (d, 1H), 7.49 (t, 2H), 7.35–7.20 (m, 4H), 7.09 (d, 1H), 6.90 (t, 1H).

EXAMPLE 71

Preparation of N-3-[2-hydroxy-9,10-anthraquinonyl]-N'-[2-bromophenyl]urea

N-3-[2-Hydroxy-9,10-anthraquinonyl]-N'-[2-bromophenyl]urea was prepared from 2-hydroxy-3-aminoanthraquinone(480 mg, 2.00 mmol) according to the procedure in General Method B. The product was purified by precipitation from methylene chloride/hexane(1/20) and filtering. (610 mg, 70%). $^1$H NMR (CD$_3$OD): δ 8.93 (s,1H), 8.12 (m, 2H), 8.02 (d, 1H), 7.77 (m, 2H), 7.61 (d, 1H), 7.52 (s, 1H), 7.38 (t, 1H), 7.05 (t, 1H).

EXAMPLE 72

Preparation of N-[2-hydroxy-3-fluoro-5-bromophenyl]-N'-[2-bromophenyl]urea a) Preparation of 2-amino-6-fluoro-bromophenol A mixture of 4bromo-2-fluoro 6-nitrophenol(1 g, 4.2 mmol) and tin (II) chloride (4.78 g, 21.2 mmol) in ethanol (50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(710 mg, 82%). $^1$H NMR (CD$_3$QD): δ 6.51–6.40 (m, 2H).

b) Preparation of N-[2-hydroxy-3-fluoro-5-bromophenyl]-N'-[2-bromophenyl]urea

N-[2-hydroxy-3-fluoro-5-bromophenyl]-N'-[2-bromophenyl]urea was prepared from 2-amino-6-fluoro-4-bromophenol (254 mg, 2.00 mmol) according to the procedure in General Method B. The product was purified by precipitation from methylene chloride/hexane(1/20) and filtering. (500 mg, 77%). $^1$H NMR (CD$_3$OD): δ 7.98 (s, 1H), 7.91 (d, 1H), 7.60 (d, 1H), 7.33 (t, 1H), 7.00 (t, 1H), 6.94 (d, 1H).

EXAMPLE 73

Preparation of N-[2-hydroxy-3-chlorophenyl]-N'-[2-bromophenyl]urea a) Preparation of 2-amino-3-chlorophenol A mixture of 3-chloro-2-nitrophenol(250 mg, 1.4 mmol) and tin (II) chloride (1.2 g, 5.3 mmol) in ethanol(50 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product(143 mg, 69%). $^1H$ NMR ($CD_3OD$): δ 6.75 (t,1H), 6.70 (d, 1H), 6.65 (d, 1H).

b) Preparation of N-[2-hydroxy-3-chlorophenyl]-N'-[2-bromophenyl]urea

N-[2-hydroxy-3-chlorophenyl]-N'-[2-bromophenyl]urea was prepared from 2-amino-3-chlorophenol (143 mg, 1.00 mmol) according to the procedure in General Method B. The product was purified by chromatography of the resulting solid on silica gel (30% EtOAc/Hexane) to give the desired product(195 mg, 57%). $^1H$ NMR ($CD_3OD$): δ 7.81 (d, 1H), 7.68 (d, 1H), 7.47 (d, 1H), 7.20 (t, 1H), 6.90 (m, 2H), 6.70 (t, 1H).

EXAMPLE 74

Preparation of N-[2-hydroxy-3-trifluoromethylphenyl]-N'-[2-bromophenyl]urea a) Preparation of 2-nitro-6-trifluoromethylphenol 2-tifluoromethylphenol (3.00 g, 18.5 mmol) was dissolved in methylene chloride(40 mL) followed by the addition of sodium nitrate (1.73 g, 20.4 mmol). The addition of sulfuric acid (23 mL/3M) was then made, followed by addition of a catalytic amount of sodium nitrite. The mixture was allowed to stir. After 24 hours, the reaction mixture was diluted with methylene chloride and extracted with water. The organic layer was dried over $MgSO_4$ and filtered. The solvent was evaporated and chromatography of the resulting solid on silica gel (4% $MeOH/CH_2Cl_2$) gave the desired product(1.84 g, 47%). $^1H$ NMR ($CD_3COCD_3$): δ 8.35 (d,1H), 7.95 (d, 1H), 7.13 (t, 1H).

b) Preparation of 2-amino-6-trifluoromethylphenol

A mixture of 6-trifluoromethyl-2-nitrophenol(1.84 g, 8.67 mmol) and tin (II) chloride (6.0 g, 26.2 mmol) in ethanol (150 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product(1.35 g, 88%). $^1H$ NMR ($CD_3OD$): δ 6.93 (d, 1H), 6.82 (t, 1H), 6.78 (d, 1H).

c) Preparation of N-[2-hydroxy-3-trifluoromethylphenyl]-N'-[2-bromophenyl]urea

N-[2-hydroxy-3-trifluoromethylphenyl]-N'-[2-bromophenyl]urea was prepared from 2-amino-6-trifluoromethylphenol (280 mg, 1.60 mmol) according to the procedure in General Method B. The product was purified by precipitation from methylene chloride/hexane(1/20) and filtering. (390 mg, 65%). $^1H$ NMR ($CD_3OD$): δ 7.99 (d, 1H), 7.60 (d, 1H), 7.58 (d, 1H), 7.34 (t, 1H), 7.30 (d, 1H), 7.00 (t, 1H), 6.96 (d, 1H).

EXAMPLE 75

Preparation of N-[3,4 diphenyl-2-hydroxyphenyl]-N'-[2-bromophenyl]urea

N-[3,4 diphenyl-2-hydroxyphenyl]-N'-[2-bromophenyl]urea was prepared from 2-amino-5,6 diphenylphenol (50 mg, 0.19 mmol) according to the procedure in General Method B. The product was purified by precipitation from methylene chloride/hexane(1/20) and filtering (61 mg, 69%). $^1H$ NMR ($CD_3OD$): δ 7.97 (d, 1H), 7.66 (d, 1H), 7.58 (d, 1H), 7.31 (t, 1H), 7.25–7.00 (m, 11H), 6.91 (d, 1H).

EXAMPLE 76

Preparation of N-[2-hydroxy-3-glycinemethylestercarbonylphenyl]-N'-[2-bromophenyl]urea N-[2-hydroxy-3-glycinemethylestercarbonylphenyl]-N'-[2-bromophenyl]urea was prepared from 6-glycinemethylestercarbonyl-2-aminophenol (50 mg, 0.22 mmol), purchased from the University of New Hampshire, according to the procedure in General Method B. The product was purified by precipitation from methylene chloride/hexane(1/20) and filtering (65 mg, 69%). $^1H$ NMR ($CD_3OD$): δ 8.14 (d, 1H), 7.96 (d, 1H), 7.49 (d, 1H), 7.24 (t, 2H), 6.89 (dd, 1H), 6.81 (t, 1H), 4.10 (s,2H), 3.74 (s,3H).

EXAMPLE 77

Preparation of N-[2-hydroxy-3-glycinecarbonylphenyl]-N'-[2-bromophenyl]urea

N-[2-Hydroxy-3-glycinecarbonylphenyl]-N'-[2-bromophenyl]urea was prepared from N-[2-hydroxy-3-glycinemethylestercarbonylphenyl]-N'-[2-bromophenyl]urea(50 mg, 0.12 mmol) by stirring in a 3/1 ratio of methano/water (10 mL). Addition of 1 equiv. of lithium hydroxide was added and stirring continued until the starting material had disappeared. (45 mg, 92%). The product was purified by chromatography of the resulting solid on silica gel (9/1/0.1 $CH_2C_2/MeOH/AcOH$) to give the desired product(195 mg, 57%). $^1H$ NMR ($CD_3OD$): δ 8.14 (d, 1H), 7.92 (d, 1H), 7.60 (d, 1H), 7.46 (d, 1H), 7.34 (t, 1H), 7.04 (t, 1H), 6.82 (t, 1H), 3.96 (2H).

EXAMPLE 78

Preparation of N-[2-hydroxy-3,5-dichlorophenyl]-N'-[2-bromophenyl]urea a) Preparation of 2-amino-4,6-dichlorophenol A mixture of 4,6-dichloro-2-nitrophenol(1 g, 4.8 mmol) and tin (II) chloride (3.2 g, 14.4 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product(685 mg, 80%). $^1H$ NMR ($CD_3OD$): δ 6.75 (s,1H), 6.61 (s, 1H).

b) Preparation of N-[2-hydroxy-3,5-dichlorophenyl]-N'-[2-bromophenyl]urea

N-[2-Hydroxy-3,5dichlorophenyl]-N'-[2-bromophenyl)urea was prepared from 2-amino-4,6-dichlorophenol (143 mg, 1.00 mmol) according to the procedure in General Methbd B. The product was purified by precipitation from methylene chloride/hexane(1/20) and filtering. (660 mg, 88%). $^1$H NMR (CD$_3$OD): δ 7.96 (s, 1H), 7.89 (d, 1H), 7.60 (d, 1H), 7.35 (t, 1H), 7.00 (t, 1H), 6.95 (dd, 1H).

EXAMPLE 79

Preparation of N-[2-hydroxy-3-nitrophenyl]-N'-[2-bromophenyl]urea

N-[2-Hydroxy-3-nitrophenyl]-N'-[2-bromophenyl]urea was prepared from 2-hydroxy-3-nitroaniline (1.25 g, 8.1 mmol) according to the procedure in General Method B. The product was purified by precipitation from methylene chloride/hexane(1/20) and filtering. (2.4 g, 84%). $^1$H NMR (CD$_3$OD): δ 8.45 (d, 1H), 7.94 (d, 1H), 7.78 (d, 1H), 7.60 (d, 1H), 7.35 (t, 1H), 7.01 (m, 2H).

EXAMPLE 80

Preparation of N-[2-hydroxy-4-naphthalenesulfonic acid]-N'-[2-bromophenyl]urea

N-[2-hydroxy-4-naphthalenesulfonic acid]-N'-[2-bromophenyl]urea was prepared from 1-amino-2-hydroxy-4-naphthalensulfonic acid (0.48 g, 2.0 mmol) according to the procedure in General Method B and the addition of 1 mL of triethylamine. The product was purified by precipitation from methylene chloride/hexane(1/20) and filtering. (690 mg, 79%). $^1$H NMR (CD$_3$OD): δ 8.14 (s, 1H), 8.04 (d, 1H), 7.98 (m, 2H), 7.61–7.55 (m, 3H), 7.43 (t, 1H), 6.98 (t, 1H).

EXAMPLE 81

Preparation of N-[2-hydroxy-5-naphthalenesulfonic acid]-N'-[2-bromophenyl]urea

N-3-[2-hydroxy-5-naphthalensulfonic acid]-N'-[2-bromophenyl]urea was prepared from 2-amino-3-hydroxy-6-naphthalensulfonic acid (0.48 g, 2.0 mmol) according to the procedure in General Method B and the addition of 1 mL of triethylamine. The product was purified by precipitation from methylene chloride/hexane(1/20) and filtering. (715 mg, 82%). $^1$H NMR (CD$_3$OD): δ 8.09 (s, 1H), 7.96 (d, 1H), 7.65–7.48 (m, 3H), 7.36 (t, 1H), 7.25 (s, 1H), 7.04 (m, 2H).

EXAMPLE 82

Preparation of N-[2-hydroxy-3,4-dichlorophenyl]-N'-[2-bromophenyl]urea a) Preparation of 2-nitro-5,6 dichlorophenol 2,3-dichlorophenol (3.26 g, 20 mmol) was dissolved in methylene chloride(40 mL) followed by the addition of sodium nitrate (1.88 g, 22 mmol). The addition of sulfuric acid (20 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.8 g, 44%). $^1$H NMR (CD$_3$COCD3): δ 8.04 (d,1H), 7.15 (d, 1H).

b) Preparation of 2-amino-5,6 dichlorophenol

A mixture of 5,6-dichloro-2-nitrophenol(1.8 g, 8.7 mmol) and tin (II) chloride (5.8 g, 26.1 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(1.4 mg, 90%). $^1$H NMR (CD$_3$OD): δ 6.71 (d, 1H), 6.45 (d, 1H).

c) Preparation of N-[2-hydroxy-3,4-dichlorophenyl]-N'-[2-bromophenyl]urea

N-[2-Hydroxy-3,4-dichlorophenyl]-N'-[2-bromophenyl]urea was prepared from 2-amino-5,6-dichlorophenol (350 mg, 2.00 mmol) according to the procedure in General Method B. The product was purified by precipitation from methylene chloride/hexane(1/20) and filtering. (670 mg, 89%). $^1$H NMR (CD$_3$OD): δ 7.90 (d, 1H), 7.85 (d, 1H), 7.59 (d, 1H), 7.31 (t, 1H), 6.99 (t, 1H), 6.96 (d, (1H).

EXAMPLE 83

Preparation of N-[2-hydroxy-3-cyanophenyl]-N'-[2-bromophenyl]urea a) Preparation of 2-nitro-6cyanophenol 2-cyanophenol (2.38 g, 20 mmol) was dissolved in methylene chloride(40 mL) followed by the addition of sodium nitrate (1.88 g, 22 mmol). The addition of sulfuric acid (20 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.4 g, 42%). $^1$H NMR (CD$_3$COCD3): δ 8.47 (d,1H), 8.15 (d, 1H), 7.30 (t, 1H).

b) Preparation of 2-amino-6-cyanophenol

A mixture of 6-cyano-2-nitrophenol(600 mg, 1.0 mmol) and tin (II) chloride (3.2 g, 14.4 mmol) in acetic acid(50 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(365 mg, 75%). $^1$H NMR (CD$_3$OD): δ 6.92 (d, 1H), 6.85–6.69 (m,2H).

c) Preparation of N-[2-hydroxy-3-cyanophenyl]-N'-[2-bromophenyl]urea

N-[2-Hydroxy-3-cyanophenyl]-N'-[2-bromophenyl]urea was prepared from 2-amino-6-cyanophenol (134 mg, 1.00 mmol) according to the procedure in General Method B. The product was purified by precipitation from methylene chloride/hexane(1/20) and filtering. (260 mg, 78%). $^1$H NMR (CD$_3$OD): δ 7.98 (d, 1H), 7.74 (d, 1H), 7.57 (d, 1H), 7.30 (t, 1H), 7.22 (d, 1H), 6.98 (t, 1H), 6.94 (t, (1H).

EXAMPLE 84

Preparation of N-[2-hydroxy-4-cyanophenyl]-N'-[2-bromophenyl]urea a) Preparation of 2-nitro-5-cyanophenol 3-cyanophenol (2.38 g, 20 mmol) was dissolved in methylene chloride(40 mL) followed by the addition of sodium nitrate (1.88 g, 22 mmol). The addition of sulfuric acid (20 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(910 mg, 28%). $^1$H NMR (CD3COCD$_3$): δ 8.30 (d,1H), 7.67 (s,1H), 7.49 (d, 1H).

b) Preparation of 2-amino-5-cyanophenol

A mixture of 5-cyano-2-nitrophenol(250 mg, 1.5 mmol) and tin (II) chloride (3.2 g, 14.4 mmol) in ethanol(50 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(175 mg, 86%). $^1$H NMR (CD$_3$OD): δ 7.00 (d, 1H), 6.88 (s,1H), 6.69 (d, 1H).

c) Preparation of N-[2-hydroxy-4cyanophenyl]-N'-[2-bromophenyl]urea

N-[2-Hydroxy-4-cyanophenyl]-N'-[2-bromophenyl]urea was prepared from 2-amino-5-cyanophenol (170 mg, 1.27 mmol) according to the procedure in General Method B. The product was purified by precipitation from methylene chloride/hexane(1/20) and filtering (310 mg, 74%). $^1$H NMR (CD$_3$OD): δ 8.25 (d, 1H), 7.91 (d, 1H), 7.59 (d, 1H), 7.33 (t, 1H), 7.17 (d, 1H), 7.07 (s, 1H), 7.01 (t, (1H).

EXAMPLE 85

Preparation of N-[2-hydroxy-4-cyanophenyl]-N'-[4-methoxyphenyl]urea

N-[2-Hydroxy-4-cyanophenyl]-N'-[4-methoxyphenyl]urea was prepared from 2-amino-5-cyanophenol (60 mg, 0.45 mmol) according to the procedure in General Method B. The product was purified by precipitation from methylene chloride/hexane(1/20) and filtering. (110 mg,86%). $^1$H NMR (CD$_3$OD): δ 8.23 (d, 1H), 7.61–7.51 (m, 2H), 7.32 (d, 1H), 7.20 (d, 1H), 7.15 (d, 1H), 7.03 (s, 1H).

EXAMPLE 86

Preparation of N-[2-hydroxy-4-cyanophenyl]-N'-[2-phenylphenyl]urea

N-[2-Hydroxy-4-cyanophenyl]-N'-[2-phenylphenyl]urea was prepared from 2-amino-5-cyanophenol (170 mg, 1.27 mmol) according to the procedure in General Method B. The product was purified by precipitation from methylene chloride/hexane(1/20) and filtering. (150 mg, 85%). $^1$H NMR (CD$_3$OD): δ 8.20 (d, 1H), 7.73 (d, 1H), 7.51–7.20 (m, 8H), 7.13 (d, 1H), 7.01 (s, 1H).

EXAMPLE 87

Preparation of N-[2-hydroxy-4-cyanophenyl]-N'-[2-methylphenyl]urea

N-[2-Hydroxy-4-cyanophenyl]-N'-[2-methylphenyl]urea was prepared from 2-amino-5-cyanophenol (60 mg, 0.45 mmol) according to the procedure in General Method B. The product was purified by precipitation from methylene chloride/hexane(1/20) and filtering. (90 mg, 75%). $^1$H NMR (CD$_3$OD): δ 8.25 (d, 1H), 7.59 (d, 1H), 7.26–7.00 (m, 5H), 2.30 (s, 3H).

EXAMPLE 88

Preparation of N-[2-hydroxy-4-cyanophenyl]-N'-[2-trifluoromethylphenyl]urea

N-[2-Hydroxy-4-cyanophenyl]-N'-[2-trifluoromethylphenyl]urea was prepared from 2-amino-5-cyanophenol (60 mg, 0.45 mmol) according to the procedure in General Method B. The product was purified by precipitation from methylene chloride/hexane(1/20) and filtering. (110 mg, 76%). $^1$H NMR (CD$_3$OD): δ 8.25 (d, 1H), 7.81 (d, 1H), 7.68 (d, 1H), 7.61 (t, 1H), 7.32 (t, 1H), 7.15 (dd, 1H), 7.09 (s, (1H).

EXAMPLE 89

Preparation of N-[2-hydroxy-4-cyanophenyl]-N'-[3-trifluoromethylphenyl]urea

N-[2-hydroxy-4-cyanophenyl]-N'-[3-trifluoromethylphenyl]urea was prepared from 2-amino-5-cyanophenol (60 mg, 0.45 mmol) according to the procedure in General Method B. The product was purified by precipitation from methylene chloride/hexane(1/20) and filtering. (114 mg, 79%). $^1$H NMR (CD$_3$OD): δ 8.30 (d, 1H), 7.92 (s, 1H), 7.60 (d, 1H), 7.47 (t, 1H), 7.29 (d, 1H), 7.18 (dd, 1H), 7.06 (s, 1H).

EXAMPLE 90

Preparation of N-[2-hydroxy-4-cyanophenyl]-M-[4-trifluoromethylphenyl]urea

N-[2-Hydroxy-4-cyanophenyl]-N'-[4-trifluoromethylphenyl]urea was prepared from 2-amino-5-cyanophenol (60 mg, 0.45 mmol) according to the procedure in General Method B. The product was purified by precipitation from methylene chloride/hexane(1/20) and filtering. (108 mg, 75%). $^1$H NMR (CD$_3$OD): δ 8.31 (d, 1H), 7.68 (d, 2H), 7.59 (d, 2H), 7.20 (dd, 1H), 7.07 (s, 1H).

EXAMPLE 91

Preparation of N-[2-hydroxy-3-n-propylphenyl]-N'-[2-bromophenyl]urea a) Preparation of 2-nitro-6-n-propylphenol 2-n-propylphenol (5.00 g, 36.8 mmol) was dissolved in methylene chloride(40 mL) followed by the addition of sodium nitrate (3.43 g, 40.5 mmol). The addition of sulfuric acid (45 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(3.2 mg, 48%). $^1$H NMR (CD3COCD$_3$): δ 7.99 (d,1H), 7.46 dd, 1H), 6.90 (t, 1H), 2.70 (t, 2H), 1.70 (m, 2H), 1.00 (t, 3H).

b) Preparation of 2-amino-6-n-propylphenol

To a solution of 2-nitro-6-n-propylphenol(2 g, 11.0 mmol) in methanol(100 mL) was added 10% Pd/C (200 mg). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH(CH$_2$Cl$_2$) gave the desired product(1.50 g, 80.2%). $^1$H NMR (CD$_3$OD): δ 6.65 (m, 2H), 6.55 (t, 1H), 2.58 (t, 2H), 1.61 (m, 2H), 0.96 (t, 3H).

c) Preparation of N-[2-hydroxy-3-n-propylphenyl]-N'-[2-bromophenyl]urea

N-[2-Hydroxy-3-n-propylphenyl]-M-[2-bromophenyl]urea was prepared from 2-amino-6-n-propylphenol (302 mg, 2.00 mmol) according to the procedure in General Method B. The product was purified by precipitation from methylene chloride/hexane(1/20) and filtering. (640 mg,92%). $^1$H NMR (CD$_3$OD): δ 8.00 (d, 1H), 7.58 (d, 1H), 7.32 (t, 1H), 7.26 (t, 1H), 6.96 (dd, 1H), 6.89 (t, 1H), 6.78 (d, 1H).

EXAMPLE 92

Preparation of N-[2-hydroxy-4-ethylphenyl]-N'-[2-bromophenyl]urea a) Preparation of 2-nitro-5-ethylphenol 3-ethylphenol (5.00 g, 41 mmol) was dissolved in methylene chloride(40 mL) followed by the addition of sodium nitrate (3.83 g, 45 mmol). The addition of sulfuric acid (50 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.7 g, 25%). $^1$H NMR (CD3COCD$_3$): δ 8.02 (d,1H), 6.99 (s,1H), 6.85 (d, 1H), 2.69 (q, 2H), 1.30 (t, 3H).

b) Preparation of 2-amino-5-ethyllphenol

To a solution of 2-nitro-5-ethylphenol(1 g, 6.4 mmol) in methanol(250 mL) was added 10% Pd/C (100 mg). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(750 mg, 91%). $^1$H NMR (CD$_3$OD): δ 6.41–6.17 (m, 3H).

c) Preparation of N-[2-hydroxy-4-ethylphenyl]-N'-[2-bromophenyl]urea

N-[2-Hydroxy-4-ethylphenyl]-N'-[2-bromophenyl]urea was prepared from 2-amino-5-ethylphenol (274 mg, 2.00 mmol) according to the procedure in General Method B. The product was purified by precipitation from methylene chloride/hexane(1/20) and filtering. (520 mg, 77%). $^1$H NMR (CD$_3$OD): δ 7.96 (d, 1H), 7.62 (s, 1H), 7.56 (d, 1H), 7.30 (t, 1H), 6.96 (t, 1H), 6.82 (d, 1H), 6.76 (d, 1H).

EXAMPLE 93

Preparation of N-[2-hydroxy 3-phenylaminocarbonylphenyl]-N'-[2-bromophenyl]urea a) Preparation of 2-nitro-6-phenylaminocarbonylphenol 2-Phenylaminocarbonylphenol (5.00 g, 23 mmol) was dissolved in methylene chloride(40 mL) followed by the addition of sodium nitrate (2.20 g, 25.5 mmol). The addition of sulfuric acid (30 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(2.50 g, 42%). $^1$H NMR (CD3COCD$_3$): δ 8.15 (d,1H), 8.09 (d,1H), 7.51 (d, 1H), 7.30 (d, 1H), 7.10 (t, 1H), 7.01 (t, 1H).

b) Preparation of 2-amino-6-phenylaminocarbonylphenol

To a solution of 2-nitro-6-phenylaminocarbonylphenol (1 g, 4.0 mmol) in methanol(250 mL) was added 10% Pd/C (100 mg). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(800 mg, 91%). $^1$H NMR (CD$_3$OD): δ 7.73–7.57 (m, 2H), 7.43–7.27 (m, 3H), 7.25–7.10 (m, 1H), 6.94 (t, 1H), 6.74 (t, 1H).

c) Preparation of N-[2-hydroxy 3-phenylaminocarbonylphenyl]-N'-[2-bromophenyl]urea N-[2-hydroxy 3-Phenylaminocarbonylphenyl]-N'-[2-bromophenyl]urea was prepared from 2-amino-6-phenylaminocarbonylphenol (456 mg, 2.00 mmol) according to the procedure in General Method B. The product was purified by precipitation from methylene chloride/hexane(1/20) and filtering. (800 mg, 94%). $^1$H NMR (CD$_3$OD): $^1$H NMR (CD$_3$OD): δ 25 (d, 1H), 7.94 (d, 1H), 7.75–7.57 (m, 4H), 7.48–7.30 (m, 3H), 7.21 (t, 1H), 7.02 (dd, 1H), 6.92 (t, 1H).

EXAMPLE 94

Preparation of N-[2-hydroxy-3-cyano-4-methylphenyl]-N'-[2-bromophenyl]urea a) Preparation of the 2-nitro 5-methyl 6-bromophenol A solution of t-butyl amine(6.88 mL, 4.79 g, 2 equiv.) in methylene chloride was treated with bromine (1.67 mL, 5.2 g, 1 equiv.) at −20° C. The flask was then cooled to −78° C. and the the 2-nitro 5-methyl 6-bromophenol (5 g, 1 equiv., in methylene chloride) was added drop-wise with vigrous stirring. The reaction mixture was slowly warmed to −30° C. for 1 h, then to −10° C. for 2 hours. The reaction mixture was then partitioned between methylene chloride and 5% aqueous acetic acid. The organic layer was dried over magnesium sulfate, filtered and concentrated in vacuo. The reaction mixture was purified by flash chromatography(Ethyl acetate/hexanes) to remove dibrominated species. The 2-nitro 4-bromo 5-methyl phenol was then selectively crystallized out of methylene chloride. A final silica gel column(5% ethyl acetate/hexanes) yielded desired isomer in 90% puirty.(1.05 g, 14%). $^1$H NMR (CDCl$_3$): δ 7.95 (d, 1H, J=10.0 Hz), 6.91 (d, 1H, J=10.0 Hz), 2.52 (s, 3H).

b) Preparation of 2-nitro-5-methyl-6-cyanophenol

2-Nitro-5-methyl-6-bromophenol (100 mg, 0.433 mmol) was dissolved in dimethyl formamide (2 mL) followed by the addition of triethylamine (0.175 g, 1.73 mmol). The addition of a catalytic amount dimethylamino pyridine was then made, followed by addition of copper (I) cyanide (155 mg, 1.73 mmol). The mixture was allowed to stir at 80° C. for 4 hours. The solvent was evaporated and chromatography of the resulting solid on silica gel (2% MeOH/CH$_2$Cl$_2$) gave the desired product (70 mg, 91%). $^1$H NMR (CD3COCD$_3$): δ 8.30 (d, 1H), 7.15 (d,1H), 2.61 (s, 3H).

c) Preparation of 2-amino-5-methyl 6-cyanophenol

A mixture of 5-cyano-2-nitrophenol(70 mg, 0.39 mmol) and tin (II) chloride (265 mg, 1.18 mmol) in ethanol(20 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(175 mg, 86%). $^1$H NMR (CD$_3$OD): δ 6.87 (d, 1H), 6.75 (d,1H), 6.32 (s, 3H).

d) Preparation of N-[2-hydroxy 3-cyano 4-methylphenyl]-N'-[2-bromophenyl]urea

N-[2-hydroxy 3-cyano 4-methylphenyl]-N'-[2-bromophenyl]urea was prepared from 2-amino-5-methyl-6-cyanophenol (50 mg, 0.34 mmol) according to the procedure in General Method B. The product was purified by precipitation from methylene chloride/hexane(1/20) and filtering. (70 mg, 60%). $^1$H NMR (CD$_3$OD): δ 7.92 (d, 1H), 7.68 (d, 1H), 7.59 (d, 1H), 7.31 (t, 1H), 7.00 (t, 1H), 6.62 (t, 1H), 2.49 (s, (3H).

EXAMPLE 95

Preparation of N-[2-hydroxy 4-Carboxyphenylphenyl]-N'-[2-bromophenyl]urea a) Preparation of 4-nitro-3-hydroxybenzophenone 3-Hydroxybenzophenone (3.00 g, 15.1 mmol) was dissolved in methylene chloride(40 mL) followed by the addition of sodium nitrate (1.42 g, 16.7 mmol). The addition of sulfuric acid (25 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.10 g, 30%). $^1$H NMR (CD3COCD$_3$): δ 8.25 (d,1H), 7.86 (d,1H), 7.71 (m, 1H), 7.59 (d, 1H), 7.48 (s, 1H), 7.39 (dd, 1H).

b) Preparation of 4-amino-3-hydroxybenzophenone

A mixture of 4-nitro-3-hydroxybenzophenone (900 mg, 3.7 mmol) and tin (II) chloride (2.5 g, 11.1 mmol) in ethanol(50 mL) was heated at 80° C. under argon. After 2 hours, the starting material has disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(685 mg, 87%). $^1$H NMR (CD$_3$OD): δ 7.65 (d, 2H), 7.55 (d,1H), 7.49 (t, 2H), 7.26 (s, 1H), 7.16 (dd, 1H), 6.68 (d, 1H).

c) Preparation of N-[4-Carboxyphenyl-2-hydroxyphenyl]-N'-[2-bromophenyl]urea

N-[4-Carboxyphenyl-2-hydroxyphenyl]-N'-[2-bromophenyl]urea was prepared from 4-amino-3-hydroxybenzophenone (330 mg, 1.5 mmol) according to the procedure in General Method B. The product was purified by precipitation from methylene chloride/hexane(1/20) and filtering. (490 mg, 79%). $^1$H NMR (CD$_3$OD): δ 8.40 (d, 1H), 8.09 (d, 1H), 7.83 (d, 2H), 7.65–7.60 (m, 4H), 7.48 (s, 1H), 7.43 (d, 1H), 7.35 (d, (1H), 7.10 (t,1H).

EXAMPLE 96

Preparation of N-[2-hydroxy 3-carboxyphenylphenyl]-N'-[2-bromophenyl]urea a) Preparation of 3-nitro-2-hydroxybenzophenone 2-Hydroxybenzophenone (3.00 g, 15.1 mmol) was dissolved in methylene chloride(40 mL) followed by the addition of sodium nitrate (1.42 g, 16.7 mmol). The addition of sulfuric acid (25 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.60 g, 44%). $^1$H NMR (CD3COCD$_3$): δ 8.30 (d,1H), 7.86 (m,3H), 7.71 (m, 1H), 7.78 (d, 1H), 7.56 (dd 2H), 7.24 (t, 1H).

b) Preparation of 3-amino-2-hydroxybenzophenone

A mixture of 3-nitro-2-hydroxybenzophenone (600 mg, 2.5 mmol) and tin (II) chloride (1.7 g, 7.5 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH(CH$_2$Cl$_2$) gave the desired product(490 mg, 92%). $^1$H NMR (CD$_3$OD): δ 7.65–7.40 (m, 5H), 6.98 (d,1H), 6.86 (d, 1H), 6.67 (t, 1H).

c) Preparation of N-[2-hydroxy 3-carboxyphenylphenyl]-N'-[2-bromophenyl]urea

N-[2-hydroxy 3-carboxyphenylphenyl]-N'-[2-bromophenyl]urea was prepared from 3-amino-2-hydroxybenzophenone (250 mg, 1.20 mmol) according to the procedure in General Method B. The product was purified by precipitation from methylene chloride/hexane(1/20) and filtering. (200 mg, 78%). $^1$H NMR (CD$_3$OD): δ 8.35 (d, 1H), 7.96 (d, 1H), 7.72 (d, 2H), 7.65–7.50 (m, 4H), 7.35 (d, 1H), 7.30 (d, 1H), 7.01 (dd, (1H), 6.92 (t, 1H).

EXAMPLE 97

Preparation of N-[2-hydroxy 3-benzyloxyphenyl]-N'-[2-bromophenyl]urea a) Preparation of 2-nitro-6-benzyloxyphenol 2-Benzyloxyphenol (5.00 g, 25.0 mmol) was dissolved in methylene chloride(40 mL) followed by the addition of sodium nitrate (2.30 g, 27.5 mmol). The addition of sulfuric acid (31 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(2.6 g, 43%). $^1$H NMR (CD3COCD$_3$): δ 7.70 (d,1H), 7.50–7.28 (m, 5H), 7.14 (d, 1H), 6.92 (t, 1H), 5.21 (s, 2H).

b) Preparation of 2-amino-6-benzyloxyphenol

A mixture of 2-nitro-6-benzyloxyphenol (1.00 g, 4.10 mmol) and tin (II) chloride (2.75 g, 12.2 mmol) in ethanol (150 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(1.35 g, 88%). $^1$H NMR (CD$_3$OD): δ7.46 (d, 2H), 7.40–7.35 (m, 5H), 6.55 (d, 1H), 6.40 (d, 1H), 5.10 (s, 2H).

b) Preparation of N-[2-hydroxy-3-benzyloxyphenyl]-N'-[2-bromophenyl]urea

N-[3-benzyloxy-2-hydroxyphenyl]-N'-[2-bromophenyl]urea was prepared from 2-nitro-6-benzyloxyphenol (430 mg, 2.00 mmol) according to the procedure in General Method B. The product was purified by precipitation from methylene chloride/hexane(1/20) and filtering. (630 mg, 76%). $^1$H NMR (CD$_3$OD): δ 7.93 (d, 1H), 7.58 (d, 1H), 7.54–7.42 (m, 3H), 7.40–7.25 (m, 4H), 7.00 (t, 1H), 6.69 (d, 2H), 5.16 (s, 2H).

EXAMPLE 98

Preparation of N-3-[2-hydroxy-5-indanone]-N'-[2-bromophenyl]urea a) Preparation of 2-hydroxy-3-nitro-5-indanone 2-Hydroxy-5-indanone(3.00 g, 20.0 mmol) was dissolved in methylene chloride(40 mL) followed by the addition of sodium nitrate (1.95 g, 21.0 mmol). The addition of sulfuric acid (25 mL/3M) was then made, followed by addition of a catalytic amount of sodium nitrite. The mixture was allowed to stir. After 24 hours, the reaction mixture was diluted with methylene chloride and extracted with water. The organic layer was dried over $MgSO_4$ and filtered. The solvent was evaporated and chromatography of the resulting solid on silica gel (4% $MeOH/CH_2Cl_2$) gave the desired product(1.5 g, 39%). $^1$H NMR ($CD_3COCD_3$): δ 7.70 (d,1H), 7.04 (d, 1H), 3.04 (d, 2H), 2.74 (d, 2H).

b) Preparation of 3-amino-2-hydroxy-5-indanone

A mixture of 2-hydroxy-3-nitro-5-indanone (1.50 g, 7.80 mmol) and tin (II) chloride (5.25 g, 23.3 mmol) in ethanol (150 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product(1.00 g, 79%). $^1$H NMR ($CD_3OD$): δ 6.85 (d,1H), 6.45 (d, 1H), 2.95 (d, 2H), 2.60 (d, 2H).

c) Preparation N-3-[2-hydroxy-5-indanone]-N'-[2-bromophenyl]urea

N-[2-Hydroxy-5-indanone]-N'-[2-bromophenyl]urea was prepared from 3-amino-2-hydroxy-5-indanone (326 mg, 2.00 mmol) according to the procedure in General Method B. The product was purified by precipitation from methylene chloride/hexane(1/20) and filtering. (610 mg, 85%). $^1$H NMR ($CD_3OD$): δ 7.92 (d, 1H), 7.65 (m, 2H), 7.45 (t, 1H), 7.09 (t, 1H), 7.00 (d, 1H), 2.90 (d, 2H), 2.66 (d, 2H).

EXAMPLE 99

Preparation of (E)-N-[4-[2-(Methoxycarbonyl)ethenyl]-2-hydroxyphenyl]-N'-2-bromophenyl]urea a) Preparation of 4-nitro-3-hydroxycinnamic acid 3-Hydroxycinnamic acid (3.00 g, 18.3 mmol) was dissolved in methylene chloride(40 mL) followed by the addition of sodium nitrate (1.70 g, 26.1 mmol). The addition of sulfuric acid (25 mL/3M) was then made, followed by addition of a catalytic amount of sodium nitrite. The mixture was allowed to stir. After 24 hours, the reaction mixture was diluted with methylene chloride and extracted with water. The organic layer was dried over $MgSO_4$ and filtered. The solvent was evaporated and chromatography of the resulting solid on silica gel (4% $MeOH/CH_2Cl_2$) gave the desired product(1.0 g, 26%). $^1$H NMR ($CD_3COCD_3$): δ 8.07 (d, 1H), 7.69 (d, 1H), 7.51 (s, 1H), 7.46 (d, 2H), 6.75 (d,1H).

b) Preparation of 4-nitro-3-hydroxymethylcinnamate

4-Nitro-3-hydroxycinnamic acid was stirred in excess methanol with a catalytic amount of sulfuric acid. The solvent was evaporated and chromatography of the resulting solid on silica gel (4% $MeOH/CH_2Cl_2$) gave the desired product(1.0 g, 94%). $^1$H NMR ($CD_3COCD_3$): δ 8.17 (d, 1H), 7.69 (d, 1H), 7.52 (s, 1H), 7.45 (d, 2H), 6.75 (d,1H), 3.80 (s, 3H).

c) Preparation of 4-amino-3-hydroxymethylcinnamate

A mixture of 4-nitro-3-hydroxymethylcinnamate (1.0 g, 4.50 mmol) and tin (II) chloride (3.0 g, 13.4 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product (650 mg, 75%). $^1$H NMR ($CD_3OD$): δ 7.50 (d,1H), 6.94 (s, 1H), 6.89 (d, 1H), 6.68 (d, 1H), 6.18 (d, 1H), 3.74 (s, 3H).

d) Preparation (E)-N-[4-[2-(Methoxycarbonyl)ethenyl]-2-hydroxyphenyl]-N'-[2-bromophenyl]urea (E)-N-[4-[2-(Methoxycarbonyl)ethenyl]-2-hydroxyphenyl]-N'-[2-bromophenyl]urea was prepared from 4-amino-3-hydroxymethylcinnamate (250 mg, 1.3 mmol) according to the procedure in General Method B. The product was purified by precipitation from methylene chloride/hexane(1/20) and filtering. (300 mg, 59%). $^1$H NMR ($CD_3OD$): δ 8.24 (d,1H), 8.05 (d, 1H), 7.69 (d, 1H), 7.65 (d, 1H), 7.42 (t, 1H), 7.21 (s, 1H), 7.19 (d, 1H), 7.10 (t, 1H) 6,45 (d,1H) 3.81 (s, 3H).

EXAMPLE 100

Preparation of (E)-N-[3-[2-(Methoxycarbonyl)ethenyl]-2-hydroxyphenyl]-N'-[2-bromophenyl]urea N'-[2-bromophenyl]urea a) Preparation of 3-nitro-2-hydroxycinnamic acid 2-Hydroxycinnamic acid (3.00 g, 18.3 mmol) was dissolved in methylene chloride(40 mL) followed by the addition of sodium nitrate (2.21 g, 26.1 mmol). The addition of sulfuric acid (30 mL/3M) was then made, followed by addition of a catalytic amount of sodium nitrite. The mixture was allowed to stir. After 24 hours, the reaction mixture was diluted with methylene chloride and extracted with water. The organic layer was dried over $MgSO_4$ and filtered. The solvent was evaporated and chromatography of the resulting solid on silica gel (4% $MeOH/CH_2Cl_2$) gave the desired product(2.0 g, 52%). $^1$H NMR ($CD_3COCD_3$): δ 8.21 (d, 1H), 8.16 (d, 1H), 8.05 (d, 1H), 7.19 (t, 1H), 6.72 (d, 1H).

b) Preparation of 3-nitro-2-hydroxymethylcinnamate 3-nitro-2-hydroxycinnarmic acid was stirred in excess methanol with a catalytic amount of sulfuric acid. The solvent was evaporated and chromatography of the resulting solid on silica gel (4% $MeOH/CH_2Cl_2$) gave the desired product(1.0 g, 94%). $^1$H NMR ($CD_3COCD_3$): δ 8.25 (d, 1H), 7.8.15 (d, 1H), 8.06 (s, 1H), 7.20 (t, 2H), 6.76 (d,1H), 3.80 (s, 3H).

c) Preparation of 3-amino-2-hydroxymethylcinnamate

A mixture of 3-nitro-2-hydroxymethylcinnamate (1.0 g, 4.5 mmol) and tin (II) chloride (3.0 g, 13.4 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product (700 mg, 81%). $^1$H NMR ($CD_3OD$): δ 8.04 (d, 1H), 6.93 (d, 1H), 6.79 (d, 1H), 6.71 (t, 1H), 6.43 (d, 1H), 3.72 (s, 3H).

d) Preparation(E)-N-[3-[2-(Methoxycarbonyl)ethenyl]-2-hydroxyphenyl]-N'-[2-bromophenyl]urea (E)-N-[3-[2-(Methoxycarbonyl)ethenyl]-2-hydroxyphenyl]-N'-[2-bromophenyl]urea was prepared from 3-amino-2-hydroxymethylcinnamate (100 mg, 0.52 mmol) according to the procedure in General Method B. The product was purified by precipitation from methylene chloride/hexane(1/20) and filtering. (150 mg, 74%). $^1$H NMR (CD$_3$OD): δ 8.10 (d,1H), 8.00 (d, 1H), 7.69 (d, 1H), 7.65 (d, 1H), 7.42 (t, 1H), 7.38 (t, 1H), 7.32 (d, 1H), 7.05 (t, 1H) 6.55 (d,1H) 3.81 (s, 3H).

EXAMPLE 101

Preparation of (E)-N-[3-[2-(Aminocarbonyl) ethenyl]-2-hydroxyphenyl]-N'-[2-bromophenyl]urea N'-[2-bromophenyl]urea a) Preparation of 2-hydroxycinnamide 2-Hydroxycinnamic acid (2.00 g, 12.3 mmol) was dissolved in dimethyl formamide(10 mL) followed by the addition of benzotriazol-1-yloxy-tris(dimethylamino) phosphonium hexafluorophosphate (5.4 g, 12.3 mmol) and triethylamine (1.7 mL, 12.3 mmol). Ammonia gas was bubbled into the reaction mixture for 30 minutes. The mixture was allowed to stir for 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.5 g, 75%).

b) Preparation of 3-nitro-2-hydroxycinnamide

2-Hydroxycinnamide (750 mg, 4.6 mmol) was dissolved in methylene chloride(40 mL) followed by the addition of sodium nitrate (430 mg, 5.1 mmol). The addition of sulfuric acid (7 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(350 mg, 36%). $^1$H NMR (CD3COCD$_3$): δ 8.19 (d, 1H), 8.02 (d, 1H), 7.88 (d, 1H), 7.15 (t, 1H), 6.84 (d, 1H).

c) Preparation of 3-amino-2-hydroxycinnamide

A mixture of 3-nitro-2-hydroxymethylcinnamate (350 mg, 1.7 mmol) and tin (II) chloride (3.0 g, 13.4 mmol) in ethanol(50 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(244 mg,80%).

d) Preparation of (E)-N-[3-[2-(Aminocarbonyl)ethenyl]-2-hydroxyphenyl]-N'-[2-bromophenyl]urea (E)-N-[3-[2-(Aminocarbonyl)ethenyl]-2-hydroxyphenyl]-N'-[2-bromophenyl]urea was prepared from 3-amino-2-hydroxycinnamide (100 mg, 0.56 mmol) according to the procedure in General Method B. The product was purified by precipitation from methylene chloride/hexane(1/20) and filtering. (110 mg, 52%). $^1$H NMR (CD$_3$OD): δ 8.00 (d,1H), 7.90 (d, 1H), 7.63 (d, 1H), 7.55 (d, 1H), 7.35 (m, 2H), 7.05 (t, 1H), 6.95 (t, 1H), 6.70 (d,1H).

EXAMPLE 102

Preparation of (E)-N-[4-[2-(Aminocarbonyl) ethenyl]-2-hydroxyphenyl]-N'-[2-bromophenyl]urea N'-[2-bromophenyl]urea a) Preparation of 3-hydroxycinnamide 3-Hydroxycinnamic acid (2.00 g, 12.3 mmol) was dissolved in dimethyl formamide(10 mL) followed by the addition of benzotriazol-1-yloxy-tris(dimethylamino) phosphonium hexafluorophosphate (5.4 g, 12.3 mmol) and triethylamine (1.7 mL, 12.3 mmol). Ammonia gas was bubbled into the reaction mixture for 30 minutes. The mixture was allowed to stir for 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(1.3 g, 65%).

b) Preparation of 4-nitro-3-hydroxycinnamide

3-Hydroxycinnamide (750 mg, 4.6 mmol) was dissolved in methylene chloride(40 mL) followed by the addition of sodium nitrate (430 mg, 5.1 mmol). The addition of sulfuric acid (7 mL/3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(240 mg, 25%). $^1$H NMR (CD$_3$COCD$_3$): δ 8.09 (d, 1H), 7.49 (d, 1H), 7.26 (s, 1H), 7.16 (d, 1H), 6.71 (d, 1H).

c) Preparation of 4-amino-2-hydroxycinnamide

A mixture of 4-nitro-3-hydroxymethylcinnamate (300 mg, 1.40 mmol) and tin (II) chloride (980 mg, 4.30 mmol) in ethanol(50 mL) was heated at 80° C. under argon. After 2 hours, the starting material had disappeared and the solution was allowed to cool down and then poured into ice. The pH was made slightly basic (pH 7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product (200 mg, 74%).

d) Preparation(E)-N-[3-[2-(Aminocarbonyl)ethenyl]-2-hydroxyphenyl]-N'-[2-bromophenyl]urea (E)-N-[3-[2-(Aminocarbonyl)ethenyl]-2-hydroxyphenyl]-N'-[2-bromophenyl]urea was prepared from 4-amino-2-hydroxycinnamide (100 mg, 0.56 mmol) according to the procedure in General Method B. The product was purified by precipitation from methylene chloride/hexane(1/20) and filtering. (125 mg, 54%). $^1$H NMR (CD$_3$OD): δ 8.05 (d,1H), 7.92 (d, 1H), 7.60 (d, 1H), 7.45 (d, 1H), 7.35 (t, 1H), 7.05 (m, 2H), 6.50 (d,1H).

EXAMPLE 103

Preparation of N-[2-hydroxy 4-(phenylaminocarboxy)phenyl]-N'-[2-bromophenyl] urea N-[2-hydroxy 4-(phenylaminocarboxy)phenyl]-N'-[2-bromophenyl]urea was prepared from 5-(phenylaminocarboxy) 2-aminophenol (0.50 mmol) according to the procedure in General Method B. The product was purified by precipitation from methylene chloride/hexane(1/20) and filtering. (150 mg, 70%). $^1$H NMR (CD$_3$OD): δ 8.25 (d, 1H), 8.00 (d, 1H), 7.75 (d, 2H), 7.64 (d, 1H), 7.50 (d, 2H), 7.41 (m, 3H), 7.16 (t, 1H), 7.05 (t, 1H).

EXAMPLE 104

Preparation of N-[4-aminocarbonyl-2-hydroxyphenyl]-N'-[2-bromophenyl]urea

N-[4-Aminocarbonyl-2-hydroxyphenyl]-N'-[2-bromophenyl]urea was prepared from 5-aminocarbonyl-2-aminophenol (304 mg, 0.50 mmol) according to the procedure in General Method B. The product was purified by precipitation from methylene chloride/hexane(1/20) and filtering. (440 mg, 62%). $^1$H NMR (CD$_3$OD): δ 8.09 (d, 1H), 7.91 (d, 1H), 7.60 (d, 1H), 7.45 (m, 3H), 7.00 (d, 1H).

EXAMPLE 105

Preparation of N-(2-Hydroxy-3,5,6-trifluorophenyl)-N'-(2-bromophenyl)urea

N-(2-Hydroxy-3,5,6-trifluorophenyl)-N'-(2-bromophenyl)urea was prepared from 3,5,6-trifluoro-2-hydroxyaniline (83 mg, 0.51 mmol) and 2-(bromophenyl)isocyanate (100 mg, 0.53 mmol) according to the procedure in General Method B. The product was purified by preparation thin layer chromatography. EI-MS m/z 359 (M–H)$^-$.

EXAMPLE 106

Preparation of N-(2-Hydroxy-3-fluoro-4-trifluoromethylphenyl)-N'-(2-bromophenyl)urea N-(2-Hydroxy-3-fluoro-4-trifluoromethylphenyl)-N'-(2-bromophenyl)urea was prepared from 4-trifluoromethyl-3-fluoro-2-hydroxyaniline (239 mg, 1.2 mmol) and 2-(bromophenyl)isocyanate (243 mg, 1.2 mmol) according to the procedure in General Method B. Removal of solvent under reduced pressure and chromatography of the resulting solid on silica gel (hexane:ethyl acetate) gave the title compound (20 mg, 4%). EI-MS m/z 391 (M–H)$^-$.

EXAMPLE 107

Preparation of N-(2-Hydroxy-3-iodophenyl)-N'-(2-bromophenyl)urea

N-(2-Hydroxy-3-iodophenyl)-N'-(2-bromophenyl)urea was prepared from 3-iodo-2-hydroxyaniline (200 mg, 0.85 mmol) and 2-(bromophenyl)isocyanate (169 mg, 0.85 mmol) according to the procedure in General Method B. Removal of solvent under reduced pressure and chromatography of the resulting solid on silica gel (hexane:ether) gave the title compound (40 mg, 11%). $^1$H NMR (DMSO): δ 9.45 (s, 1H), 9.15 (s, 1H), 8.8 (s, 1H), 7.95 (d, 1H), 7.8 (d, 1H), 7.65 (d, 1H), 7.4 (d, 1H), 7.3 (t, 1H), 7.0 (t, 1H), 6.65(t, 1H).

EXAMPLE 108

Preparation of N-[2-[[[2-(trifluoromethyl)phenyl]sulfonyl]amino]phenyl]-N'-(2-bromophenyl)urea a) Preparation of [2-[2-(trifluoromethyl)phenyl](sulfonamido)aniline]

The title compound was prepared according to General Method C using 2-(trifluoromethyl)benzenesulfonyl chloride (1 equiv.). The product was purified by chromatography on silica gel (methylene chloride:methanol) (1.04 g, 33%). EI-MS m/z 317 (M+H)$^+$.

b) Preparation of N-[2-[[[2-(trifluoromethyl)phenyl]sulfonyl]amino]phenyl]-N'-(2-bromophenyl)urea The title compound was prepared using [2-[2(trifluoromethyl)phenyl](sulfonamido)aniline (1.04 g, 3.2 mmol) and 2-(bromophenyl)isocyanate (652 mg, 3.2 mmol) according to General Method B. The solvent was evaporated to give the desired urea (1.03 g, 61%). EI-MS m/z 514 (M+H)$^+$.

EXAMPLE 109

Preparation of N-(2-Bromophenyl)-N'-[2-dimethylaminosulfonylamino]phenyl]urea a) Preparation of [2-[1,1-(dimethylamino)]sulfonamidoaniline]

The title compound was prepared according to General Method C using dimethylsulfamoyl chloride (1 equiv.). The product was purified by chromatography on silica gel (methylene chloride:methanol). ES-MS m/z 216 (M+H)$^+$.

b) Preparation of N-(2-Bromophenyl)-N'-[2-(dimethylaminosulfonylamino]phenyl]urea The title compound was prepared from [2-[1,1-(dimethlyamino)sulfonamidoaniline (137 mg, 0.6 mmol) and 2-(bromophenyl)isocyanate (126 mg, 0.6 mmol) according to General Method B. The solvent was evaporated and chromatography on silica gel (ethyl acetate:hexane) gave the desired urea. EI-MS m/z 413 (M+H)$^+$.

EXAMPLE 110

Preparation of N-[2-(Phenethylsulfonylamino)phenyl]-N'-(2-bromophenyl)urea

[2-(Phenethylsulfonamido)aniline] (example 60, 300 mg, 1.09 mmol) was placed in a Parr shaker bottle containing palladium (180 mg) under an argon stream. Methanol (150 mL) was added and the container placed on a Parr shaker (55 psi) for several hours. The reaction mixture was filtered through Celite and the filtrate was evaporated to give the desired aniline (269 mg, 90%). EI-MS m/z 277 (M+H)$^+$.

b) Preparation of N-[2-(Phenethylsulfonylamino)phenyl]-N'-(2-bromophenyl)urea

The title compound was prepared from [2-(phenethylsulfonamido)aniline] (269 mg, 0.97 mmol) and 2-(bromophenyl)isocyanate (193 mg, 0.97 mmol) according to General Method B. The desired urea was precipitated out of toluenethexane (384 mg, 78%). EI-MS m/z 472 (M–H)$^-$.

EXAMPLE 111

Preparation of N-[2-[(2-acetamido-4-methylthiazol-5-yl)sulfonylamino]phenyl]-N'-(2-bromophenyl)urea a) Preparation of [2-[(2-acetamido-4-methyl-5-thiazole)sulfonamido]aniline]

The title compound was prepared using 2-acetamido-4-methyl-5-thiazolesulfonyl chloride (1 equiv.) according to General Method C. A solid precipatated from the reaction mixture and was filtered to give the desired aniline (1.68 g, 52%). ES-MS m/z 327 (M+H)$^+$.

b) Preparation of N-[2-[(2-acetamido-4methylthiazol-5-yl)sulfonylamino]phenyl]-N'-(2-bromophenyl)urea The title compound was prepared from [2-[(2-acetamido-4-methyl-5-thiazole)sulfonamido]aniline] (1.68 g,5.14 mmol) and 2-(bromophenyl)isocyanate (1.02 g, 5.14 mmol) according to General Method B. The product was precipitated from ethyl acetate/hexane (220 mg, 8%). EI-MS m/z 524 (M+H)$^+$.

EXAMPLE 112

Preparation of N-[2-hydroxy-4-cyanophenyl]-N'-4-phenylphenyl]urea

N-[2-Hydroxy-4-cyanophenyl]-N'-[4phenylphenyl]urea was prepared from 2-amino-5-cyanophenol (60 mg, 0.45 mmol) according to the procedure in General Method B. The product was purified by precipitation from methylene chloride/hexane(1/20) and filtering. (135 mg, 75%). $^1$H NMR (CD$_3$OD): δ 8.33 (d, 1H), 7.71–7.29 (m, 9H), 7.25 (d, 1H), 7.12 (s, 1H).

EXAMPLE 113

Preparation of N-[2-hydroxy-4-cyanophenyl]-N'-[2,3-dichlorophenyl]urea

N-[2-Hydroxy-4-cyanophenyl]-N'-[2,3 dichlorophenyl] urea was prepared from 2-amino-5-cyanophenol (60 mg, 0.45 mmol) according to the procedure in General Method B. The product was purified by precipitation from methylene chloride/hexane(1/20) and filtering. (125 mg, 86%). $^1$H NMR (CD$_3$OD): δ 8.27 (d, 1H), 8.15 (m, 1H), 7.39–7.20 (m, 2H), 7.16 (d, 1H), 7.06 (s, 1H).

EXAMPLE 114

Preparation of N-[2-hydroxy-4-cyanophenyl]-N'-[2-methoxyphenyl]urea

N-[2-Hydroxy-4-cyanophenyl]-N'-[2-methoxyphenyl] urea was prepared from 2-amino-5-cyanophenol (60 mg, 0.45 mmol) according to the procedure in General Method B. The product was purified by precipitation from methylene chloride/hexane(1/20) and filtering (105 mg, 83%). $^1$H NMR (CD$_3$OD): δ 8.26 (d, 1H), 8.02 (d, 1H), 7.14 (d, 1H), 7.05 (s, 1H), 7.00–6.83 (m, 3H), 3,84 (s, 3H).

EXAMPLE 115

Preparation of N-[2-hydroxy-4-cyanophenyl]-N'-[3-methoxyphenyl]urea

N-[2-Hydroxy-4-cyanophenyl]-N'-[3-methoxyphenyl] urea was prepared from 2-amino-5-cyanophenol (60 mg, 0.45 mmol) according to the procedure in General Method B. The product was purified by precipitation from methylene chloride/hexane(1/20) and filtering. (102 mg, 80%). $^1$H NMR (CD$_3$OD): δ 8.25 (d, 1H), 7.25–7.08 (m, 3H), 7.04 (s, 1H), 6.90 (t, 1H), 6.58 (d, 1H).

EXAMPLE 116

Preparation of N-[2-hydroxy-5-fluorophenyl]-N'-[2-bromophenyl]urea a) Preparation of 2-amino-4-fluorophenol A mixture of 4-fluoro-2-nitrophenol(1 g, 4.64 mmol) and tin (II) chloride (5.4 g, 24.2 mmol) in ethanol(50 mL) was heated at 80° C. under argon. After 2 hours, the starting material had disappeared and the solution was allowed to cool down and then poured into ice. The pH is made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(622 mg, 85%). $^1$H NMR (CD$_3$OD): δ 6.51 (dd, 1H), 6.32 (dd, 1H), 6.17 (ddd, 1H).

b) Preparation of N-[2-hydroxy-5-fluorophenyl]-N'-[2-bromophenyl]urea

N-[2-Hydroxy-5-fluorophenyl]-N'-[2-bromophenyl]urea was prepared from 2-amino-6-fluorophenol (254 mg, 2.00 mmol) according to the procedure in General Method B. The product was purified by precipitation from methylene chloride/hexane(1/20) and filtering. (520 mg,80%). $^1$H NMR (CD$_3$OD): δ 7.88 (d, 1H), 7.79 (dd, 1H), 7.57 (d, 1H), 7.31 (t, 1H), 7.00 (t, 1H), 6.76 (dd, 1H), 6.57 (ddd,1H).

EXAMPLE 117

Preparation of N-[2-hydroxy-5-trfluoromethylphenyl]-N'-[2-bromophenyl]urea a) Preparation of 2-amino-4-trifluoromethylphenol A mixture of 4-trifluoromethyl-2-nitrophenol(1.0 g, 4.8 mmol) and tin (II) chloride (5.4 g, 24.2 mmol) in ethanol (150 mL) was heated at 80° C. under argon. After 2 hours, the starting material had disappeared and the solution was allowed to cool down and then poured into ice. The pH was made slightly basic (pH7–8), by addition of solid NaOH, before being extracted with ethyl acetate. The organic phase was washed with brine, dried over MgSO$_4$ and filtered. The solvent was evaporated and chromatography of the resulting solid on silica gel (4% MeOH/CH$_2$Cl$_2$) gave the desired product(708 mg, 83%). $^1$H NMR (CD$_3$OD): δ 6.87 (s, 1H), 6.80 (d, 1H), 6.69 (d, 1H).

b) Preparation of N-[2-hydroxy-5-trifluoromethylphenyl]-N'-[2-bromophenyl]urea

N-[2-hydroxy-5-trifluoromethylphenyl]-N'-[2-bromophenyl]urea was prepared from 2-amino-4-trifluoromethylphenol (354 mg, 2.00 mmol) according to the procedure in General Method B. The product was purified by precipitation from methylene chloride/hexane (1 equiv./20 equiv.) and filtering. (490 mg, 65%). $^1$H NMR (CD$_3$OD): δ 8.40 (s, 1H), 7.94 (d, 1H), 7.60 (d, 1H), 7.35 (t, 1H), 7.18 (d, 1H), 7.03 (t, 1H), 6.95 (d, 1H).

EXAMPLE 118

Preparation of N-[2-hydroxyphenyl]-N'-[2-bromophenyl]urea

N-[2-hydroxyphenyl]-N'-[2-bromophenyl]urea was prepared from 2-amino-phenol (141 mg, 1.30 mmol) according to the procedure in General Method B. The product was purified by precipitation from methylene chloride/hexane(1/20) and filtering. (300 mg,75%). $^1$H NMR (CD$_3$OD): δ 8.05 (d, 1H), 7.49 (d, 1H), 7.25 (t, 2H), 6.96 (t, 1H), 6.90 (t, 2H), 6.68 (t, 1H).

EXAMPLE 119

Preparation of N-[trans-3-styrl 2-hydroxyphenyl]-N'-[2-bromophenyl]urea a) Preparation of trans-6-styrl-2-nitrophenol Trans-2-styrlphenol (500 mg, 2.55 mmol) was dissolved in methylene chloride(40 mL) followed by the addition of sodium nitrate (240 mg, 2.81 mmol). The addition of sulfuric acid (3 mL of 3M) was then made, followed by addition of a catalytic amount of sodium nitrite. The mixture was allowed to stir. After 24 hours, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product (200 mg, 36%). $^1$H NMR (CD3COCD$_3$): δ 8.05 (d, 1H), 7.90 (d, 2H),7.65–7.20 (m,7H),7.00 (t,1H).

b) Preparation of trans-6-styrl-2-aminophenol

A mixture of trans-6-styrl-2-nitrophenol (200 mg, 0.83 mmol) and tin (II) chloride (560 mg, 2.60 mmol) in ethanol (50 mL) was heated at 80° C. under argon. After 2 hours, the starting material has disappeared and the solution was allowed to cool down and then poured into ice. The pH is made slightly basic (pH7–8), by addition of solid NaOH, before being extracted with ethyl acetate. The organic phase was washed with brine, dried over $MgSO_4$ and filtered. The solvent was evaporated and chromatography of the resulting solid on silica gel (4% $MeOH/CH_2Cl_2$) gave the desired product (50 mg, 29%). $^1H$ NMR ($CD_3OD$): δ 7.51 (m, 3H), 7.29 (m, 3H), 7.11 (t, 1H), 7.00 (m, 2H), 6.69 (m, 2H).

c) Preparation of N-[trans-3-styrl-2-hydroxyphenyl]-N'-[2-bromophenyl]urea

N-[trans-3-styrl-2-hydroxyphenyl]-N'-[2-bromophenyl]urea was prepared from trans-6-styrl-2-aminophenol (35 mg, 0.17 mmol) according to the procedure in General Method B. The product was purified by precipitation from methylene chloride/hexane(1/20) and filtering. (36 mg, 53%). $^1H$ NMR ($CD_3OD$): δ 7.97 (d, 1H), 7.62–7.48 (m, 4H), 7.45–7.26 (m, 5H), 7.25 (t, 1H), 7.15 (d, 1H), 7.01 (t, 1H), 6.88 (t 2H).

EXAMPLE 120

Preparation of N-[2-hydroxy-3,4-dichlorophenyl]-N'-[2-methoxyphenyl]urea

N-[2-hydroxy-3,4-dichlorophenyl]-N'-[2-methoxyphenyl]urea was prepared from 2-amino-5,6-dichlorophenol (80 mg, 0.50 mmol, example 82b) according to the procedure in General Method B. The product was purified by precipitation from methylene chloride/hexane(1/20) and filtering. (125 mg,77%). $^1H$ NMR ($CD_3OD$): δ 8.02 (d, 1H), 7.79 (d, 1H), 7.05–6.86 (m, 4H), 3.92 (s, 3H).

EXAMPLE 121

Preparation of N-[2-hydroxy-3,4-dichlorophenyl]-N'-[4-methoxyphenyl]urea

N-[2-hydroxy-3,4-dichlorophenyl]-N'-[4-methoxyphenyl]urea was prepared from 2-amino-5,6-dichlorophenol (80 mg, 0.50 mmol, example 82b) according to the procedure in General Method B. The product was purified by precipitation from methylene chloride/hexane (1 equiv./20 equiv.) and filtering. (120 mg, 74%). $^1H$ NMR ($CD_3OD$): δ 7.89 (d, 1H), 7.35 (d, 2H), 6.99 (d, 1H), 6.90 (dd, 2H), 3.80 (s, 3H).

EXAMPLE 122

Preparation of N-[2-hydroxy-3,4-dichlorophenyl]-N'-[3-trifluoromethylphenyl]urea N-[2-hydroxy-3,4-dichlorophenyl]-N'-[3-trifluoromethylphenyl]urea was prepared from 2-amino-5,6-dichlorophenol (80 mg, 0.50 mmol, example 82b) according to the procedure in General Method B. The product was purified by precipitation from methylene chloride/hexane(1 equiv./20 equiv.) and filtering. (130 mg, 71%). $^1H$ NMR ($CD_3OD$): δ 7.96 (d, 2H), 7.60 (d, 1H), 7.48 (t, 1H), 7.30 (d, 1H), 7.00 (d, 1H).

EXAMPLE 123

Preparation of N-[2-hydroxy-3,4-dichlorophenyl]-N'-[2-phenylphenyl]urea

N-[2-hydroxy-3,4-dichlorophenyl]-N'-[2-phenylphenyl]urea was prepared from 2-amino-5,6-dichlorophenol (80 mg, 0.50 mmol, example 82b) according to the procedure in General Method B. The product was purified by precipitation from methylene chloride/hexane(1equiv./20 equiv.) and filtering. (110 mg, 59%). $^1H$ NMR ($CD_3OD$): δ 7.77 (d, 1H), 7.73 (d, 1H), 7.53–7.14 (m, 8H), 6.95 (d, 1H).

EXAMPLE 124

Preparation of N-[2-hydroxy-3,4-dichlorophenyl]-N'-[2,3-dichlorophenyl]urea

N-[2-Hydroxy-3,4-dichlorophenyl]-N'-[2,3-dichlorophenyl]urea was prepared from 2-amino-5,6-dichlorophenol (80 mg, 0.50 mmol, example 82b) according to the procedure in General Method B. The product was purified by precipitation from methylene chloride/hexane (1 equiv./20 equiv.) and filtering. (130 mg, 71%). $^1H$ NMR ($CD_3OD$): δ 8.06 (dd, 1H), 7.91 (d, 1H), 7.25 (m, 2H), 7.00 (d, 1H).

EXAMPLE 125

Preparation of N-[2-hydroxy-4-isopropylphenyl]-N'-[3-trifluoromethylphenyl]urea a) Preparation of 2-nitro-5-isopropylphenol 3-isopropylphenol (3.00 g, 22 mmol) was dissolved in methylene chloride(40 ml) followed by the addition of sodium nitrate (2.06 g, 24 mmol). The addition of sulfuric acid (25 mL/3M) is then made, followed by addition of a catalytic amount of sodium nitrite. The mixture was allowed to stir. After 24 h, the reaction mixture is diluted with methylene chloride and extracted with water. The organic layer is dried over $MgSO_4$ and filtered. The solvent was evaporated and chromatography of the resulting solid on silica gel (4% $MeOH/CH_2Cl_2$) gave the desired product (1.09 g, 27%). $^1H$ NMR ($CD_3COCD_3$): δ 7.95 (d,1H), 7.62 (d,1H), 7.11 (d, 1H), 2.95 (m, 1H), 1.24 (d, 6H).

b) Preparation of 2-amino-5-isopropylphenol

To a solution of 2-nitro-5-isopropylphenol(1 g, 6.4 mmol) in methanol(50 mL) was added 10% Pd/C (100 mg). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% $MeOH/CH_2Cl_2$) gave the desired product(775 mg, 93%). $^1H$ NMR ($CD_3OD$): δ 6.71–6.44 (m, 3H), 2.73 (m, 1H), 1.20 (d, 6H).

c) Preparation of N-[2-hydroxy-4-isopropylphenyl]-N'-[3-trifluoromethylphenyl]urea N-[2-hydroxy-4-isopropylphenyl]-N'-[3-trifluoromethylphenyl]urea was prepared from 2-amino-5-isopropylphenol (75 mg, 0.50 mmol) according to the procedure in General Method B. The product was purified by precipitation from methylene chloride/hexane (1 equiv./20 equiv.) and filtering. (140 mg, 83%). $^1H$ NMR ($CD_3OD$): δ 7.91 (d, 2H), 7.62 (d, 1H), 7.47 (t, 1H), 7.39 (d, 1H), 6.75 (s, 1H), 6.72 (d, 1H), 2.80 (m, 1H), 1.12 (d, 6H).

EXAMPLE 126

Preparation of N-[2-hydroxy-3-naphthyl]-N'-[2,3-dichlorophenyl]urea

N-[2-hydroxy-3-naphthyl]-N'-[2,3-dichlorophenyl]urea was prepared from 3-amino 2-naphthol (160 mg, 1.00 mmol) according to the procedure in General Method B. The product was purified by precipitation from methylene chloride/hexane(1 equiv./20 equiv.) and filtering. (285 mg, 82%). $^1H$ NMR ($CD_3OD$): δ 8.48 (s, 1H), 8.10 (d, 1H), 7.68 (d, 1H), 7.57 (d, 1H), 7.40–7.23 (m, 4H), 7.18 (d, 1H).

EXAMPLE 127

Preparation of N-[2-[(2,3-Dichlorothien-5-yl)]sulfonylamino]phenyl]-N'-(2-bromophenyl)urea a) Preparation of [2-[(2,3-Dichlorothien-5-yl)]sulfonylaminoaniline]

The tide compound was prepared according to General Method C using 2,3-dichlorothiophene-5-sulfonyl chloride ((1 eq). The product was purified by flash chromatography on silica gel (ethyl acetatelhexane 20/80-methylene chloride:methanol 90/10) (1.25 g, 39%). EI-MS m/z 321 (M–H)$^-$.

b) Preparation of N-[2-[(2,3-Dichlorothien-5-yl)]sulfonylamino]phenyl]-N'-(2-bromophenyl)urea The title compound was prepared from [2-[(2,3-dichlorothien-5-yl)]sulfonylaminoaniline (1.25 g,3.9 mmol) and 2-(bromophenyl)isocyanate (768 mg, 3.9 mmol) according to General Method B. The product was purified by flash chromatography on silica gel (ethyl acetate:hexane 30/70) (272 mg, 13%) EI-MS m/z 520 (M–H)$^-$.

EXAMPLE 128

Preparation of N-[2-[(3,5-Bistrifluoromethylphenyl)sulfonylamino]phenyl]-N'-(2-bromophenyl)urea a) Preparation of [2-(3,5-Bistrifluoromethylphenyl)sulfonylaminoaniline]

The tide compound was prepared according to General Method C using 3,5-(bistrifluoromethyl)phenylsulfonyl chloride (1.28 g, 4.1 mmol) and o-phenylenediamine (441 mg, 4.1 mmol). The product was purified by flash chromatography on silica gel (methylene chloride:methanol 95/5) (611 mg, 39%). EI-MS m/z 383 (M–H)$^-$.

b) Preparation of N-[2-[(3,5-Bistrifluoromethylphenyl)sulfonylamino]phenyl]-N'-(2-bromophenyl)urea The title compound was prepared from [2-(3,5-bistrifluoromethylphenyl) sulfonylaminoaniline (591 mg, 1.5 mmol) and 2-bromophenylisocyanate (305 mg, 1.5 mmol) according to General Method B. The product was purified by flash chromatography on silica gel (ethyl acetate-:hexane 30/70) (10 mg, 1%). EI-MS m/z 580 (M–H)$^-$.

EXAMPLE 129

Preparation of N-[2-[(2-Benzyl)sulfonylamino]-(5-trifluoromethyl)phenyl]-N'-(2-bromophenyl)urea a) Preparation of [(4-Benzylsulfonylamino)-(3-nitro)-benzotrifluoride]

4-Amino-3-nitro-benzotrifluoride (1.0 g, 4.85 mmol) was mixed in DMF and the reaction mixture was cooled to 0° C. Sodium hydride (175 mg, 7.28 mmol) was added to the cold mixture and allowed to mix for ten minutes (a deep red color was noted). Toluenesulfonyl chloride (925 mg, 4.85 mmol) was added (reaction color changed to yellow) and the reaction was mixed for sixteen hours at room temperature. The reaction was quenched in NH$_4$Cl and extracted with ethyl acetate:hexane (1:1). The product was purified by flash chromatography on silica gel (ethyl acetate:hexane 30/70) (878 mg, 52%) EI-MS m/z 359 (M–H)$^-$.

b) Preparation of [(4-Benzylsulfonylamino)-(3-amino)-benzotrifluoride]

[(4Benzylsulfonylamino)-(3-nitro)-benzotrifluoride (230 mg, 0.64 mmol) was mixed in methanol and poured into a Parr bottle. Palladium on carbon (15 mg) was added under an argon stream. The reaction mixture was placed on a Parr shaker (55 psi, H$_2$) for several hours. The reaction mixture was filtered through Celite to give the title compound. (210 mg, 99%) EI-MS m/z 329 (M–H)$^-$.

c) Preparation of N-[2-[(2-Benzyl)sulfonylamino]-(5-trifluoromethyl)phenyl]-N'-(2-bromophenyl)urea The title compound was prepared from [(4-benzylsulfonylamino)-(3-amino)-benzotrifluoride (210 mg, 0.64 mmol) and 2-bromophenylisocyanate (126 mg, 0.64 mmol) according to the procedure in General Method B. The product was purified by flash chromatography on silica gel (ethyl acetate:hexane 30/70) (70 mg, 21%) EI-MS m/z 526 (M–H)$^-$.

EXAMPLE 130

Preparation of N-[2-[2-(3-Nitrophenyl)sulfonylamino]phenyl]-N'-(2-bromophenyl)urea a) Preparation of [2-((3-Nitrophenyl)sulfonylamino)aniline]

The title compound was prepared according to General Method C using 3-nitrobenzenesulfonyl chloride (1 eq). The product was purified by flash chromatogrphy on silica gel (methylene chloride:methanol 96/4). (1.07 g, 37%) EI-MS m/z 294 (M+H)$^+$.

b) Preparation of N-[2-[(3-Nitrophenyl)sulfonylamino]phenyl]-N'-(2-bromophenyl)urea The title compound was prepared from [2-(3-nitrophenyl)sulfonylaminoaniline] (590 mg, 2.0 mmol) and 2-(bromophenyl)isocyanate (398 mg, 2.0 mmol) according to the procedure in General Method B. The product was purified by flash chromatography on silica gel (ethyl acetate-:hexane 30/70) (400 mg, 40%). EI-MS m/z 489 (M–H)$^-$.

EXAMPLE 131

Preparation of N-[2-[2-(4-Phenoxyphenyl)sulfonylamino]phenyl]-N'-(2-bromophenyl)urea a) Preparation of [2-((4-Phenoxyphenyl)sulfonylamino)aniline]

The title compound was prepared according to General Method C using 4-phenoxyphenylsulfonyl chloride (969 mg, 3.6 mmol) and o-phenylenediamine (300 mg, 2.77 mmol). The reaction mixture was partitioned between water (200 ml) and toluene:methylene chloride (1:3). The organic phase collected and the methylene chloride evaporated leaving the toluene. Hexane added and the product precipatated from solution. (317 mg, 34%) EI-MS m/z 341 (M+H)$^+$.

b) Preparation of N-[2-[(4-Phenoxyphenyl)sulfonylamino]phenyl]-N'-(2-bromophenyl)urea The title compound was prepared from [2-(4-phenoxyphenyl)sulfonyl aminoaniline (276 mg, 0.8 mmol) and 2-(bromophenyl)isocyanate (161 mg, 0.8 mmol) according to the procedured in General Method B. The product was purified by flash chromatography on silica gel (ethyl acetate-:hexane 30/70) (240 mg, 55%) EI-MS m/z 536 (M–H)$^-$.

EXAMPLE 132

Preparation of N-[[2-(1S)-10-Camphorsulfonylamino]phenyl]-N'-(2-bromophenyl)urea a) Preparation of 2-((1S)-10-Camphorsulfonylamino)aniline The title compound was prepared according to General Method C using (1S)(+)-10-Camphorsulfonyl chloride (1.16 g, 4.6 mmol) and o-phenylenediamine (500 mg, 4.6 mmol). The reaction mixtwue was partitioned between water (200 ml) and toluene:methylene chloride (1:3). The organic phase was separated and the methylene chloride evaporated leaving the toluene. Hexane was added and solid precipitated from solution. (130 mg, 9%) EI-MS m/z 323 (M+H)$^+$.

b) Preparation of N-[[2-(1S)-10-Camphorsulfonylamino]phenyl]-N'-(2-bromophenyl)urea The title compound was prepared from [2-(1S)-10-camphorsulfonylamino]aniline (130 mg, 0.4 mmol) and 2-(bromophenyl)isocyanate (80 mg, 0.4 mmol) according to the procedure in General Method B. The solvent was evaporated and product was precipitated from methylene chloride:hexane. (200 mg, 95%). EI-MS m/z 518 (M–H)⁻.

EXAMPLE 133

Preparation of N-[[2-(1R)-10-Camphorsulfonylamino]phenyl]-N'-(2-bromophenyl)urea a) Preparation of 2-((1R)-10-Camphorsulfonylamino)aniline The title compound was prepared according to General Method C using (1R)(–)-10-camphorsulfonyl chloride (1.16 g, 4.6 mmol) and o-phenylenediamine (500 mg, 4.6 mmol). The reaction mixture was partitioned between water (200 mL) and toluene:methylene chloride(1:3). The organic phase was separated and the methylene chloride evaporated leaving the toluene. Hexane was added and the product precipitated from solution. (563 mg, 38%). EI-MS m/z 323 (M+H)⁺.

b) Preparation of N-[[2-(1R)-10-Camphorsulfonylamino]phenyl]-N'-(2-bromophenyl)urea The title compound was prepared from [1-(1R)-10-camphorsulfonylaminoaniline] (563 mg, 1.75 mmol) and 2-(bromophenyl)isocyanate (346 mg, 1.75 mmol) according to the procedure in General Method B. The product was purified by flash chromatography on silica gel (ethyl acetate-:hexane 30/70) (263 mg, 29%) EI-MS m/z 518 (M–H)⁻.

EXAMPLE 134

Preparation of N-[2-[2-(2-Nitro-(4-trifluoromethyl)phenyl)sulfonylamino]phenyl-N'-(2-bromophenyl)urea a) Preparation of [2-[(2-Nitro)-(4-trifluoromethyl)phenyl]sulfonylamino]aniline The title compound was prepared according to General Method C using 2-nitro-4-(trifluoromethyl)benzenesulfonyl chloride (1 eq). The product was purified by flash chromatography on silica gel (methylene chloride:methanol 96/4) (875 mg, 25%) EI-MS m/z 362 (M+H)⁺.

b) Preparation of N-[2-[2-(2-Nitro-(4-trifluoromethyl)phenyl)sulfonylamino]phenyl-N'-(2-bromophenyl)urea The title compound was prepared from [2-[(2-nitro)-(4-trifluoromethyl) phenyl]sulfonylamino]aniline (740 mg, 2.1 mmol) and 2-(bromophenyl)isocyanate (406 mg, 2.1 mmol) according to General Method B. The product was purified by flash chromatography on silica gel (ethyl acetate:hexane 30/70). The product was further purified by recrystallization in ethyl acetate:hexane. (320 mg, 28%) EI-MS m/z 557 (M–H)⁻.

EXAMPLE 135

Preparation of N-(2-hydroxy-4-azidophenyl)-N'-(2-iodophenyl)urea a) Preparation of N-(2-hydroxy-4-aminophenyl)-N'-(2-iodophenyl)urea To a solution of N-(2-hydroxy-4-nitrophenyl)-N'-(2-iodophenyl)urea (220 mg, 0.55 mmol) in ethanol (15 mL), Tin chloride (522 mg, 2.75 mmol) was added. The reaction mixture was stirred at reflux for 16 hours then cooled to room temperature. The reaction mixture was basified to pH 8 with aq. NaHCO₃ then extracted with ethyl acetate (3×). The organic extracts were combined, dried over MgSO₄, filtered and concentrated under reduced pressure to give product (180 mg, 89%). EI-MS m/z 370 (M+H)⁺.

b) Preparation of N-(2-hydroxy-azidophenyl)-N'-(2-iodophenyl)urea

The N-(2-hydroxy-4-aminophenyl)-N'-(2-iodophenyl)urea(77 mg, 0.21 mmol) was added to HCl/H₂O (0.21 mL/0.42 mL), and cooled to 0° C. Sodium nitrate (14.5 mg, 0.21 mmol) was added to the reaction mixture. The reaction mixture was stirred at 0° C. for 30 minutes. Sodium azide (14 mg, 0.21 mmol) was added to reaction mixture and it was warmed to room temperature. The reaction mixture was stirred at room temperature for 18 hours. Then it was extracted with three times by ethyl acetate. The organic extracts were combined, dried over MgSO₄, filtered and concentrated under reduced pressure and chromatography of the resulting solid on silica gel (hexane : ethyl acetate; 5:1) gave product (20 mg, 24%). EI-MS m/z 396 (M+H)⁺.

EXAMPLE 136

Preparation of N-(2-hydroxy-3-azidophenyl)-N'-(2-bromophenyl)urea a) Preparation of N-(2-hydroxy-3-aminophenyl)-N'-(2-bromophenyl)urea To a solution of N-(2-hydroxy-3-nitrophenyl)-N'-(2-bromophenyl)urea (300 mg, 0.85 mmol) in ethanol (20 mL), Tin chloride (958 mg, 4.25 mmol) was added. The reaction mixture was stirred at reflux for 16 hours then cooled to room temperature. The reaction mixture was basified to pH 8 with aq. NaHCO₃ then extracted with ethyl acetate (3×). The organic extracts were combined, dried over MgSO₄, filtered and concentrated under reduced pressure to give product (274 mg, 99%). EI-MS m/z 323 (M+H)⁺.

b) Preparation of N(2-hydroxy-3-azidophenyl)-N'-(2-bromophenyl)urea

The N-(2-hydroxy-3-aminophenyl)-N'-(2-bromophenyl)urea(274 mg, 0.85 mmol) was added to HCl/H₂O (0.85 mL/1.7 mL), cooled to 0° C. Sodium nitrate (58.6 mg, 0.85 mmol) was added to the reaction mixture. The reaction mixture was stirred at 0° C. for 30 minutes. Sodium azide (55 mg, 0.85 mmol) was added to reaction mixture and it was warmed to room temperature. The reaction mixture was stirred at room temperature for 18 hours then it was extracted with three times with ethyl acetate. The organic extracts were combined, dried over MgSO₄, filtered and concentrated under reduced pressure and chromatography of the resulting solid on silica gel (hexane:ethyl acetate; 5:1) gave product (210 mg, 71%). EI-MS m/z 349 (M+H)⁺.

EXAMPLE 137

Preparation of N-[2-hydroxy-3-cyanophenyl]-N'-[2-methoxyphenyl]urea

N-[2-hydroxy-3-cyanophenyl]-N'-[2-methoxyphenyl]urea was prepared from 2-amino-6-cyanophenol (134 mg, 1.00 mmol) according to the procedure in General Method B. The product was purified by precipitation from methylene chloride/hexane(1 equiv./20 equiv.) and filtering. (230 mg, 81%). ¹H NMR (CD₃OD): δ 8.06 (d, 1H), 7.79 (d, 1H), 7.49–7.35 (m, 2H), 7.05–6,87 (m, 3H), 3.95 (s, 3H).

EXAMPLE 138

Preparation of N-[2-hydroxy-3-cyanophenyl]-N'-[3-trifluoromethylphenyl]urea

N-[2-hydroxy-3-cyanophenyl]-N'-[3-trifluoromethylphenyl]urea was prepared from 2-amino-6- cyanophenol (134 mg, 1.00 mmol, example 83a) according to the procedure in General Method B. The product was purified by precipitation from methylene chloride/hexane (1 equiv./20 equiv.) and filtering. (280 mg, 87%). $^1$H NMR (CD$_3$OD): δ 8.10 (d, 1H), 7.96 (s, 1H), 7.54 (d, 1H), 7.55–7.25 (m, 3H), 7.01 (t, 1H).

EXAMPLE 139

Preparation of N-[2-hydroxy-3-cyanophenyl]-N'-[2-phenylphenyl]urea

N-[2-hydroxy-3-cyanophenyl]-N'-[2-phenylphenyl]urea was prepared from 2-amino-6-cyanophenol (134 mg, 1.00 mmol, example 83a) according to the procedure in General Method B. The product was purified by precipitation from methylene chloride/hexane (1 equiv./20 equiv.) and filtering. (270 mg, 82%). $^1$H NMR (CD$_3$OD): δ 7.81 (d, 1H), 7.75 (d, 1H), 7.56–7.15 (m, 9H), 6.91 (t, 1H).

EXAMPLE 140

Preparation of N-[2-hydroxy-3-cyanophenyl]-N'-[2.3-dichlorophenyl]urea

N-[2-hydroxy-3-cyanophenyl]-N'-[2,3 dichlorophenyl] urea was prepared from 2-amino-6-cyanophenol (134 mg, 1.00 mmol, example 83a) according to the procedure in General Method B. The product was purified by precipitation from methylene chloride/hexane (1 equiv./20 equiv.) and filtering. (300 mg, 93%). 1H NMR (CD$_3$OD): δ 8.11 (d, 1H), 8.01 (d, 1H), 7.33–7.25 (m, 3H), 7.00 (t, 1H).

EXAMPLE 141

Preparation of N-[2-hydroxy-4-isopropylphenyl]-N'-[2,3-dichlorophenyl]urea

N-[2-hydroxy-4-isopropylphenyl]-N'-[2,3-dichlorophenyl]urea was prepared from 2-amino-5-isopropylphenol (150 mg, 1.00 mmol, example 128a) according to the procedure in General Method B. The product was purified by precipitation from methylene chloride/hexane (1 equiv./20 equiv.) and filtering (285 mg, 84%). $^1$H NMR (CD$_3$OD): δ 8.05 (d, 2H), 7.77 (s, 1H), 7.26 (m, 2H), 6.88 (m, 2H), 2.82 (m, 1H), 1.25 (d, 6H).

EXAMPLE 142

Preparation of N-12-hydroxy-4-isopropylphenyl]-N'-[2-chloro-5-trifluoromethylphenyl]urea N-[2-hydroxy-4-isopropylphenyl]-N'-[2-chloro-5-trifluoromethylphenyl]urea was prepared from 2-amino-5-isopropylphenol (150 mg, 1.00 mmol, example 128a) according to the procedure in General Method B. The product was purified by precipitation from methylene chloride/hexane(1 equiv./20 equiv.) and filtering. (275 mg, 82%). $^1$H NMR (CD$_3$OD): δ 8.50 (s, 1H), 7.70 (s, 1H), 7.51 (d, 1H), 7.22 (d, 1H), 6.70 (m, 2H), 6.62 (dd, 1H), 2.76 (m, (1H), 1.16 (d, 6H).

EXAMPLE 143

Preparation of N-[2-hydroxy-3-phenylphenyl]-N'-[2,3-dichlorophenyl]urea a) Preparation of 2-nitro-6-phenylphenol 2-phenylphenol (3.00 g, 17.6 mmol) was dissolved in methylene chloride(40 ml) followed by the addition of sodium nitrate (1.65 g, 19.4 mmol). The addition of sulfuric acid (25 ml/3M) was then made, followed by addition of a catalytic amount of sodium nitrite. The mixture was allowed to stir. After 24 hrs, the reaction mixture was diluted with methylene chloride and extracted with water. The organic layer was dried over MgSO$_4$ and filtered. The solvent was evaporated and chromatography of the resulting solid on silica gel (4% MeOH/CH$_2$Cl$_2$) gave the desired product(900 mg, 24%). $^1$H NMR (CD$_3$COCD3): δ 8.19 (d,1H), 7.79 (d,1H), 7.64 (d, 2H), 7.50 (t, 2H), 7.45 (t, 1H), 7.22 (t, 1H).

b) Preparation of 2-amino-6-phenylphenol

To a solution of 2-nitro-6-phenylphenol(900 mg, 4.2 mmol) in methanol(50 ml) was added 10% Pd/C (100 mg). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH$_2$Cl$_2$) gave the desired product(700 mg, 90%). $^1$H NMR (CD$_3$OD): δ 7.55–7.27 (m, 5H), 6.77–6.61 (m, 3H).

c) Preparation of N-[2-hydroxy-3-phenylphenyl]-N'-[2,3-dichlorophenyl]urea

N-[2-hydroxy-3-phenylphenyl]-N'-[2,3-dichlorophenyl] urea was prepared from 2-amino-6-phenylphenol (92.5 mg, 0.50 mmol) according to the procedure in General Method B. The product was purified by precipitation from methylene chloride/hexane(1 equiv./20 equiv.) and filtering. (150 mg,81%). $^1$H NMR (CD$_3$OD): δ 8.06 (d, 1H),7.65 (d, 1H), 7.54 (d, 2H),7.40 (t, 2H), 7.32 (d, 1H) 7.22 (m, 2H), 7.04–6.88

Preparation of N-[2-hydroxy-3-phenylphenyl]-N'-[2,3-dichlorophenyl]urea b)N-(2-hydroxy-3-phenylphenyl]-N'-[2,3-dichlorophenyl]urea was prepared from 2-amino-6-phenylphenol (92.5 mg, 0.50 mmol) according to the procedure in General Method B. The product was purified by precipitation from methylene chloride/hexane(1 equiv./20 equiv.) and filtering. (150 mg, 81%). $^1$H NMR (CD$_3$OD): δ 8.06 (d, 1H),7.65 (d, 1H), 7.54 (d, 2H),7.40 (t, 2H), 7.32 (d, 1H) 7.22 (m, 2H), 7.04–6.88 (m, 2H).

EXAMPLE 144

Preparation of N-[2-hydroxy-5-nitrophenyl]-N'-[2-methoxyphenyl]urea

N-[2-hydroxy-5-nitrophenyl]-N'-[2-methoxyphenyl]urea was prepared from 2-amino-4-nitrophenol (154 mg, 1.00 mmol) according to the procedure in General Method B. The product was purified by precipitation from methylene chloride/hexane(1 equiv./20 equiv.) and filtering. (270 mg, 89%). $^1$H NMR (CD$_3$OD): δ 9.10 (s, 1H), 8.10 (d, 1H), 7.85 (d, 1H), 7.08–6.88 (m, 4H), 3.96 (s, 3H).

EXAMPLE 145

Preparation of N-[2-hydroxy-5-nitrophenyl]-N'-[3-trifluoromethylphenyl]urea

N-[2-hydroxy-5-nitrophenyl]-N'-[3-trifluoromethylphenyl]urea was prepared from 2-amino-4-nitrophenol (154 mg, 1.00 mmol) according to the procedure in General Method B. The product was purified by precipitation from methylene chloride/hexane(1 equiv./20 equiv.) and filtering. (290 mg, 85%). $^1$H NMR (CD$_3$OD): δ 9.12 (s, 1H), 7.89 (d, 1H), 7.68 (d, 1H), 7.55 (m, 2H), 7.45 (d, 1H), 7.00 (d, 1H).

EXAMPLE 146

Preparation of N-[2-hydroxy-5-nitrophenyl]-N'-[2-phenylphenyl]urea

N-[2-hydroxy-5-nitrophenyl]-N'-[2-phenylphenyl]urea was prepared from 2-amino-4-nitrophenol (154 mg, 1.00 mmol) according to the procedure in General Method B. The product was purified by precipitation from methylene chloride/hexane(1 equiv./20 equiv.) and filtering. (285 mg, 81%). $^1$H NMR (CD$_3$OD): δ 8.09 (s, 1H), 7.86 (d, 1H), 7.58–7.20 (m, 9H), 6.95 (d, 1H).

EXAMPLE 147

Preparation of N-[2-hydroxy-5-nitrophenyl]-N'-[2,3-dichlorophenyl]urea

N-[2-hydroxy-5-nitrophenyl]-N'-[2,3-dichlorophenyl]urea was prepared from 2-amino-4-nitrophenol (154 mg, 1.00 mmol) according to the procedure in General Method B. The product was purified by precipitation from methylene chloride/hexane(1 equiv./20 equiv.) and filtering. (290 mg, 85%). $^1$H NMR (CD$_3$OD): δ 9.11 (s, 1H), 8.17 (d, 1H), 7.89 (d, 1H), 7.34 (m, 2H), 6.95 (d, 1H).

EXAMPLE 148

Preparation of N-[2-hydroxy-5-ethylsulfonyphenyl]-N'-[2,3-dichlorophenyl]urea

N-[2-hydroxy-5-ethylsulfonylphenyl]-N'-[2,3-dichlorophenyl]urea was prepared from 2-amino-4-(ethylsulfonyl)phenol (185 mg, 1.00 mmol) according to the procedure in General Method B. The product was purified by precipitation from methylene chloride/hexane (1 equiv./20 equiv.) and filtering. (310 mg, 84%). $^1$H NMR (CD$_3$OD): δ 8.65 (s, 1H), 8.18 (d, 1H), 7.45 (d, 1H), 7.26 (m, 2H), 7.00 (d, 1H), 3.33 (q, 2H), 1.24 (t, 3H).
The following compounds of Formula (I) may be prepared in accordance with the examples and schemes as described above:

EXAMPLE 149

N-[2-(2-Amino-(4-trifluoromethyl)phenyl)sulfonylamino]phenyl]-N'-(2-bromophenyl)urea EI-MS m/z 527 (M−H)$^-$

EXAMPLE 150

N-[2-(aminosulfonylphenyl) 3-aminophenyl]N'-(2-bromophenyl)ureaEI-MS m/z 426 (M+H)$^+$ The following compounds of Formula (I) may be prepared in accordance with the examples and schemes as described above, or may also be purchased commercially from well recognized sources. For instance, from Aldrich Chemical Company:
N-(2-Hydroxy-4-nitrophenyl)-N'-phenylurea
For instance, from the Alfred Bader Collection of Aldrich Chemical:
1-(2-Carboxyphenyl)-3-(3-fluorophenyl)urea
1-(2-Carboxyphenyl)-3-(3-chlorophenyl)urea
Available from Gallard Schlesinger Company and/or the Sigma Aldrich Library of Rare Compounds:
1-(2-Carboxyphenyl)-3-(4chlorophenyl)urea
1-(p-Anisyl)-3-(2-carboxyphenyl)urea
   Available from Gallard Schlisinger Company:
2-(3,4-Dichlorophenylcarbonyldiimino)-5-trifluoromethylbenzoic acid
2-(4-Chlorophenylcarbonyldiimino)-5-trifluoromethylbenzoic acid
N-Phenyl-N'-(2-carboxyphenyl)urea
   From Maybridge Chemical Company, Cambridge England:
1,1'-(4Methyl-2-phenylene)bis[3-tolyl)]thiourea
N-(5-Chloro-2-hydroxy-4-nitrophenyl)-N'-phenylurea
   The following compounds of Formula (I) may be prepared in accordance with the examples and schemes as described above, or as indicated by their respective citations in Chemical Abstracts:
1-(m-Anisyl)-3-(2-carboxyphneyl)urea;
1-(o-Anisyl)-3-(2-carboxyphenyl)urea;
1-(2-Carboxyphenyl)-3-(3,4-dichlorophenyl)urea;
1-(2-Carboxyphenyl)-3-(2,4-dichlorophenyl)urea;

METHOD OF TREATMENT

The compounds of Formula (I), (Ia), (II) and (III), or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

For purposes herein, the compounds of Formula (I), (Ia), (Ib), (Ic), (II) and (III) all have the same dosages, and dosage formulations as that of Formula (I) are used interchangeably.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ or NAP-2.

The compounds of Formula (I) are administered in an amount sufficient to inhibit cytokine function, in particular IL-8,GROα, GROβ, GROγ or NAP-2, such that they are biologically regulated down to normal levels of physiological function, or in some case to subnormal levels, so as to ameliorate the disease state. Abnormal levels of IL-8, GROα, GROβ, GROγ or NAP-2 for instance in the context of the present invention, constitute: (i) levels of free IL-8 greater than or equal to 1 picogram per mL; (ii) any-cell associated IL-8, GROα, GROβ, GROγ or NAP-2 above normal physiological levels; or (iii)the presence of IL-8, GROα, GROβ, GROγ or NAP-2 above basal levels in cells or tissues in which IL-8, GROα, GROβ, GROγ or NAP-2 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis or undesired hematopoietic stem cells release.

These diseases are primarily characterized by massive neutrophil infiltration, T-cell infiltration, or neovascular growth, and are associated with increased IL-8, GROα, GROβ, GROγ or NAP-2 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ or NAP-2 has the unique property of promoting neutrophil chemotaxis, enzyme release including but not limited to elastase release as well as superoxide production and activation. The α-chemokines but particularly, GROα, GROβ, GROγ or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be dual inhibitors of both recombinant type I and type II IL-8 receptors. Preferably the compounds are inhibitors of only one receptor, preferably Type II.

As used herein, the term "IL-8 mediated disease or disease state" refers to any and all disease states in which IL-8, GROα, GROβ, GROγ or NAP-2 plays a role, either by production of IL-8, GROα, GROβ, GROγ or NAP-2 themselves, or by IL-8, GROα, GROβ, GROγ or NAP-2 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 α or β receptor plays a role, such as but not limited to IL-8, GRO-α, GRO-β, GRO-γ, or NAP-2. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytoline" refers to any secreted polypeptide that affects the functions of cells and is a molecule which modulates interactions between cells in the immune, inflammatory or hematopoietic response. A cytokine includes, but is not limited to, monolines and lympholiines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to, IL-8, GRO-α, GRO-β, GRO-γ, NAP-2, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the slin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal andlor fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenteraly, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral iahalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and Gro-α chemokine inhibitiory effects of compounds of the present invention were determined by the following in vitro assay:

Receptor Binding Assays:

[$^{125}$I] IL-8 (human recombinant) was obtained from Amersham Corp., Arlington Heights, Ill., with specific activity 2000 Ci/mmol. Gro-α was obtained from NEN-New England Nuclear. All other chemicals were of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp 2195–2205 (1974)). Except that the homogenization buffer was changed to 10 mM Tris-HCL, 1 mM MgSO$_4$, 0.5 mM EDTA (ethylene-diaminetetra-acetic acid), 1 mMPMSF (α-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained $^{125}$I IL-8 (0.25 nM) or $^{125}$I Gro-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest was added which had been pre-dissolved in DMSO so as to reach a final concentration of between 0.01 nM and 100 uM. The assay was initiated by addition of $^{125}$I-IL-8. After 1 hour at room temperature the plate was harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter was then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

All of the exemplified compounds of Formulas (I) to (III) noted herein in the Synthetic Chemistry Section, of Examples 1 to 150 plus the additional purchased compounds demonstrated an IC$_{50}$ from about 45 to about <1 μg/mL in the permissive models for IL-8 receptor inhibition. All of these compounds were also found to be inhibitors of Gro-a binding at about the same level. The compound 1-(2-Carboxyphenyl)-3-(4-chloro-2-methylphenyl)urea was found to be active at about 75 µg/mL.

The following compounds, generally tested at levels of up to 45 µg/mL were found to not demonstrate levels of IL-8 receptor antagonism within the criteria set forth above at the dosage levels tested. These compounds are:

1-(4-Chloro-alpha,alpha,alpha-trifluoro-3-tolyl)-3-[2-(4-chlorophenyl)thio]-5-chlorophenylurea
1-(6Chloro-alpha,alpha,alpha-trifluoro-3-tolyl)-3-[2-(4-chlorophenoxy)-5-chlorophenyl]urea
1-(2-Mercaptophenyl)-3-phenyl-2-thiourea
1-(2-Hydroxyphenyl)-3-phenyl-2-thiourea
3,3'-(Carbonothioyldiimino)bis[4-hydroxybenzoic acid]
m,m'-(1,3-thioureylene)di(4-hydroxybenzoic acid)
1-(2-Tolyl)-3-(3-chloro-6-hydroxyphenyl)-2-thiourea
1-[(2-Hydroxy-4-aminophenyl)]-(3-phenyl)-urea
N-(2-Carboxy-4-trifluromethylphenyl)-N'-(3-chlorophenyl)urea
N-(2-Carboxyphenyl)-N'-(2,5-dichlorophenyl)urea
1-(2-Carboxyphenyl)-3-(2-Chloro-5-trifluoromethylphenyl)urea
2-[2-[3-(4-Bromophenyl)ureido]-4-trifluoromethylphenoxy]benzoic acid;
2-[2-[3-(4-Chlorophenyl)ureido]phenoxy]benozic acid
2-[2-[3-(4-Chloro3-(trifluromethyl)phenyl)ureido]phenoxy]benozic acid
N-(2-Hydroxyphenyl)-N'-phenylurea
N-[2-Hydroxy-5-(methoxycarbonyl)phenyl]-N'-phenylurea
N-[4-Carboxy-2-hydroxyphenyl]-n'-phenylurea
N-(2-Hydroxy-4-nitrophenyl)-N'-(4-nitrophenyl)urea;
1-(2-Carboxyphenyl)-3-(2,6-xylyl)urea
1-(6-Carboxy-2,4-dichlorophenyl)-3-(2,4,6-trichlorophenyl)urea
1-(2-Carboxyphenyl)-3-(2,5-dimethoxyphenyl)urea
1-(2-Carboxyphenyl)-3-(2-methylphenyl)urea
1-[(2-Hydroxyphenyl)-3-(2-methyl)-5-nitrophenyl]urea
1-(2,5-Dichlorophenyl)-3-(2-hydroxy-4-nitrophenyl)urea
1-(2-Carboxyphenyl)-3-(4-chloro-2-methylphenyl)urea
N-(2-phenylsulfonylaminophenyl-N'-phenylurea
N-(2-Hydroxy-4-nitrophenyl)-N'-(4-ethoxycarbonylphenyl)urea
N-(2-Hydroxy-4-nitrophenyl)-N'-(2-ethoxycarbonylphenyl)urea
N-(2-Hydroxy-4-nitrophenyl)-N'-(3-ethoxycarbonylphenyl)urea
N-(2-Hydroxy-4-nitrophenyl)-N'-(4-phenylphenyl)urea
N-(2-Hydroxy-4-nitrophenyl)-N'-(4-phenoxyphenyl)urea
N-(2-Hydroxy-4-nitrophenyl)-N'-(4-propylphenyl)urea
N-(4-Trifluromethyl-2-(4-nitrobenzenesulfonyl)amino]-N'-phenylurea
N-(3-Carboxyphenyl)-N'-2-hydroxy-4-nitrophenyl)urea
N-(4-Trifluromethyl-2-(methylsulfonyl)amino]-N'-phenylurea
N-(2-Hydroxy-4-nitrophenyl)-N'-[2-(isopropyl)phenyl)urea
N-(2-Hydroxy-4-nitrophenyl)-N'-(2,6-dimethylphenyl)urea
N-(2-Hydroxy-4-nitrophenyl)-N'-(2-fluoro-5-nitrophenyl)urea
N-(2-Hydroxy-4-nitrophenyl)-N'-(2-chloro-5-trifluromethylphenyl)urea
N-(2-Hydroxy-4-nitrophenyl)-N'-(2-methoxy-4-nitrophenyl)urea
N-(2-Hydroxy-1-napthyl)-N'-(2-phenylphenyl)urea
N-(2-Hydroxy-5-ethylsulfonylphenyl)-N'-(2-bromophenyl)urea
N-(2-hydroxy 3,4 dichlorophenyl)-N'-(4-phenylphenyl)urea
N-(2-hydroxy-3-naphthyl)-N'-(2-methoxyphenyl)urea
N-(2-hydroxy-3-naphthyl)-N'-(2-phenylphenyl)urea
N-(2-Hydroxy-3-naphthyl)-N'-(4-methoxyphenyl)urea
N-(2-Hydroxy-3-naphthyl)-N'-(3-trifluoromethylphenyl)urea
N-(2-Hydroxy-3-naphthyl)-N'-(4-phenylphenyl)urea
N-[2-(2-Carboxyphenylsulfonylamino)phenyl]-N'-(2-bromophenyl)urea
N-(2-Hydroxy-3-phenylphenyl)-N'-(2-methoxyphenyl)urea
N-(2-Hydroxy-3-phenylphenyl)-N'-(4-methoxyphenyl)urea
N-(2-Hydroxy-3-phenylphenyl)-N'-(3-triflouromethylphenyl)urea
N-(2-Hydroxy-3-phenylphenyl)-N'-(2-phenylphenyl)urea
N-(2-Hydroxy-3-phenylphenyl)-N'-(2-phenylphenyl)urea
N-[2-[(2,5-Dichlorothien3-yl)sulfonylamino]phenyl]-N'-(2-bromophenyl)urea
N-(2-Hydroxy,3,4-dichlorophenyl)-N'-(2,4 dimethoxyphenyl)urea
N-(2-Hydroxy,3,4-dichlorophenyl)-N'-(2-chloro-5-trifloromethylphenyl)urea
N-(2-Hydroxy-3-naphthyl)-N'-(2,4 dimethoxyphenyl)urea
N-(2-Hydroxy-3-naphthyl)-N'-(2-chloro-5-trifluoromethylphenyl)urea
N-(2-Hydroxy-3 -phenylphenyl)-N'-(2,4-dimethoxyphenyl)urea
N-(2-Hydroxy-4-isopropylphenyl)-N'-(2,4-dimethoxyphenyl)urea
N-(2-Hydroxy-3-phenylphenyl)-N'-(2-chloro-5-trifluoromethylphenyl)urea
N-(2-Hydroxy-5-nitrophenyl)-N'-(2,4-dimethoxyphenyl)urea
N-(2-Hydroxy-5-nitrophenyl)-N'-(2-chloro-5-trifluoromethylphenyl)urea
N-(2-Hydroxy-3-cyanophenyl)-N'-(4-methoxyphenyl)urea
N-(2-Hydroxy-3-cyanophenyl)-N'-(4-phenylphenyl)urea
N-(2-Hydroxy-3-cyanophenyl)-N'-(2,4 dimethoxyphenyl)urea
N-(2-Hydroxy-3-cyanophenyl)-N'-(2-chloro-5-trifluoromethylphenyl)urea
N-(2-Hydroxy-5-phenylphenyl)-N'-(2-methoxyphenyl)urea
N-(2-Hydroxy-5-phenylphenyl)-N'-(methoxyphenyl)urea
N-(2-Hydroxy-5-phenylphenyl)-N'-(3-trifluoromethylphenyl)urea
N-(2-Hydroxy-5-phenylphenyl)-N'-(2-phenylphenyl)urea
N-(2-Hydroxy-5-phenylphenyl)-N'-(4-phenylphenyl)urea
N-(2-Hydroxy-5-phenylphenyl)-N'-(2,3-dichlorophenyl)urea
N-(2-Hydroxy-5-phenylphenyl)-N'-(2,4-dimethoxyphenyl)urea
N-(2-Hydroxy-5-phenylphenyl)-N'-(2-chloro-5-trifluoromethylphenyl)urea
N-(2-Hydroxy-5-ethylsulfonylphenyl)-N'-(4-methoxyphenyl)urea
N-(2-Hydroxy-5-ethylsulfonylphenyl)-N'-(3-trifluoromethylphenyl)urea
N-(2-Hydroxy-5-ethylsulfonylphenyl)-N'-(2-phenylphenyl)urea
N-(2-Hydroxy-5-ethylsulfonylphenyl)-N'-(4-phenylphenyl)urea
N-(2-Hydroxy-5-ethylsulfonylphenyl)-N'-(2,4-dimethoxyphenyl)urea
N-(2-Hydroxy-5-ethylsulfonylphenyl)-N'-(2-chloro-5-trifluoromethylphenyl)urea
N-[2-Hydroxy-3,4-dichlorophenyl]-N'-[2,4 dimethoxyphenyl]urea
N-[2-Hydroxy-3,4-dichlorophenyl]-N'-[2-chloro-5-trifluoromethylphenyl]urea N-[2-Hydroxy-3-naphthyl]-N'-[3-trifluoromethylphenyl] urea Chemotaxis Assay:

The in vitro inhibitory properties of these compounds were determined in the neutrophil chemotaxis assay as described in Current Protocols in Immunology, vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 where placed in the bottom chamber of a 48 multiwell chamber (Neuro Probe, Cabin John. Md.) at a concentration between 0.1 and 100 nM. The two chambers where separated by a 5 um polycarbonate filter. When compounds of this invention were tested, they where mixed with the cells (0.001–1000 nM) just prior to the addition of the cells to the upper chamber. Incubation was allowed to proceed for between about 45 and 90 min at about 37° C. in a humidified incubator with 5% $CO_2$. At the end of the incubation period, the polycarbonate membrane was removed and the top side washed, the membrane was then stained using the Diff Quick staining protocol (Baxter Products, McGaw Park, Ill., USA). Cell which had chemotaxed to the chemokine were visually counted using a microscope. Generally, four fields where counted for each sample, these number where averaged to give the average number of cells which had migrated. Each sample was tested in triplicate and each compound repeated at least four times. To certain cells (positive control cells) no compound was added, these cells represent the maximum chemotactic response of the cells. In the case where a negative control (unstimulated) was desired, no chemokine was added to the bottom chamber. The difference between the positive control and the negative control represents the chemotactic activity of the cells.

Elastase Release Assay:

The compounds of this invention where tested for their ability to prevent Elastase release from human neutrophils. Neutrophils where isolated from human blood as described in Current Protocols in Immunology Vol I, Suppl 1 Unit 7.23.1. PMNs $0.88 \times 10^6$ cells suspended in Ringer's Solution (NaCl 118, KCl 4.56, NaHCO3 25, KH2PO4 1.03, Glucose 11.1, HEPES 5 mM, pH 7.4) where placed in each well of a 96 well plate in a volume of 50 ul. To this plate was added the test compound (0.001–1000 nM) in a volume of 50 ul, Cytochalasin B in a volume of 50 ul (20 ug/ml) and Ringers buffer in a volume of 50 ul. These cells where allowed to warm (37° C., 5% CO2, 95% RH) for 5 min before IL-8, GROα, GROβ, GROγ or NAP-2 at a final concentration of 0.01–1000 nM was added. The reaction was allowed to proceed for 45 min before the 96 well plate was centrifuiged (800×g 5 min) and 100 ul of the supernatant removed. This suppernatant was added to a second 96 well plate followed by an artificial elastas substrate (MeOSuc-Ala-Ala-Pro-Val-AMC, Nova Biochem, La Jolla, Calif.) to a final concentration of 6 ug/ml dissolved in phosphate buffered saline. Immediately, the plate was placed in a fluorescent 96 well plate reader (Cytofluor 2350, Millipore, Bedford, Mass.) and data collected at 3 min intervals according to the method of Nakajima et al J. Biol Chem 254 4027 (1979). The amount of Elastase released from the PMNs was calculated by measuring the rate of MeOSuc-Ala-Ala-Pro-Val-AMC degradation.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chemokine mediated disease, wherein the chemokine binds to an IL-8 α or β receptor in a mammal, which method comprises administering to said mammal an effective amount of a compound of the formula:

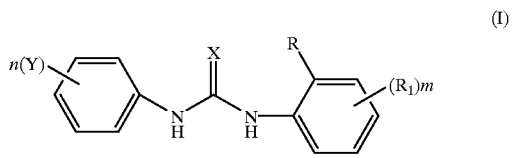

(I)

wherein

X is oxygen or sulfur;

R is $C(O)NR_6R_7$;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl$C_{2-10}$alkenyl; heteroaryl $C_{2-10}$ alkenyl; heterocyclic$C_{2-10}$ alkenyl; $NR_4R_5$; $C_{2-10}$alkenylC(O)$NR_4R_5$; C(O)$NR_4R_5$; C(O)$NR_4R_{10}$; $S(O)_3H$; $S(O)_3R_8$; $C_{1-10}$ alkyl $C(O)R_{11}$; $C_{2-10}$alkenyl $C(O)R_{11}$; $C_{2-10}$ alkenyl $C(O)OR_{11}$; $C(O)R_{11}$; $C(O)OR_{12}$; $OC(O)R_{11}$; $NR_4C(O)R_{11}$; or two $R_1$ moieties together may form O—$(CH_2)_s$O— or a 5 to 6 membered unsaturated ring;

t is 0, or an integer having a value of 1 or 2;

s is an integer having a value of 1 to 3;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O/N/S;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $S(O)_tR_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl$C_{1-4}$ alkyloxy; heterocyclic, heterocyclic$C_{1-4}$alkyl; aryl$C_{2-10}$alkenyl; heteroaryl $C_{2-10}$ alkenyl; heterocyclic$C_{2-10}$ alkenyl; $NR_4R_5$; $C_{2-10}$alkenylC(O)$NR_4R_5$; C(O)$NR_4R_5$; C(O)$NR_4R_{10}$; [$S(O)_3H$;] $S(O)_3R_8$; $C_{1-10}$alkylC(O)$R_{11}$; $C_{2-10}$ alkenyl $C(O)R_{11}$; $C_{2-10}$ alkenyl $C(O)OR_{11}$; $C(O)R_{11}$;

C(O)OR$_{12}$; OC(O)R$_{11}$; NR$_4$C(O)R$_{11}$; or two Y moieties together may form O—(CH$_2$)$_s$O— or a 5 to 6 membered unsaturated ring;

n is an integer having a value of 1 to 3;

m is an integer having a value of 1 to 3;

R$_8$ is hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, optionally substituted aryl, optionally substituted aryl C$_{1-4}$alkyl, optionally substituted heteroaryl, optionally substituted heteroaryl C$_{1-4}$alkyl, optionally substituted heterocyclic, or optionally substituted heterocyclic C$_{1-4}$alkyl;

R$_{12}$ is hydrogen, C$_{1-10}$ alkyl, optionally substituted aryl or optionally substituted arylalkyl;

or a pharmaceutically acceptable salt thereof.

2. The method according to claim 1 wherein R$_1$ is halogen, cyano, nitro, CF$_3$, C(O)NR$_4$R$_5$, alkenyl C(O)NR$_4$R$_5$, C(O)R$_4$R$_{10}$, alkenyl C(O)OR$_{12}$, heteroaryl, heteroarylalkyl, or heteroaryl alkenyl.

3. The method according to claim 1 wherein Y is halogen, C$_{1-4}$ alkoxy, optionally substituted aryl, optionally substituted arylalkoxy, methylene dioxy, NR$_4$R$_5$, thioC$_{1-4}$alkyl, thioaryl, halosubstituted alkoxy, optionally substituted C$_{1-4}$alkyl, or hydroxy alkyl.

4. The method according to claim 1 wherein R$_1$ is substituted in the 3-position, the 4-position or di substituted in the 3,4-position by an electron withdrawing moiety.

5. The compound according to claim 1 wherein Y is mono-substituted in the 2'-position or 3'-position, or is disubstituted in the 2'- or 3'-position of a monocyclic ring.

6. The compound according to claim 1 wherein n amd m are each equal to 1 or more.

7. The method according to claim 1 wherein the chemokine mediated disease is selected from psoriasis, atopic dermatitis, asthnma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulo-nephritis, or thrombosis, alzheimers disease, graft vs. host reaction, and allograft rejections.

* * * * *